US005608060A

United States Patent [19]

Axworthy et al.

[11] Patent Number: 5,608,060

[45] Date of Patent: Mar. 4, 1997

[54] BIOTINIDASE-RESISTANT BIOTIN-DOTA CONJUGATES

[75] Inventors: Donald B. Axworthy, Brier; Louis J. Theodore, Lynnwood; Linda M. Gustavson, Seattle; John M. Reno, Brier, all of Wash.

[73] Assignee: NeoRx Corporation, Seattle, Wash.

[21] Appl. No.: 351,469

[22] PCT Filed: Jun. 7, 1993

[86] PCT No.: PCT/US93/05406

§ 371 Date: Feb. 21, 1995

§ 102(e) Date: Feb. 21, 1995

[87] PCT Pub. No.: WO93/25240

PCT Pub. Date: Dec. 23, 1993

Related U.S. Application Data

[63] Continuation-in-part of Ser. No. 995,383, Dec. 23, 1992, abandoned, and a continuation-in-part of Ser. No. 995,381, Dec. 23, 1992, abandoned, each is a continuation-in-part of Ser. No.895,588, Jun. 9, 1992, Pat. No. 5,283,342.

[51] Int. Cl.[6] .................... C07D 257/02; C07D 495/04; A61K 31/415; C07H 17/04

[52] U.S. Cl. .................... 540/474; 548/304.1; 536/1.11; 536/17.4; 536/53; 424/9.363

[58] Field of Search .................... 540/474; 548/304.1; 514/387; 536/53, 54, 17.4, 1.11; 424/1.49, 9.363

[56] References Cited

U.S. PATENT DOCUMENTS

| | | |
|---|---|---|
| 4,639,365 | 1/1987 | Sherry . |
| 4,647,447 | 3/1987 | Gries et al. . |
| 4,678,667 | 7/1987 | Meares et al. . |
| 4,863,713 | 9/1989 | Goodwin et al. . |
| 4,923,985 | 5/1990 | Gansow et al. . |
| 5,141,966 | 8/1992 | Porath . |
| 5,246,692 | 9/1993 | Gansow et al. . |
| 5,256,395 | 10/1993 | Barbet et al. . |
| 5,277,895 | 1/1994 | Platzek et al. . |
| 5,326,778 | 7/1994 | Rosebrough . |

FOREIGN PATENT DOCUMENTS

| | | |
|---|---|---|
| 0327365 | 8/1989 | European Pat. Off. . |
| WO90/12050 | 10/1990 | European Pat. Off. . |
| 0451824 | 10/1991 | European Pat. Off. . |
| 0496074 | 7/1992 | European Pat. Off. . |
| WO88/08422 | 11/1988 | Germany . |
| WO89/10140 | 11/1989 | WIPO . |
| WO91/09628 | 7/1991 | WIPO . |

OTHER PUBLICATIONS

Rosebrough, J. Pharmacol. Exp. Ther., 1993, 265(1):408 Wu et al., Nucl. Med. Biol., 1992, 19(2):239.

Weber et al., "Enhanced Kidney Clearance with an Ester–Linked $^{99m}$Tc–Radiolabeled Antibody Fab'–Chelator Conjugate," *Bioconjugate Chem.*, vol. 1, pp. 431–437, 1990.

Wall et al., "The Galactose–Specific Recognition System of Mammalian Liver: the Route of Ligand Internalization in Rat Hepatocytes," *Cell*, vol. 21, pp. 79–93, 1980.

Lee et al., "2–Imino–2–methoxyethyl 1–Thioglycosides: New Reagents for Attaching Sugars to Proteins," *Biochem.*, vol. 15, No. 18, pp. 3956–3962, 1976.

Krantz et al., "Attachment of Thioglycosides to Proteins: Enhancement of Liver Membrane Binding," *Biochem.*, vol. 15, No. 18, pp. 3963–3968, 1976.

Van Der Sluijs et al., "Drug Targeting to the Liver with Lactosylated Albumins: Does the Glycoprotein Target the Drug or is the Drug Targeting the Glycoprotein?", *Hepatology*, vol. 6, No. 4, pp. 723–728, 1986.

Sharon et al., "Carbohydrates in Cell Recognition", *Scientific American*, vol. 268, No. 1, Jan. 1993, pp. 82–89.

Morell et al., "The Role of Sialic Acid in Determining the Survival of Glycoproteins in the Circulation," *J. Biol. Chem.*, vol. 246, No. 5, pp. 1461–1467, 1971.

Tolleshaug, "Binding and Internalization of Asialo–glycoproteins by Isolated Rat Hepatocytes," *Int. J. Biochem.*, vol. 13, pp. 45–51, 1981.

Galli et al., "A Radiopharmaceutical for the Study of the Liver: $^{99m}$Tc–DTPA–Asialo–Orosomucoid I: Radiochemical and Animal Distribution Studies," *J. Nucl. Med.*, vol. 32, No. 2, pp. 110–116, 1988.

Sharma et al., "Inactivation and Clearance of an anti–CEA carboxypeptidase G2 Conjugate in Blood after Localization in a Xenograft Model," *Br. J. Cancer*, vol. 61, pp. 659–662, 1990.

Jansen et al., "Hepatic Endocytosis of Various Types of Mannose–terminated Albumins," *J. of Biological Chem.*, vol. 266, No. 5, pp. 3343–3348, 1991.

Sheldon et al., "Targeting of [$^{111}$In]Biocytin to Cultured Ovarian Adenocarcinoma Cells Using Covalent Monoclonal Antibody–Streptavidin Conjugates," *Appl. Radiat. Isot.*, vol. 43, No. 11, pp. 1399–1402, 1992.

Goodwin, "New Methods for Localizing Infection: A Role for Avidin–Biotin?," *J. Nucl. Med.*, vol. 33, No. 10, pp. 1816–1818, 1992.

Goodwin et al., "Pretargeted Immunoscintigraphy: Effect of Hapten Valency on Murine Tumor Uptake," *J. Nucl. Med.*, vol. 33, No. 11, pp. 2006–2013, 1992.

McMurry et al., "Convenient Synthesis of Bifunctional Tetraaza Macrocycles," *Bioconjugate Chem.*, vol. 3, No. 2, pp. 108–117, 1992.

Renn and Meares, "Large–Scale Synthesis of the Bifunctional Chelating Agent 2–(p–Nitrobenzyl)–1,4,7,10–tetraazacyclododecane–N,N',N'',N'''–tetraacetic Acid, and the Determination of Its Enatiomeric Purity by Chiral Chromatography," *Bioconjugate Chem.*, vol. 3, No. 6, pp. 563–569, 1992.

(List continued on next page.)

*Primary Examiner*—Frank C. Eisenschenk
*Attorney, Agent, or Firm*—Burns, Doane, Swecker & Mathis, L.L.P.

[57] ABSTRACT

Biotinidase-resistant biotin-DOTA conjugates, and methods of use thereof in diagnostic and therapeutic pretargeting methods are provided. These conjugates are useful in diagnosis and treatment of cancer.

9 Claims, 22 Drawing Sheets

OTHER PUBLICATIONS

Koch and Mäcke, "$^{99m}$Tc Labeled Biotin Conjugate in a Tumor Pretargeting Approach with Monoclonal antibodies," *Angew. Chem. Intl. Ed. Engl.*, vol. 31, No. 11, pp. 1507–1509, 1992.

Wu et al., "Investigations of N–linked Macrocycles for $^{111}$In and $^{90}$Y Labeling of Proteins," *Nucl. Med. Biol. Int. J. Radiat. Appl. Instrum. Part B*, vol. 19, No. 2, pp. 239–244, 1992.

Goodwin et al., Abstract No. 232, "Pharmacokinetics of Biotin–Chelate Conjugates for Pretargeted Avidin–Biotin Immunoscintigraphy," *J. Nucl. Med.* p. 880, 1992.

Dischino et al., "Synthesis of Nonionic Gadolinium Chelates Useful as Contrast Agents for Magnetic Resonance Imaging. 1,4,7–Tris(carboxymethyl)–10–substituted–1,4,7,10–tetraazacyclododecanes and Their Corresponding Gadolinium Chelates," *Inorg. Chem.*, vol. 30, pp. 1265–1269, 1991.

Sieving et al., "Preparation and Characterization of Paramagnetic Polychelates and Their Protein Conjugates," *Bioconjugate Chem.*, vol. 1, pp. 65–71, 1990.

Parker et al., "Implementation of macrocyclic conjugated antibodies for tumour–targeting," *Pure & Appl. Chem.*, vol. 61, No. 9, pp. 1637–1641, 1989.

Riesen et al., "Synthesis and X–Ray Structural Characterization of Seven Co–ordinate Macrocyclic $In^{3+}$Complexes with Relevance to Radiopharmaceutical Applications," *J. Chem. Soc., Chem. Commun.*, pp. 460–462, 1989.

Moi et al., "The Peptide Way to Macrocyclic Bifunctional Chelating Agents: Synthesis of 2–(p–Nitrobenzyl)–1,4,7,10–tetraazacyclododecane–N,N',N",N'"–tetraacetic Acid and Study of Its Yttrium(III) Complex," *J. Am. Chem. Soc.*, vol. 110, pp. 6266–6267, 1988.

Kasprzyk and Wilkins, "Kinetics of Interaction of Metal Ions with Two Tetraaza Tetraacetate Macrocycles," *Inorg. Chem.*, vol. 21, pp. 3349–3352, 1982.

International Search Report cited in PCT Patent Application No. PCT/US93/05406.

Virzi et al., "New Indium–111 Labeled Biotin Derivates for Improved Immunotargeting", *Nucl. Med. Biol.*, vol. 18, No. 7, pp. 719–726, 1991.

Green, "The use of [$^{14}$C]Biotin for Kinetic Studies and for Assay," *Biochem. J.*, 89:585, 1963.

Kalofonos et al., "Imaging of Tumor in Patients with Indium–111–Labeled Biotin and Streptavidin–Conjugated Antibodies: Preliminary Communication," *J. Nucl. Med.*, vol. 31, No. 11, pp. 1791–1796, 1990.

Hnatowich et al., "Investigations of Avidin and Biotin for Imaging Applications," *J. Nucl. Med.*, vol. 28, No. 8, pp. 1294–1302, 1987.

Paganelli et al., "Intraperitoneal Radio–Localization of Tumors Pre–Targeted by Biotinylated Monoclonal Antibodies," *Int. J. Cancer*, 45:1184–1189, 1990.

Paganelli et al., "Monoclonal antibody pretargeting techniques for tumour localization: the avidin–biotin system," *Nulcear Medicine Communications*, 12:211–234, 1991.

Goodwin/Hnatowich, Letter to the Editor/Reply, *J. Nucl. Med.*, vol. 32, No. 4, pp. 750–751, 1991.

Rosebrough, Abstract No. 235, "Plasma Stability and Pharmacokinetics of Radio–Labeled Deferoxamine–Biotin Derivatives," *J. Nucl. Med.*, p. 880, 1992.

Virzi et al., Abstract No. 403, "The Preparation and Evaluation of 12 Biotin Derivatives Labeled with Tc–99M," *J. Nucl. Med.*, p. 920, 1992.

Rosario et al., Abstract No. 356, "Bolton–Hunter and Biotin Derivatized Polylysine: A New MultiValent Peptide Reagent for In Vivo Pre–Targeting with Streptavidin Conjugates," *J. Nucl. Med.*, vol. 32, No. 5, p. 993, 1991.

Vera et al., "Tc–99m Galactosyl–Neoglycoalbumin: In vitro Characterization of Receptor–Mediated Binding," *J. Nucl. Med.*, vol. 25, No. 7, pp. 779–787, 1984.

Haensler et al., "Synthesis and Characterization of a Trigalactosylated Bisacridine Compound to Target DNA to Hepatocytes," *Bioconjugate Chem.*, 4:85–93, 1993.

Mauk et al., "Targeting of Lipid Vesicles: Specificity of Carbohydrate Receptor Analogues for Leukocytes in Mice," *Proc. Natl. Acad. Sci. USA*, 77(8): 4430–4, 1980.

Ponpipom et al., "Cell surface carbohydrates for targeting studies," *Can. J. Chem.*, 58: 214, 1980.

Ponpipom et al., "Cell–Specific Ligands for Selective Drug Delivery to Tissues and Organs," *J. Med. Chem.*, 24:1388–95, 1981.

Weigel, *GlycoConjugates Composition, Struture and Function*, "Chapter 14, Mechanisms and Control of Glycoconjugate Turnover," edited by Allen et al., Marcel Dekker, Inc., New York, 421–97, 1992.

Weigel, *Subcellular Biochemistry, vol. 19, Endocytic Components: Identification and Characterization*, "Chapter 5, Endocytosis and Function of the Hepatic Asialoglycoprotein Receptor", edited by Bergeron et al., Plenum Press, New York, 125–61, 1993.

| | %ID | | | | | | | | | |
|---|---|---|---|---|---|---|---|---|---|---|
| | +PBS | SD | +NON-BT | SD | +10:1 | SD | +5:1 | SD | BT-SAT'D | SD |
| BLOOD | 31.05 | 5.08 | 29.94 | 1.35 | 8.54 | 0.91 | 7.03 | 0.18 | 24.58 | 0.68 |
| TAIL | 2.43 | 0.70 | 1.80 | 0.09 | 1.46 | 0.09 | 1.76 | 0.04 | 1.96 | 0.40 |
| LUNG | 1.47 | 0.26 | 1.09 | 0.22 | 0.54 | 0.10 | 0.48 | 0.07 | 0.76 | 0.01 |
| LIVER | 5.42 | 0.69 | 4.66 | 0.36 | 9.60 | 1.20 | 9.11 | 0.41 | 6.76 | 0.06 |
| SPLEEN | 0.25 | 0.05 | 0.34 | 0.03 | 0.17 | 0.03 | 0.18 | 0.00 | 0.38 | 0.02 |
| STOMACH | 0.28 | 0.02 | 0.33 | 0.03 | 0.53 | 0.34 | 0.49 | 0.00 | 0.29 | 0.04 |
| KIDNEY | 1.72 | 0.24 | 1.38 | 0.08 | 2.76 | 0.00 | 3.28 | 0.32 | 1.58 | 0.08 |
| INTESTINE | 3.40 | 0.73 | 3.44 | 0.10 | 4.22 | 0.02 | 6.62 | 0.14 | 2.83 | 0.13 |
| | 46.02 | | 42.98 | | 27.83 | | 28.95 | | 39.13 | |
| | Group 1 | | Group 2 | | Group 3 | | Group 4 | | Group 5 | |

FIG. 8

BIOTINIDASE-RESISTANT BIOTIN-DOTA CONJUGATES

This application is the U.S. national stage application of International application Ser. No. PCT/US93/05406, filed Jun. 7, 1993, which was a continuation-in-part of U.S. application Ser. No. 07/995,381, filed Dec. 23, 1992, now abandoned, and of U.S. application Ser. No. 07/995,383, filed Dec. 23, 1992, now abandoned, both of which were continuation-in-part applications based on U.S. application Ser. No. 07/895,588, filed Jun. 9, 1992, now U.S. Pat. No. 5,283,342, issued Feb. 1, 1994, and claims the benefit of the filing dates thereof under 35 U.S.C. §120.

TECHNICAL FIELD

The present invention relates to methods, compounds, compositions and kits useful for delivering to a target site a targeting moiety that is conjugated to one member of a ligand/anti-ligand pair. After localization and clearance of the targeting moiety conjugate, direct or indirect binding of a diagnostic or therapeutic agent conjugate at the target site occurs. Methods for radiometal labeling of biotin and for improved radiohalogenation of biotin, as well as the related compounds, are also disclosed. Also, clearing agents, anti-ligand-targeting moiety conjugates, target cell retention enhancing moieties and additional methods are set forth.

BACKGROUND OF THE INVENTION

Conventional cancer therapy is plagued by two problems. The generally attainable targeting ratio (ratio of administered dose localizing to tumor versus administered dose circulating in blood or ratio of administered dose localizing to tumor versus administered dose migrating to bone marrow) is low. Also, the absolute dose of radiation or therapeutic agent delivered to the tumor is insufficient in many cases to elicit a significant tumor response. Improvement in targeting ratio or absolute dose to tumor is sought.

SUMMARY OF THE INVENTION

The present invention is directed to diagnostic and therapeutic pretargeting methods, moieties useful therein and methods of making those moieties. Such pretargeting methods are characterized by an improved targeting ratio or increased absolute dose to the target cell sites in comparison to conventional cancer therapy.

The present invention describes chelate-biotin compounds and radiohalogenated biotin compounds useful in diagnostic and therapeutic pretargeting methods. The present invention also provides targeting moiety-ligand, such as biotin, compounds useful in diagnostic and therapeutic pretargeting methods. Selection of moieties and methodologies used to enhance internalization (of chemotherapeutic drugs, for example) or to enhance retention at the target cell surface (of radionuclides, for example) is also discussed.

In addition, the present invention provides targeting moiety-anti-ligand, such as avidin or streptavidin, compounds useful in diagnostic and therapeutic pretargeting methods. Other ligand-anti-ligand systems including the zinc finger protein-dsDNA fragment binding pair are also contemplated. Preparation and purification of such anti-ligand-targeting moiety compounds are also discussed.

The present invention also provides clearing agents to facilitate the removal of circulating targeting moiety-ligand (two-step) or targeting moiety-anti-ligand (two-step) or anti-ligand (three-step) from the mammalian recipient. Preferred clearing agents are classifiable as galactose-based and non-galactose-based. Within each category, preferable clearing agents are polymeric or protein based. Particulate agents, extracorporeal procedures and in vivo devices are also contemplated for use in the practice of the present invention.

Also, the present invention is directed to methods using streptavidin as an anti-ligand to enhance retention of radionuclide at target cell sites, with pretargeting protocols constituting one such method. More specifically, these embodiments of the present invention involve either (1) targeting moiety-streptavidin-radionuclide (with the radionuclide bound to streptavidin directly or through a chelate or linker), as well as (2) targeting moiety-biotin administered prior to streptavidin-radionuclide, or (3) biotin-radionuclide bound to a pretargeted streptavidin containing molecule.

The present invention further provides pretargeting methods employing intraarterial or other local administration of the therapeutic moiety-containing molecule to achieve greater localization thereof to artery-supplied target cell populations. Other methods of the present invention involve administration of short duration bone marrow protecting agents or vascular permeability enhancing agents prior to radionuclide-ligand molecule or radionuclide-anti-ligand molecule administration. Further, monovalent targeting moieties, such as Fv or Fab antibody fragments, are useful in the inventive pretargeting methods. Delivery of other, non-radioactive therapeutic agents, such as chemotherapeutic drugs, anti-tumor agents (e.g., cytokines) and toxins, to target cells using the pretargeting methods of the present invention is also described.

BRIEF DESCRIPTION OF THE DRAWINGS

FIG. 8 shows limited biodistribution data for LU-10-StrAv conjugate upon administration of three controls (Groups 1, 2 and 5) and two doses of clearing agent (Groups 3 and 4) at two hours post-clearing agent administration.

DETAILED DESCRIPTION OF THE INVENTION

Figure 1:
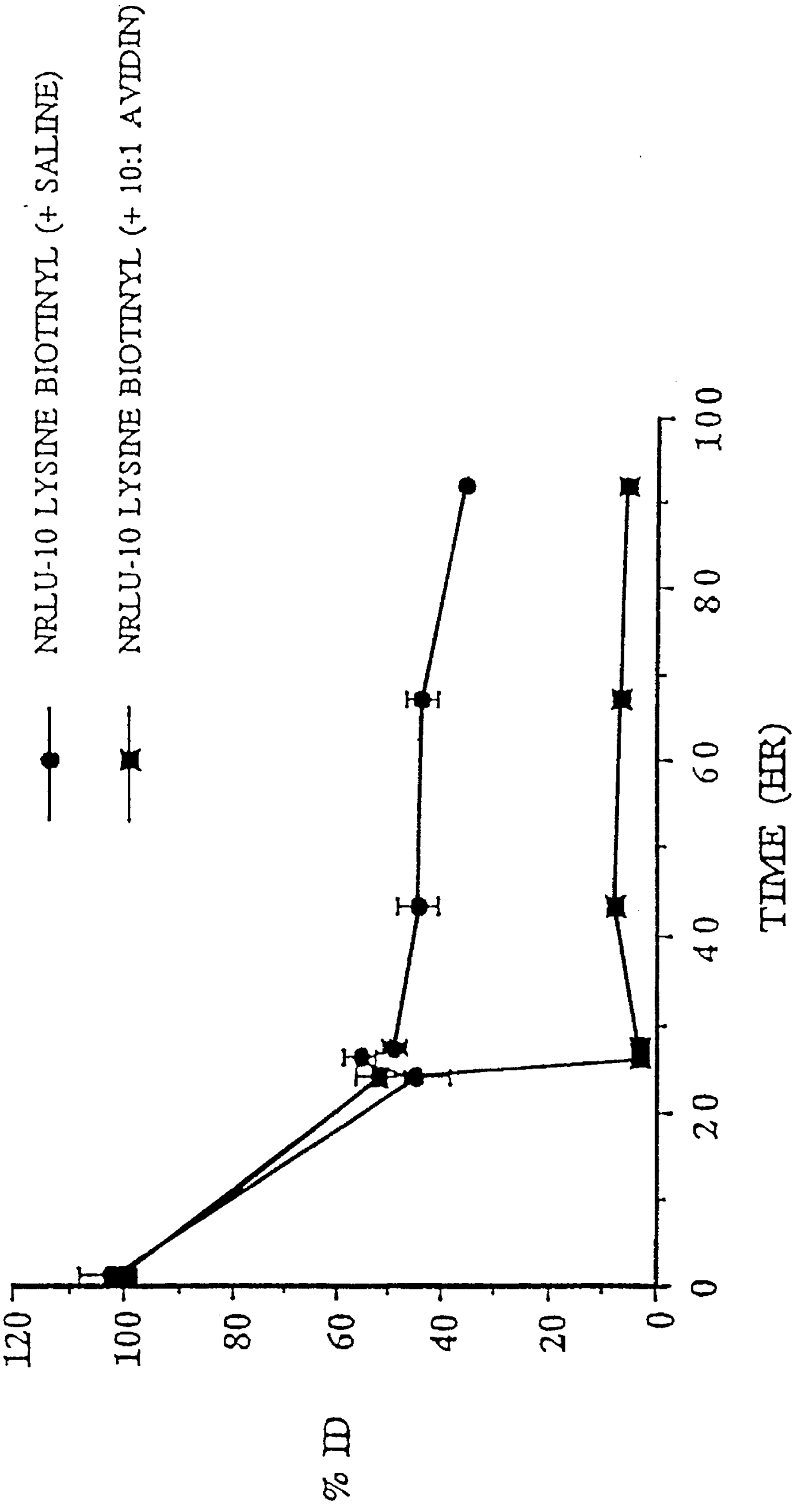
FIG. 1 illustrates blood clearance of biotinylated antibody following intravenous administration of avidin.

Prior to setting forth the invention, it may be helpful to set forth definitions of certain terms to be used within the disclosure.

Targeting moiety: A molecule that binds to a defined population of cells. The targeting moiety may bind a receptor, an oligonucleotide, an enzymatic substrate, an antigenic determinant, or other binding site present on or in the target cell population. Antibody is used throughout the specification as a prototypical example of a targeting moiety. Tumor is used as a prototypical example of a target in describing the present invention.

Ligand/anti-ligand pair: A complementary/anti-complementary set of molecules that demonstrate specific binding, generally of relatively high affinity. Exemplary ligand/anti-ligand pairs include zinc finger protein/dsDNA fragment, enzyme/inhibitor, hapten/antibody, lectin/carbohydrate, ligand/receptor, and biotin/avidin. Biotin/avidin is used throughout the specification as a prototypical example of a ligand/anti-ligand pair.

Anti-ligand: As defined herein, an "anti-ligand" demonstrates high affinity, and preferably, multivalent binding of the complementary ligand. Preferably, the anti-ligand is large enough to avoid rapid renal clearance, and contains sufficient multivalency to accomplish crosslinking and aggregation of targeting moiety-ligand conjugates. Univalent anti-ligands are also contemplated by the present invention. Anti-ligands of the present invention may exhibit or be derivitized to exhibit structural features that direct the uptake thereof, e.g., galactose residues that direct liver uptake. Avidin and streptavidin are used herein as prototypical anti-ligands.

Avidin: As defined herein, "avidin" includes avidin, streptavidin and derivatives and analogs thereof that are capable of high affinity, multivalent or univalent binding of biotin.

Ligand: As defined herein, a "ligand" is a relatively small, soluble molecule that exhibits rapid serum, blood and/or whole body clearance when administered intravenously in an animal or human. Biotin is used as the prototypical ligand.

Active Agent: A diagnostic or therapeutic agent ("the payload"), including radionuclides, drugs, anti-tumor agents, toxins and the like. Radionuclide therapeutic agents are used as prototypical active agents.

$N_xS_y$ Chelates: As defined herein, the term "$N_xS_y$ chelates" includes bifunctional chelators that are capable of (i) coordinately binding a metal or radiometal and (ii) covalently attaching to a targeting moiety, ligand or anti-ligand. Particularly preferred $N_xS_y$ chelates have $N_2S_2$ and $N_3S$ cores. Exemplary $N_xS_y$ chelates are described in Fritzberg et al., *Proc. Natl. Acad. Sci. USA* 85:4024–29, 1988; in Weber et al., *Bioconj. Chem.* 1:431–37, 1990; and in the references cited therein, for instance.

Pretargeting: As defined herein, pretargeting involves target site localization of a targeting moiety that is conjugated with one member of a ligand/anti-ligand pair; after a time period sufficient for optimal target-to-non-target accumulation of this targeting moiety conjugate, active agent conjugated to the opposite member of the ligand/anti-ligand pair is administered and is bound (directly or indirectly) to the targeting moiety conjugate at the target site (two-step pretargeting). Three-step and other related methods described herein are also encompassed.

Clearing Agent: An agent capable of binding, complexing or otherwise associating with an administered moiety (e,g., targeting moiety-ligand, targeting moiety-anti-ligand or anti-ligand alone) present in the recipient's circulation, thereby facilitating circulating moiety clearance from the recipient's body, removal from blood circulation, or inactivation thereof in circulation. The clearing agent is preferably characterized by physical properties, such as size, charge, configuration or a combination thereof, that limit clearing agent access to the population of target cells recognized by a targeting moiety used in the same treatment protocol as the clearing agent.

Target Cell Retention: The amount of time that a radionuclide or other therapeutic agent remains at the target cell surface or within the target cell. Catabolism of conjugates or molecules containing such therapeutic agents appears to be primarily responsible for the loss of target cell retention.

Conjugate: A conjugate encompasses chemical conjugates (covalently or non-covalently bound), fusion proteins and the like.

Permeability Enhancing Moiety: An agent capable of increasing the permeability at a target site characterized by a three dimensional cellular matrix. Exemplary permeability enhancing moieties function by one or more of the following mechanisms: inducing gaps in the endothelium of venules through action on the postcapillary bed; inducing such gaps through action on the entire capillary bed; disrupting cellto-cell associations; mediating target cell inflammatory responses; or the like.

Intercellular Junction: An area of interacting adjacent plasma membranes. Intercellular junctions can be categorized functionally into: (1) adhering junctions that hold cells tightly together (for example, desmosomes); (2) impermeable junctions that hold cells tightly together and prevent leakage of molecules between cells (i.e., tight junctions); and (3) communicating junctions that mediate passage of small molecules between adjacent cells (for instance, gap junctions).

Immunogen: A substance which is capable, under appropriate conditions, of inducing a specific immune response and of reacting with the products of that response (e.g., a specific antibody, specifically sensitized T-lymphocytes or both).

Hapten Immunogen: A specific protein-free substance which has a chemical configuration such that it can interact with specific combining groups on an antibody or with the recognition site on a T-lymphocyte but which, unlike antigenic determinants, does not itself elicit an immune response (e.g., a detectable T-cell response or the formation of a detectable amount of antibody). When coupled with a carrier protein, it does elicit an immune response.

Lymphokine. Soluble protein mediators released by certain lymphocytes, which in turn can regulate other cell-mediated immune functions, such as lymphocyte transformation, macrophage activation or cytotoxicity on other cells.

Mitogen. A substance that induces mitosis and cell transformation, especially lymphocyte transformation.

A recognized disadvantage associated with in vivo administration of targeting moiety-radioisotopic conjugates for imaging or therapy is localization of the attached radioactive agent at both non-target and target sites. Until the administered radiolabeled conjugate clears from the circulation, normal organs and tissues are transitorily exposed to the attached radioactive agent. For instance, radiolabeled whole antibodies that are administered in vivo exhibit relatively slow blood clearance; maximum target site localization generally occurs 1–3 days post-administration. Generally, the longer the clearance time of the conjugate from the circulation, the greater the radioexposure of non-target organs.

These characteristics are particularly problematic with human radioimmunotherapy. In human clinical trials, the long circulating half-life of radioisotope bound to whole antibody causes relatively large doses of radiation to be delivered to the whole body. In particular, the bone marrow, which is very radiosensitive, is the dose-limiting organ of non-specific toxicity.

In order to decrease radioisotope exposure of non-target tissue, potential targeting moieties generally have been screened to identify those that display minimal non-target reactivity, while retaining target specificity and reactivity. By reducing non-target exposure (and adverse non-target localization and/or toxicity), increased doses of a radiotherapeutic conjugate may be administered; moreover, decreased non-target accumulation of a radiodiagnostic conjugate leads to improved contrast between background and target.

Therapeutic drugs, administered alone or as targeted conjugates, are accompanied by similar disadvantages. Again, the goal is administration of the highest possible concentration of drug (to maximize exposure of target tissue), while remaining below the threshold of unacceptable normal organ toxicity (due to non-target, tissue exposure). Unlike radioisotopes, however, therapeutic drugs need to be taken into a target cell to exert a cytotoxic effect. In the case of targeting moiety-therapeutic drug conjugates, it would be advantageous to combine the relative target specificity of a targeting moiety with a means for enhanced target cell internalization of the targeting moiety-drug conjugate.

In contrast, enhanced target cell internalization is disadvantageous if one administers diagnostic agent-targeting moiety conjugates. Internalization of diagnostic conjugates results in cellular catabolism and degradation of the conjugate. Upon degradation, small adducts of the diagnostic agent or the diagnostic agent per se may be released from the cell, thus eliminating the ability to detect the conjugate in a target-specific manner.

One method for reducing non-target tissue exposure to a diagnostic or therapeutic agent involves "pretargeting" the targeting moiety at a target site, and then subsequently administering a rapidly clearing diagnostic or therapeutic agent conjugate that is capable of binding to the "pretargeted" targeting moiety at the target site. A description of some embodiments of the pretargeting technique may be found in U.S. Pat. No. 4,863,713 (Goodwin et al.).

A typical pretargeting approach ("three-step") is schematically depicted below.

1)
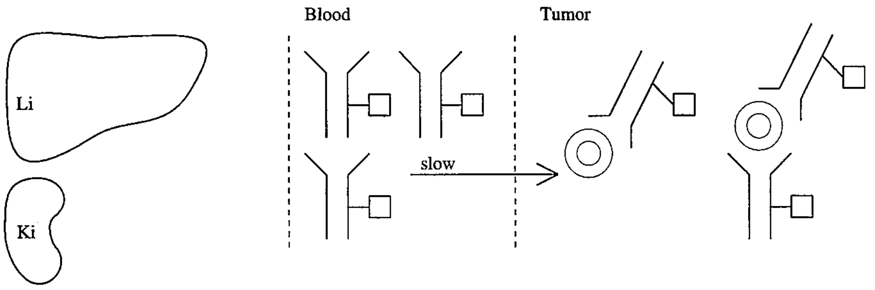

-continued

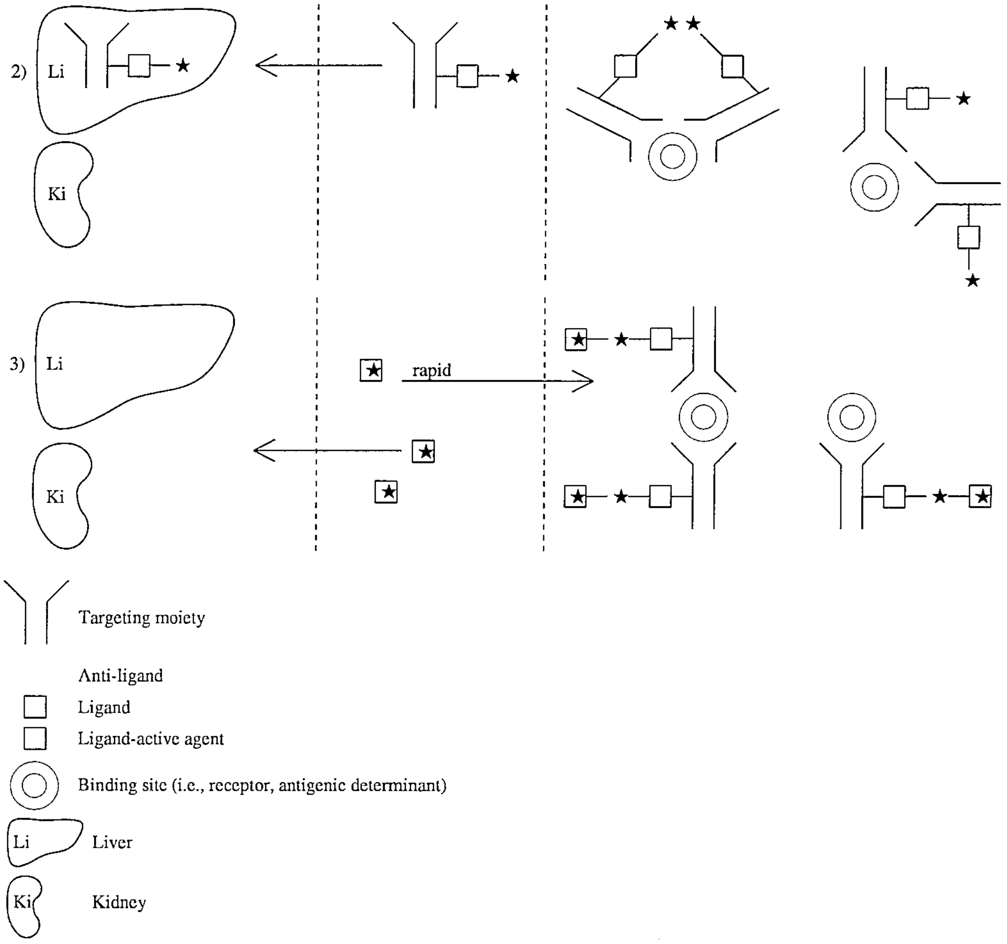

Briefly, this three-step pretargeting protocol features administration of an antibody-ligand conjugate, which is allowed to localize at a target site and to dilute in the circulation. Subsequently administered anti-ligand binds to the antibody-ligand conjugate and clears unbound antibody-ligand conjugate from the blood. Preferred anti-ligands are large and contain sufficient multivalency to accomplish crosslinking and aggregation of circulating antibody-ligand conjugates. The clearing by anti-ligand is probably attributable to anti-ligand crosslinking and/or aggregation of antibody-ligand conjugates that are circulating in the blood, which leads to complex/aggregate clearance by the recipient's RES (reticuloendothelial system). Anti-ligand clearance of this type is preferably accomplished with a multivalent molecule; however, a univalent molecule of sufficient size to be cleared by the RES on its own could also be employed. Alternatively, receptor-based clearance mechanisms, e.g., Ashwell receptor hexose, e.g., galactose, mannose or the like, residue recognition mechanisms, may be responsible for anti-ligand clearance. Such clearance mechanisms are less dependent upon the valency of the anti-ligand with respect to the ligand than the RES complex/aggregate clearance mechanisms. It is preferred that the ligand-anti-ligand pair displays relatively high affinity binding.

A diagnostic or therapeutic agent-ligand conjugate that exhibits rapid whole body clearance is then administered. When the circulation brings the active agent-ligand conjugate in proximity to the target cell-bound antibody-ligand-anti-ligand complex, anti-ligand binds the circulating active agent-ligand conjugate and produces an antibody-ligand: anti-ligand: ligand-active agent "sandwich" at the target site. Because the diagnostic or therapeutic agent is attached to a rapidly clearing ligand (rather than antibody, antibody fragment or other slowly clearing targeting moiety), this technique promises decreased non-target exposure to the active agent.

Alternate pretargeting methods eliminate the step of parenterally administering an anti-ligand clearing agent. These "two-step" procedures feature targeting moiety-ligand or targeting moiety-anti-ligand administration, followed by administration of active agent conjugated to the opposite member of the ligand-anti-ligand pair. As an optional step "1.5" in the two-step pretargeting methods of the present invention, a clearing agent (preferably other than ligand or anti-ligand alone) is administered to facilitate the clearance of circulating targeting moiety-containing conjugate.

In the two-step pretargeting approach, the clearing agent preferably does not become bound to the target cell population, either directly or through the previously administered and target cell bound targeting moiety-anti-ligand or targeting moiety-ligand conjugate. An example of two-step pretargeting involves the use of biotinylated human transferrin as a clearing agent for avidin-targeting moiety conjugate, wherein the size of the clearing agent results in liver clearance of transferrin-biotin-circulating avidin-targeting moiety complexes and substantially precludes association with the avidin-targeting moiety conjugates bound at target cell sites. (See, Goodwin, D. A., *Antibod. Immunoconj. Radiopharm.*, 4:427–34, 1991).

The two-step pretargeting approach overcomes certain disadvantages associated with the use of a clearing agent in a three-step pretargeted protocol. More specifically, data obtained in animal models demonstrate that in vivo anti-ligand binding to a pretargeted targeting moiety-ligand conjugate (i.e., the cell-bound conjugate) removes the targeting moiety-ligand conjugate from the target cell. One explanation for the observed phenomenon is that the multivalent anti-ligand crosslinks targeting moiety-ligand conjugates on the cell surface, thereby initiating or facilitating internalization, of the resultant complex. The apparent loss of targeting moiety-ligand from the cell might result from internal degradation of the conjugate and/or release of active agent from the conjugate (either at the cell surface or intracellularly). An alternative explanation for the observed phenomenon is that permeability changes in the target cell's membrane allow increased passive diffusion of any molecule into the target cell. Also, some loss of targeting moiety-ligand may result from alteration in the affinity by subsequent binding of another moiety to the targeting moiety-ligand, e.g., anti-idiotype monoclonal antibody binding causes removal of tumor bound monoclonal antibody.

The present invention recognizes that this phenomenon (apparent loss of the targeting moiety-ligand from the target cell) may be used to advantage with regard to in vivo delivery of therapeutic agents generally, or to drug delivery in particular. For instance, a targeting moiety may be covalently linked to both ligand and therapeutic agent and administered to a recipient. Subsequent administration of anti-ligand crosslinks targeting moiety-ligand-therapeutic agent tripartite conjugates bound at the surface, inducing internalization of the tripartite conjugate (and thus the active agent). Alternatively, targeting moiety-ligand may be delivered to the target cell surface, followed by administration of anti-ligand-therapeutic agent.

In one aspect of the present invention, a targeting moiety-anti-ligand conjugate is administered in vivo; upon target localization of the targeting moiety-anti-ligand conjugate (i.e., and clearance of this conjugate from the circulation), an active agent-ligand conjugate is parenterally administered. This method enhances retention of the targeting moiety-anti-ligand: ligand-active agent complex at the target cell (as compared with targeting moiety-ligand: anti-ligand: ligand-active agent complexes and targeting moiety-ligand: anti-ligand-active agent complexes). Although a variety of ligand/anti-ligand pairs may be suitable for use within the claimed invention, a preferred ligand/anti-ligand pair is biotin/avidin.

In a second aspect of the invention, radioiodinated biotin and related methods are disclosed. Previously, radioiodinated biotin derivatives were of high molecular weight and were difficult to characterize. The radioiodinated biotin described herein is a low molecular weight compound that has been easily and well characterized.

In a third aspect of the invention, a targeting moiety-ligand conjugate is administered in vivo; upon target localization of the targeting moiety-ligand conjugate (i.e., and clearance of this conjugate from the circulation), a drug-anti-ligand conjugate is parenterally administered. This two-step method not only provides pretargeting of the targeting moiety conjugate, but also induces internalization of the subsequent targeting moiety-ligand-anti-ligand-drug complex within the target cell. Alternatively, another embodiment provides a three-step protocol that produces a targeting moiety-ligand: anti-ligand: ligand-drug complex at the surface, wherein the ligand-drug conjugate is administered simultaneously or within a short period of time after administration of anti-ligand (i.e., before the targeting moiety-ligand-anti-ligand complex has been removed from the target cell surface). Additional internalization methodologies are contemplated by the present invention and are discussed herein.

In a fourth aspect of the invention, methods for radiolabeling biotin with technetium-99m, rhenium-186 and rhenium-188 are disclosed. Previously, biotin derivatives were radiolabeled with indium-111 for use in pretargeted immunoscintigraphy (for instance, Virzi et al., *Nucl. Med. Biol.* 18:719–26, 1991; Kalofonos et al., *J. Nucl. Med.* 31: 1791–96, 1990; Paganelli et al., *Canc. Res.* 51:5960–66, 1991). However, $^{99m}$Tc is a particularly preferred radionuclide for immunoscintigraphy due to (i) low cost, (ii) convenient supply and (iii) favorable nuclear properties. Rhenium-186 displays chelating chemistry very similar to $^{99m}$Tc, and is considered to be an excellent therapeutic radionuclide (i.e., a 3.7 day half-life and 1.07 MeV maximum particle that is similar to $^{131}$I). Therefore, the claimed methods for technetium and rhenium radiolabeling of biotin provide numerous advantages.

The present invention is also directed to radiolabeling with yttrium-90, lutetium-177, sumarium-153, and other appropriate +3 metals. Y-90 is a particularly preferred radionuclide for therapy, because it exhibits favorable nuclear properties including high specific activity, long path length with respect to deposition of radiation in tissue, high equilibrium dose constant and favorable half-life properties. More specifically, the beta emission of Y-90 ($Beta_{av}$=0.937 MeV) is one of the most energetic of all beta emitters. The $X_{90}$ value of Y-90 is 5.34 mm (i.e., 90% of the energy emitted from a point source is absorbed in a sphere of 5.34 mm radius). Y-90 has a high equilibrium dose constant or mean energy/nuclear transition, Delta=1.99 Rad-gram/microcurie-hour, and a 64 hour half-life suitable for targeted therapy. Y-90 can be manufactured at high specific activity and is available as a generator product. Specific advantages of Y-90 are (1) that it has the capability to kill neighboring target cells not directly targeted by the pretargeted targeting moiety-ligand or targeting moiety-anti-ligand conjugate and (2) that more radiation is deposited per microcurie localized than for other beta emitters of lower mean particle energy (provided that a sufficiently large target volume is available).

Lu-177 is a particularly preferred radionuclide for targeted nuclide therapy, since it has a moderately energetic beta emission ($Beta_{av}$=0.140 MeV); it is available in high specific activity; its radiochemical production is efficient; it emits two gammas of ideal energy and abundance for imaging (208 keV, 11% and 113 keV, 7%); and it has a relatively long half-life (161 hours). The $X_{90}$ for Lu-177 is 0.31 mm, i.e., 90% of the energy emitted form a point source is absorbed in a sphere of radius 0.31 mm. Lu-177 has an equilibrium dose constant or mean energy/nuclear transition of 0.31 Rad-gram/microcuries-hour and an adequate half-life to serve as a targeted therapeutic radionuclide. Specific advantages of Lu-177 are (1) that its emitted energy is efficiently absorbed in smaller targeted tumor volumes such as metastatic tumor foci or involved lymph nodes and (2) that its long physical half-life makes optimal use of the tumor retention property of the pretargeting delivery method.

The "targeting moiety" of the present invention binds to a defined target cell population, such as tumor cells. Preferred targeting moieties useful in this regard include antibody and antibody fragments, peptides, and hormones.

Proteins corresponding to known cell surface receptors (including low density lipoproteins, transferrin and insulin), fibrinolytic enzymes, anti-HER2, platelet binding proteins such as annexins, and biological response modifiers (including interleukin, interferon, erythropoietin and colony-stimulating factor) are also preferred targeting moieties. Also, anti-EGF receptor antibodies, which internalize following binding to the receptor and traffic to the nucleus to an extent, are preferred targeting moieties for use in the present invention to facilitate delivery of Auger emitters and nucleus binding drugs to target cell nuclei. Oligonucleotides, e,g., antisense oligonucleotides that are complementary to portions of target cell nucleic acids (DNA or RNA), are also useful as targeting moieties in the practice of the present invention. Oligonucleotides binding to cell surfaces are also useful. Analogs of the above-listed targeting moieties that retain the capacity to bind to a defined target cell population may also be used within the claimed invention. In addition, synthetic targeting moieties may be designed.

Functional equivalents of the aforementioned molecules are also useful as targeting moieties of the present invention. One targeting moiety functional equivalent is a "mimetic" compound, an organic chemical construct designed to mimic the proper configuration and/or orientation for targeting moiety-target cell binding. Another targeting moiety functional equivalent is a short polypeptide designated as a "minimal" polypeptide, constructed using computer-assisted molecular modeling and mutants having altered binding affinity, which minimal polypeptides exhibit the binding affinity of the targeting moiety.

Preferred targeting moieties of the present invention are antibodies (polyclonal or monoclonal), peptides, oligonucleotides or the like. Polyclonal antibodies useful in the practice of the present invention are polyclonal (Vial and Callahan, *Univ. Mich. Med. Bull.*, 50: 284–6, 1956), affinity-purified polyclonal or fragments thereof (Chao et al., *Res, Comm. in Chem. Path. & Pharm.*, 9:749–61, 1974).

Monoclonal antibodies useful in the practice of the present invention include whole antibody and fragments thereof. Such monoclonal antibodies and fragments are producible in accordance with conventional techniques, such as hybridoma synthesis, recombinant DNA techniques and protein synthesis. Useful monoclonal antibodies and fragments may be derived from any species (including humans) or may be formed as chimeric proteins which employ sequences from more than one species. See, generally, Kohler and Milstein, *Nature*, 256: 495–97, 1975; *Eur. J. Immunol.*, 6: 511–19, 1976.

Human monoclonal antibodies or "humanized" murine antibody are also useful as targeting moieties in accordance with the present invention. For example, murine monoclonal antibody may be "humanized" by genetically recombining the nucleotide sequence encoding the murine Fv region (i.e., containing the antigen binding sites) or the complementarity determining regions thereof with the nucleotide sequence encoding a human constant domain region and an Fc region, e.g., in a manner similar to that disclosed in European Patent Application No. 0,411,893 A2. Some murine residues may also be retained within the human variable region framework domains to ensure proper target site binding characteristics. Humanized targeting moieties are recognized to decrease the immunoreactivity of the antibody or polypeptide in the host recipient, permitting an increase in the half-life and a reduction in the possibility of adverse immune reactions.

Another preferred targeting moiety of the present invention are annexins and other platelet binding proteins, such as PAP-1 (Placental Anticoagulant Protein or Annexin V). Annexins are (with the exception of annexin II) single chain, non-glycosylated proteins of approximately 36 kilodaltons. Annexins possess a number of biological properties based on the principle of calcium ion binding. Investigations have shown that annexins bind with high affinity to membrane lipids in the presence of micromolar quantities of calcium. In the presence of calcium, these proteins have an especially high affinity for negatively charged phospholipids such as phosphatidylserine or phosphatidylinosine.

Annexins exert anti-coagulatory effects. In a manner analogous to anti-inflammatory mechanisms, coagulation inhibition is mediated by the binding of annexins to negatively charged surface phospholipids (i.e., to platelets) which binding blocks the activation of clotting factors by such negatively charged surface phospholipids. Annexins localize to target sites rapidly, i.e., in a matter of minutes, but remains circulating in the serum for a longer time period.

As a result of these properties, annexins may be employed in two-step or three-step pretargeting protocols for the diagnosis of blood clots or the treatment of blood clots associated with indications, such as DVT (deep vein thrombosis), PE (pulmonary embolism), heart attack, stroke and the like. Exemplary diagnostic and treatment protocols employing the two-step pretargeting approach are set forth below to further elucidate this aspect of the present invention.

For the visualization of blood clots associated with a number of pathological conditions, a chemical conjugate or a fusion protein of annexin with avidin or streptavidin is administered to a recipient for whom such a diagnosis is desired. The annexin portion of the conjugate localizes rapidly to target sites characterized by negatively charged surface phospholipids, such as blood clots. As a consequence of the rapid target site uptake, a clearing agent, such as those discussed herein, may be administered after the passage of a short time (ranging from about 5 minutes to about 1 hour, with within about 15 minutes preferred). The clearing agent serves to rapidly diminish the serum level of the annexin-anti-ligand conjugate. Next, biotin labeled with an imaging radionuclide, such as Tc-99m for example, is administered. Biotin directs the localization of the administered moiety to the previously localized annexin-anti-ligand. Non-target bound radiolabeled biotin is rapidly cleared from the recipient. Consequently, imaging of the target sites proceeds with minimal exposure of non-target sites to radioactivity. This approach offers the advantages of speed, facilitating imaging of difficult target sites such as lung clots, and improved clot to blood ratios.

For therapeutic applications involving blood clots associated with a number of pathological conditions, a chemical conjugate or a fusion protein of annexin with avidin or streptavidin is administered to a recipient for whom such treatment is desired. A clearing agent, such as those discussed herein, may be administered after the passage of a short time (ranging from about 5 minutes to about 1 hour, with within about 15 minutes preferred) to diminish the serum level of the annexin-anti-ligand conjugate. Biotin conjugated with therapeutic agents, such as fibrolytic agents, tissue plasminogen activator, thrombolytic agents (e.g., streptokinase, anisoylated plasminogen streptokinase activator complex) and the like, are deliverable in this manner. Such a dosing regimen may be repeated, for example, once daily for a number of weeks to address the recipient's physiological condition. Consequently, delivery of a therapeutic agent to target sites proceeds with minimal exposure of non-target sites to that agent.

An example of an annexin useful in the practice of the present invention is Annexin V which was isolated by Bohn in 1979 from human placenta, a rich source of annexins, and termed Placenta Protein 4 (PP4). Annexin V consists of four domains, with each made up of five alpha helices wherein the alpha helices serve as connecting elements between the domains. From the side, the molecule appears crown-like with five calcium binding sites on its convex surface, through which annexin-phospholipid interactions are mediated. Other annexins having the characteristics described above are also useful in the practice of the present invention. Annexin V has been expressed in *E. coli.*

Types of active agents (diagnostic or therapeutic) useful herein include toxins, anti-tumor agents, drugs and radionuclides. Several of the potent toxins useful within the present invention consist of an A and a B chain. The A chain is the cytotoxic portion and the B chain is the receptor-binding portion of the intact toxin molecule (holotoxin). Because toxin B chain may mediate non-target cell binding, it is often advantageous to conjugate only the toxin A chain to a targeting moiety. However, while elimination of the toxin B chain decreases non-specific cytotoxicity, it also generally leads to decreased potency of the toxin A chain-targeting protein conjugate, as compared to the corresponding holotoxin-targeting moiety conjugate.

Preferred toxins in this regard include holotoxins, such as abrin, ricin, modeccin, Pseudomonas exotoxin A, Diphtheria toxin, pertussis toxin and Shiga toxin; and A chain or "A chain-like" molecules, such as ricin A chain, abrin A chain, modeccin A chain, the enzymatic portion of Pseudomonas exotoxin A, Diphtheria toxin A chain, the enzymatic portion of pertussis toxin, the enzymatic portion of Shiga toxin, gelonin, pokeweed antiviral protein, saporin, tritin, barley toxin and snake venom peptides. Ribosomal inactivating proteins (RIPs), naturally occurring protein synthesis inhibitors that lack translocating and cell-binding ability, are also suitable for use herein.

Preferred drugs suitable for use herein include conventional chemotherapeutics, such as vinblastine, doxorubicin, bleomycin, methotrexate, 5-fluorouracil, 6-thioguanine, cytarabine, cyclophosphamide and cisplatinum, as well as other conventional chemotherapeutics as described in *Cancer: Principles and Practice of Oncology*, 2d ed., V. T. DeVita, Jr., S. Hellman, S. A. Rosenberg, J. B. Lippincott Co., Philadelphia, Pa., 1985, Chapter 14. A particularly preferred drug within the present invention is a trichothecene.

Trichothecenes are drugs produced by soil fungi of the class *Fungi imperfecti* or isolated from *Baccharus megapotamica* (Bamburg, J. R. *Proc. Molec. Subcell. Biol.* 8:41–110, 1983; Jarvis & Mazzola, *Acc. Chem. Res.* 15:338–395, 1982). They appear to be the most toxic molecules that contain only carbon, hydrogen and oxygen (Tamm, C. *Fortschr. Chem. Org. Naturst.* 31:61–117, 1974). They are all reported to act at the level of the ribosome as inhibitors of protein synthesis at the initiation, elongation, or termination phases.

There are two broad classes of trichothecenes: those that have only a central sesquiterpenoid structure and those that have an additional macrocyclic ring (simple and macrocyclic trichothecenes, respectively). The simple trichothecenes may be subdivided into three groups (i.e., Group A, B, and C) as described in U.S. Pat. Nos. 4,744,981 and 4,906,452 (incorporated herein by reference). Representative examples of Group A simple trichothecenes include: Scirpene, Roridin C, dihydrotrichothecene, Scirpen-4, 8-diol, Verrucarol, Scirpentriol, T-2 tetraol, pentahydroxyscirpene, 4-deacetylneosolaniol, trichodermin, deacetylcalonectrin, calonectrin, diacetylverrucarol, 4-monoacetoxyscirpenol, 4,15-diacetoxyscirpenol, 7-hydroxydiacetoxyscirpenol, 8-hydroxydiacetoxy-scirpenol (Neosolaniol), 7,8-dihydroxydiacetoxyscirpenol, 7-hydroxy-8-acetyldiacetoxyscirpenol, 8-acetylneosolaniol, NT-1, NT-2, HT-2, T-2, and acetyl T-2 toxin. Representative examples of Group B simple trichothecenes include: Trichothecolone, Trichothecin, deoxynivalenol, 3-acetyldeoxynivalenol, 5-acetyldeoxynivalenol, 3,15-diacetyldeoxynivalenol, Nivalenol, 4-acetylnivalenol (Fusarenon-X), 4,15-idacetylnivalenol, 4,7,15-triacetylnivalenol, and tetra-acetylnivalenol. Representative examples of Group C simple trichothecenes include: Crotocol and Crotocin. Representative macrocyclic trichothecenes include Verrucarin A, Verrucarin B, Verrucarin J (Satratoxin C), Roridin A, Roridin D, Roridin E (Satratoxin D), Roridin H, Satratoxin F, Satratoxin G, Satratoxin H, Vertisporin, Mytoxin A, Mytoxin C, Mytoxin B, Myrotoxin A, Myrotoxin B, Myrotoxin C, Myrotoxin D, Roritoxin A, Roritoxin B, and Roritoxin D. In addition, the general "trichothecene" sesquiterpenoid ring structure is also present in compounds termed "baccharins" isolated from the higher plant *Baccharis megapotamica*, and these are described in the literature, for instance as disclosed by Jarvis et al. (Chemistry of Alleopathy, ACS Symposium Series No. 268: ed. A. C. Thompson, 1984, pp. 149–159).

Experimental drugs, such as mercaptopurine, N-methylformamide, 2-amino-1,3,4-thiadiazole, melphalan, hexamethylmelamine, gallium nitrate, 3% thymidine, dichloromethotrexate, mitoguazone, suramin, bromodeoxyuridine, iododeoxyuridine, semustine, 1-(2-chloroethyl)-3-(2,6-dioxo-3-piperidyl)-1-nitrosourea, N,N'-hexamethylene-bis-acetamide, azacitidine, dibromodulcitol, Erwinia asparaginase, ifosfamide, 2-mercaptoethane sulfonate, teniposide, taxol, 3-deazauridine, soluble Baker's antifol, homoharringtonine, cyclocytidine, acivicin, ICRF-187, spiromustine, levamisole, chlorozotocin, aziridinyl benzoquinone, spirogermanium, aclarubicin, pentostatin, PALA, carboplatin, amsacrine, caracemide, iproplatin, misonidazole, dihydro-5-azacytidine, 4'-deoxy-doxorubicin, menogaril, triciribine phosphate, fazarabine, tiazofurin, teroxirone, ethiofos, N-(2-hydroxyethyl)-2-nitro-1H-imidazole-1-acetamide, mitoxantrone, acodazole, amonafide, fludarabine phosphate, pibenzimol, didemnin B, merbarone, dihydrolenperone, flavone-8-acetic acid, oxantrazole, ipomeanol, trimetrexate, deoxyspergualin, echinomycin, and dideoxycytidine (See *NCI Investigational Drugs, Pharmaceutical Data* 1987, NIH Publication No. 88–2141, Revised November 1987) are also preferred.

Radionuclides useful within the present invention include gamma-emitters, positron-emitters, Auger electron-emitters, X-ray emitters and fluorescence-emitters, with beta- or alpha-emitters preferred for therapeutic use. Radionuclides are well-known in the art and include $^{123}I$, $^{125}I$, $^{130}I$, $^{131}I$, $^{133}I$, $^{135}I$, $^{47}Sc$, $^{72}As$, $^{72}Se$, $^{90}Y$, $^{88}Y$, $^{97}Ru$, $^{100}Pd$, $^{101m}Rh$, $^{119}Sb$, $^{128}Ba$, $^{197}Hg$, $^{211}At$, $^{212}Bi$, $^{153}Sm$, $^{169}Eu$, $^{212}pb$, $^{109}Pd$, $^{111}In$, $^{67}Ga$, $^{68}Ga$, $^{67}Cu$, $^{75}Br$, $^{76}Br$, $^{77}Br$, $^{99m}Tc$, $^{11}C$, $^{13}N$, $^{15}O$ and $^{18}F$. Preferred therapeutic radionuclides include $^{188}Re$, $^{186}Re$, $^{203}Pb$, $^{212}Pb$, $^{212}Bi$, $^{109}Pd$, $^{64}Cu$, $^{67}Cu$, $^{90}Y$, $^{125}I$, $^{131}I$, $^{77}Br$, $^{211}At$, $^{97}Ru$, $^{105}Rh$, $^{198}Au$ and $^{199}Ag$ or $^{177}Lu$.

Other anti-tumor agents are administrable in accordance with the present invention. Exemplary anti-tumor agent$_s$ include cytokines, such as IL-2, tumor necrosis factor or the like, lectin inflammatory response promoters (selectins), such as L-selectin, E-selectin, P-selectin or the like, and like molecules.

Ligands suitable for use within the present invention include biotin, haptens, lectins, epitopes, dsDNA fragments, enzyme inhibitors and analogs and derivatives thereof. Useful complementary anti-ligands include avidin (for biotin), carbohydrates (for lectins), antibody, fragments or analogs thereof, including mimetics (for haptens and epitopes) and zinc finger proteins (for dsDNA fragments) and enzymes (for enzyme inhibitors). Preferred ligands and anti-ligands bind to each other with an affinity of at least about $k_D \geqq 10^{-9}$M.

As mentioned above, zinc finger protein/dsDNA is a ligand-anti-ligand binding pair contemplated by the present invention. Zinc finger proteins are a class of proteins containing repeating subunits of approximately 30 amino acids that bind to specific promoter regions on dsDNA and aid in transcription. These proteins are also capable of binding to dsRNA with unknown function. Like antibodies, zinc finger proteins are a family of proteins consisting of variable and conserved regions. Zinc finger proteins, as a class, contain from about 2 to about 39 repeating subunits (fingers), with each such finger capable of binding specific nucleotide sequences. Each finger is capable of binding to a "cleft" in the conformation of the dsDNA/RNA structure that is dependent upon nucleotide sequence. The present inventors hypothesize that greater numbers of subunits correspond to greater affinity and specificity. In addition, zinc is incorporated into the proteins within each subunit and is important in maintaining proper conformation for dsDNA binding.

To illustrate the use of the zinc finger protein/dsDNA binding pair in pretargeting protocols, a two-step approach is described below. This ligand-anti-ligand binding pair may also be used in three-step pretargeting protocols of the present invention. For two-step pretargeting, a zinc finger protein or a dsDNA fragment is conjugated to a targeting moiety in any convenient manner therefor, including, for example, conjugation methods described herein.

Several methods have been developed to conjugate DNA or oligonucleotides to proteins. One simple method is oxidation of the sugar moiety of the DNA. The resultant aldehyde groups are available for reaction with amines on the protein. The amines generated by such reactions are then reduced by reaction with a reducing agent such as $NaCNBH_4$ to form the more stable amine bonds.

Another protein-oligonucleotide conjugation method involves initial oxidation of the sugar residue on DNA using an oxidizing agent such as $NaIO_4$. The dialdehyde formed is treated with 5-pyridylcystamine hydrochloride and $NaCNBH_3$. This dithiopyridine derivative can then be reacted with tributylphosphine to generate the thiol adduct. Reaction of the free thiol-bearing DNA adduct with a maleimide-derivatized protein results in a thioether oligonucleotide-protein conjugate. See, for example, Kuijpers et al., "Specific Recognition of Antibody-Oligonucleotide Conjugates by Radiolabeled Antisense Nucleotides: A Novel Approach for Two-Step Radioimmunotherapy of Cancer, " *Bioconjugate Chem.*, 4: 94–102 (1993).

The conjugates are administered to a recipient by a route chosen in view of the patient's physical condition and known or anticipated illness. Following target site localization of the administered conjugate (or clearing agent treatment as described herein), administration of the other member of the ligand pair conjugated to a therapeutic agent (e.g., radionuclide, drug or anti-tumor agent) is undertaken. The administered therapeutic agent-containing conjugate binds to the previously localized targeting agent containing conjugate. Therapeutic agent-containing conjugate that does not bind at the target site will be eliminated from the recipient's body at a much more rapid rate than a monoclonal antibody-therapeutic agent conjugate would be removed. Moreover, such therapeutic agent-containing conjugates can be chemically altered for more rapid excretion, if necessary, to reduce non-target exposure to the therapeutic agent.

A schematic of the administered components and ultimate in vivo formed "sandwich" for a monoclonal antibody-zinc finger protein/dsDNA-therapeutic agent two-step pretargeting protocol are shown below.

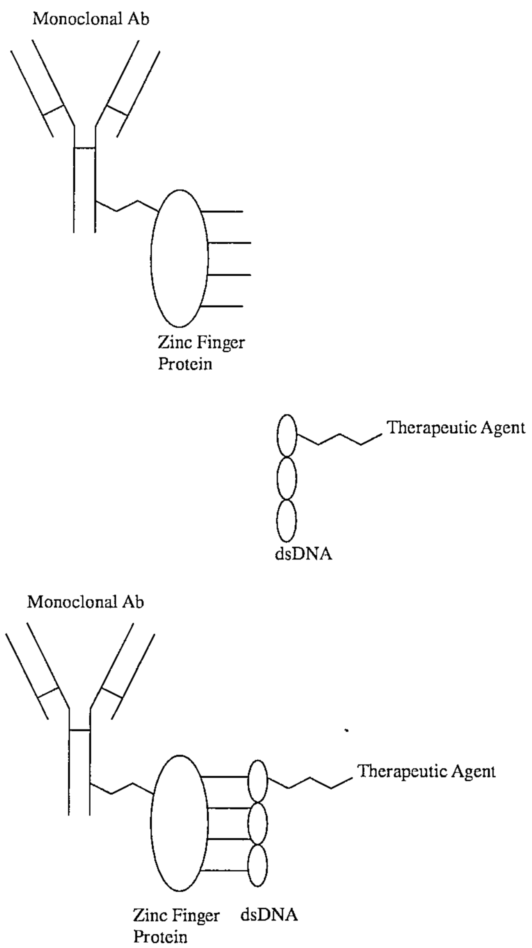

Use of the zinc finger protein/dsDNA fragment ligand/anti-ligand binding pair offers advantages with respect to immunogenicity. The targeting agent used in a pretargeting protocol may be human or humanized, and all of the other administered components (exclusive of the therapeutic agent) are human in origin. An additional advantage of this approach is that zinc finger proteins can be engineered to accommodate specific, high affinity interactions with synthetic or cloned dsDNA fragments, thereby eliminating non-specific interactions of the administered components with normal tissue.

One embodiment of this aspect of the present invention involves the use of pretargeting approaches to target double stranded DNA itself. Such protocols of the present invention are useful, for example, for gene therapy, delivery of tumor suppressire DNA, deleted genes and the like. More specifically, a targeting moiety-zinc finger protein is pretargeted to a target site. Subsequently, a dsDNA fragment that is complementary to the zinc finger protein is injected and allowed to bind to the localized zinc finger protein. Because zinc finger protein-DNA interaction is a normal cell physiologic mechanism, DNA will be delivered free of encumbering chemistry to the cellular milieu. The dsDNA is then internalized by the target cell via the normal mechanisms therefor, i.e, via endocytosis or the like.

One component to be administered in a preferred two-step pretargeting protocol involving the biotin-avidin ligand-anti-ligand system is a targeting moiety-avidin or a targeting moiety-streptavidin conjugate. The preferred targeting moiety useful in these embodiments of the present invention is a monoclonal antibody. Protein-protein conjugations are generally problematic due to the formation of undesirable byproducts, including high molecular weight and cross-linked species, however. A non-covalent synthesis technique involving reaction of biotinylated antibody with streptavidin has been reported to result in substantial by product formation. Also, at least one of the four biotin binding sites on the streptavidin is used to link the antibody and streptavidin, while another such binding site may be sterically unavailable for biotin binding due to the configuration of the streptavidin-antibody conjugate.

Thus, covalent streptavidin-antibody conjugation is preferred, but high molecular weight byproducts are often obtained. The degree of crosslinking and aggregate formation is dependent upon several factors, including the level of protein derivitization using heterobifunctional crosslinking reagents. Sheldon et al., *Appl. Radiat. Isot.* 43: 1399–1402, 1992, discuss preparation of covalent thioether conjugates by reacting succinimidyl 4-(N-maleimidomethyl)cyclohexane-1-carboxylate (SMCC)-derivitized antibody and iminothiolane-derivitized streptavidin.

Streptavidin-proteinaceous targeting moiety conjugates are preferably prepared as described in Example XI below, with the preparation involving the steps of: preparation of SMCC-derivitized streptavidin; preparation of DTT-reduced proteinaceous targeting moiety; conjugation of the two prepared moieties; and purification of the monosubstituted conjugate. The purified fraction is preferably further characterized by one or more of the following techniques: HPLC size exclusion, SDS-PAGE, immunoreactivity, biotin binding capacity and in vivo studies.

Alternatively, thioether conjugates useful in the practice of the present invention may be formed using other thiolating agents, such as SPDP, iminothiolate, SATA or the like, or other thio-reactive heterobifunctional cross linkers, such as m-maleimidobenzoyl-N-hydroxysuccinimide ester, N-succinimidyl(4-iodoacetyl)aminobenzoate or the like.

Streptavidin-proteinaceous targeting moiety conjugates of the present invention can also be formed by conjugation of a lysine epsilon amino group of one protein with a maleimide-derivitized form of the other protein. For example, at pH 8–10, lysine epsilon amino moieties react with protein maleimides, prepared, for instance, by treatment of the protein with SMCC, to generate stable amine covalent conjugates. In addition, conjugates can be prepared by reaction of lysine epsilon amino moieties of one protein with aldehyde functionalities of the other protein. The resultant imine bond is reducible to generate the corresponding stable amine bond. Aldehyde functionalities may be generated, for example, by oxidation of protein sugar residues or by reaction with aldehyde-containing heterobifunctional cross linkers.

Another method of forming streptavidin-targeting moiety conjugates involves immobilized iminobiotin that binds SMCC-derivitized streptavidin. In this conjugation/purification method, the reversible binding character of iminobiotin (immobilized) to streptavidin is exploited to readily separate conjugate from the unreacted targeting moiety. Iminobiotin binding can be reversed under conditions of lower pH and elevated ionic strength, e,g., $NH_2OAc$, pH 4 (50 mM) with 0.5M NaCl.

For streptavidin, for example, the conjugation/purification proceeds as follows:

- SMCC-derivitized streptavidin is bound to immobilized iminobiotin (Pierce Chemical Co., St. Louis, Mo.), preferably in column format;
- a molar excess (with respect to streptavidin) of DTT-reduced antibody (preferably free of reductant) is added to the nitrogen-purged, phosphate-buffered iminobiotin column wherein the SMCC-streptavidin is bound (DTT-reduced antibody will saturate the bound SMCC-streptavidin, and unbound reduced antibody passing through the column can be reused);
- the column is washed free of excess antibody; and
- a buffer that lowers the pH and increases ionic strength is added to the column to elute streptavidin-antibody conjugate in pure form.

As indicated above, targeting moiety-mediated ligand-anti-ligand pretargeting involves the localization of either targeting moiety-ligand or targeting moiety-anti-ligand at target tissue. Often, peak uptake to such target tissue is achieved before the circulating level of targeting moiety-containing conjugate in the blood is sufficiently low to permit the attainment of an optimal target-to-non-target conjugate ratio. To obviate this problem, two approaches are useful. The first approach allows the targeting moiety-containing conjugate to clear from the blood by "natural" or endogenous clearance mechanisms. This method is complicated by variations in systemic clearance of proteins and by endogenous ligand or anti-ligand. For example, endogenous biotin may interfere with the preservation of biotin binding sites on a streptavidin-targeting moiety conjugate.

The second approach for improving targeting moiety-ligand or targeting moiety-anti-ligand conjugate target-to-blood ratio "chases" the conjugate from the circulation through in vivo complexation of conjugate with a molecule constituting or containing the complementary anti-ligand or ligand. When biotinylated antibodies are used as a ligand-targeting moiety conjugate, for example, avidin forms relatively large aggregated species upon complexation with the circulating biotinylated antibody, which aggregated species are rapidly cleared from the blood by the RES uptake. See, for example, U.S. Pat. No. 4,863,713. One problem with this method, however, is the potential for cross-linking and internalizing tumor-bound biotinylated antibody by avidin.

When avidin-targeting moiety conjugates are employed, poly-biotinylated transferrin has been used to form relatively large aggregated species that are cleared by RES uptake. See for example, Goodwin, *J. Nucl. Med.* 33 (10) :1816–18, 1992). Poly-biotinylated transferrin also has the potential for cross-linking and internalizing tumor-bound avidinylated-targeting moiety, however. In addition, both "chase" methodologies involve the prolonged presence of aggregated moieties of intermediate, rather than large, size (which are not cleared as quickly as large size particles by RES uptake), thereby resulting in serum retention of subsequently administered ligand-active agent or anti-ligand-active agent. Such serum retention unfavorably impacts the target cell-to-blood targeting ratio.

The present invention provides clearing agents of protein and non-protein composition having physical properties facilitating use for in vivo complexation and blood clearance of anti-ligand/ligand (e.g., avidin/biotin)-targeting moiety (e.g., antibody) conjugates. These clearing agents are useful in improving the target:blood ratio of targeting moiety conjugate. Other applications of these clearing agents include lesional imaging or therapy involving blood clots and the like, employing antibody-active agent delivery modalities. For example, efficacious anti-clotting agent provides rapid target localization and high target:non-target targeting ratio. Active agents administered in pretargeting protocols of the present invention using efficient clearing agents are targeted in the desirable manner and are, therefore, useful in the imaging/therapy of conditions such as pulmonary embolism and deep vein thrombosis.

Clearing agents useful in the practice of the present invention preferably exhibit one or more of the following characteristics:

rapid, efficient complexation with targeting moiety-ligand (or anti-ligand) conjugate in vivo;

rapid clearance from the blood of targeting moiety conjugate capable of binding a subsequently administered complementary anti-ligand or ligand containing molecule;

high capacity for clearing (or inactivating) large amounts of targeting moiety conjugate; and low immunogenicity.

Preferred clearing agents include hexose-based and non-hexose based moieties. Hexose-based clearing agents are molecules that have been derivatized to incorporate one or more hexoses (six carbon sugar moieties) recognized by Ashwell receptors. Exemplary of such hexoses are galactose, mannose and the like. Galactose is the prototypical clearing agent hexose derivative for the purposes of this description. Thus, galactose-based and non-galactose based molecules are discussed below.

Protein-type galactose-based clearing agents include proteins having endogenous exposed galactose residues or which have been derivitized to expose or incorporate such galactose residues. Exposed galactose residues direct the clearing agent to rapid clearance by endocytosis into the liver through specific receptors therefor (Ashwell receptors). These receptors bind the clearing agent, and induce endocytosis into the hepatocyte, leading to fusion with a lysosome and recycle of the receptor back to the cell surface. This clearance mechanism is characterized by high efficiency, high capacity and rapid kinetics.

An exemplary clearing agent of the protein-based/galactose-bearing variety is the asialoorosomucoid derivative of human alpha-1 acid glycoprotein (orosomucoid, molecular weight=41,000 Dal, isoelectric point=1.8–2.7). The rapid clearance from the blood of asialoorosomucoid has been documented by Galli, et al., *J. of Nucl. Med. Allied Sci.* 32(2): 110–16, 1988.

Treatment of orosomucoid with neuraminidase removes sialic acid residues, thereby exposing galactose residues. Other such derivitized clearing agents include, for example, galactosylated albumin, galactosylated-IgM, galactosylated-IgG, asialohaptoglobin, asialofetuin, asialoceruloplasmin and the like.

Human serum albumin (HSA), for example, may be employed in a clearing agent of the present invention as follows:

$$(\text{Hexose})_m\text{—Human Serum Albumin (HSA)—}(\text{Ligand})_n,$$

wherein n is an integer from 1 to about 10 and m is an integer from 1 to about 25 and wherein the hexose is recognized by Ashwell receptors.

In a preferred embodiment of the present invention the ligand is biotin and the hexose is galactose. More preferably, HSA is derivatized with from 10–20 galactose residues and 1–5 biotin residues. Still more preferably, HSA clearing agents of the present invention are derivatized with from about 12 to about 15 galactoses and 3 biotins. Derivatization with both galactose and biotin are conducted in a manner sufficient to produce individual clearing agent molecules with a range of biotinylation levels that averages a recited whole number, such as 1, biotin. Derivatization with 3 biotins, for example, produces a product mixture made up of individual clearing agent molecules, substantially all of which having at least one biotin residue. Derivatization with 1 biotin produces a clearing agent product mixture, wherein a significant portion of the individual molecules are not biotin derivatized. The whole numbers used in this description refer to the average biotinylation of the clearing agents under discussion.

In addition, clearing agents based upon human proteins, especially human serum proteins such as, for example, orosomucoid and human serum albumin, are less immunogenic upon administration into the serum of a human recipient. Another advantage of using asialoorosomucoid is that human orosomucoid is commercially available from, for example, Sigma Chemical Co, St. Louis, Mo.

One way to prevent clearing agent compromise of target-bound conjugate through direct complexation is through use of a clearing agent of a size sufficient to render the clearing agent less capable of diffusion into the extravascular space and binding to target-associated conjugate. This strategy is useful alone or in combination with the aforementioned recognition that exposed galactose residues direct rapid liver uptake. This size-exclusion strategy enhances the effectiveness of non-galactose-based clearing agents of the present invention. The combination (exposed galactose and size) strategy improves the effectiveness of "protein-type" or "polymer-type" galactose-based clearing agents.

Galactose-based clearing agents include galactosylated, biotinylated proteins (to remove circulating streptavidin-targeting moiety conjugates, for example) of intermediate molecular weight (ranging from about 40,000 to about 200,000 Dal), such as biotinylated asialoorosomucoid, galactosyl-biotinyl-human serum albumin or other galactosylated and biotinylated derivatives of non-immunogenic soluble natural proteins, as well as biotin- and galactose-derivitized polyglutamate, polylysine, polyarginine, polyaspartate and the like. High molecular weight moieties (ranging from about 200,000 to about 1,000,000 Dal) characterized by poor target access, including galactosyl-biotinyl-IgM or -IgG (approximately 150,000 Dal) molecules, as well as galactose- and biotin-derivitized transferrin conjugates of human serum albumin, IgG and IgM molecules and the like, can also be used as clearing agents of the claimed invention. Chemically modified polymers of intermediate or high molecular weight (ranging from about 40,000 to about 1,000,000 Dal), such as galactose- and biotin-derivitized dextran, hydroxypropylmethacrylamide polymers, polyvinylpyrrolidone-polystyrene copolymers, divinyl ether-maleic acid copolymers, pyran copolymers, or PEG, also have utility as clearing agents in the practice of the present invention. In addition, rapidly clearing biotinylated liposomes (high molecular weight moieties with poor target access) can be derivitized with galactose and biotin to produce clearing agents for use in the practice of the present invention.

A further class of clearing agents useful in the present invention involve small molecules (ranging from about 500 to about 10,000 Dal) derivitized with galactose and biotin that are sufficiently polar to be confined to the vascular space as an in vivo volume of distribution. More specifically, these agents exhibit a highly charged structure and, as a result, are not readily distributed into the extravascular volume, because they do not readily diffuse across the lipid membranes lining the vasculature. Exemplary of such clearing agents are mono- or poly-biotin-derivitized 6,6'-[(3,3'-dimethyl[1,1'-biphenyl]-4,4'-diyl)bis(azo) bis[4-amino-5-hydroxy-1,3-naphthalene disulfonic acid]tetrasodium salt, mono- or poly-biotinyl-galactose-derivitized polysulfated dextran-biotin, mono- or poly-biotinyl-galactose-derivitized dextran-biotin and the like.

The galactose-exposed or -derivitized clearing agents are preferably capable of (1) rapidly and efficiently complexing with the relevant ligand- or anti-ligand-containing conjugates via ligand-anti-ligand affinity; and (2) clearing such complexes from the blood via the galactose receptor, a liver specific degradation system, as opposed to aggregating into complexes that are taken up by the generalized RES system, including the lung and spleen. Additionally, the rapid kinetics of galactose-mediated liver uptake, coupled with the affinity of the ligand-anti-ligand interaction, allow the use of intermediate or even low molecular weight carriers.

Non-galactose residue-bearing moieties of low or intermediate molecular weight (ranging from about 40,000 to about 200,000 Dal) localized in the blood may equilibrate with the extravascular space and, therefore, bind directly to target-associated conjugate, compromising target localization. In addition, aggregation-mediated clearance mechanisms operating through the RES system are accomplished using a large stoichiometric excess of clearing agent. In contrast, the rapid blood clearance of galactose-based clearing agents used in the present invention prevents equilibration, and the high affinity ligand-anti-ligand binding allows the use of low stoichiometric amounts of such galactose-based clearing agents. This feature further diminishes the potential for galactose-based clearing agents to compromise target-associated conjugate, because the absolute amount of such clearing agent administered is decreased.

Clearing agent evaluation experimentation involving galactose- and biotin-derivatized clearing agents of the present invention is detailed in Example XXII. Specific clearing agents of the present invention that were examined during the Example XXII experimentation are (1) asialoorosomucoid-biotin, (2) human serum albumin derivatized with galactose and biotin, and (3) a 70,000 dalton molecular weight dextran derivatized with both biotin and galactose. The experimentation showed that proteins and polymers are derivatizabie to contain both galactose and biotin and that the resultant derivatized molecule is effective in removing circulating streptavidin-protein conjugate from the serum of the recipient. Biotin loading was varied to determine the effects on both clearing the blood pool of circulating avidin-containing conjugate and the ability to deliver a subsequently administered biotinylated isotope to a target site recognized by the streptavidin-containing conjugate. The effect of relative doses of the administered components with respect to clearing agent efficacy was also examined.

Protein-type and polymer-type non-galactose-based clearing agents include the agents described above, absent galactose exposure or derivitization and the like. These clearing agents act through an aggregation-mediated RES mechanism. In these embodiments of the present invention, the clearing agent used will be selected on the basis of the target organ to which access of the clearing agent is to be excluded. For example, high molecular weight (ranging from about 200,000 to about 1,000,000 Dal) clearing agents will be used when tumor targets or clot targets are involved.

Another class of clearing agents includes agents that do not remove circulating ligand or anti-ligand/targeting moiety conjugates, but instead "inactivate" the circulating conjugates by blocking the relevant anti-ligand or ligand binding sites thereon. These "cap-type" clearing agents are preferably small (500 to 10,000 Dal) highly charged molecules, which exhibit physical characteristics that dictate a volume of distribution equal to that of the plasma compartment (i.e., do not extravasate into the extravascular fluid volume). Exemplary cap-type clearing agents are poly-biotin-derivitized 6,6'-[(3,3'-dimethyl[1,1'-biphenyl]-4,4'-diyl)bis(azo) bis[4-amino-5-hydroxy-1,3-naphthalene disulfonic acid]tetrasodium salt, poly-biotinyl-derivitized polysulfated dextran-biotin, mono- or poly-biotinyl-derivitized dextran-biotin and the like.

Cap-type clearing agents are derivitized with the relevant anti-ligand or ligand, and then administered to a recipient of previously administered ligand/or anti-ligand/targeting moiety conjugate. Clearing agent-conjugate binding therefore diminishes the ability of circulating conjugate to bind any subsequently administered active agent-ligand or active agent-anti-ligand conjugate. The ablation of active agent binding capacity of the circulating conjugate increases the efficiency of active agent delivery to the target, and increases the ratio of target-bound active agent to circulating active agent by preventing the coupling of long-circulating serum protein kinetics with the active agent. Also, confinement of the clearing agent to the plasma compartment prevents compromise of target-associated ligand or anti-ligand.

Clearing agents of the present invention may be administered in single or multiple doses. A single dose of biotinylated clearing agent, for example, produces a rapid decrease in the level of circulating targeting moiety-streptavidin, followed by a small increase in that level, presumably caused, at least in part, by re-equilibration of targeting moiety-streptavidin within the recipient's physiological compartments. A second or additional clearing agent doses may then be employed to provide supplemental clearance of targeting moiety-streptavidin. Alternatively, clearing agent may be infused intravenously for a time period sufficient to clear targeting moiety-streptavidin in a continuous manner.

Other types of clearing agents and clearance systems are also useful in the practice of the present invention to remove circulating targeting moiety-ligand or -anti-ligand conjugate from the recipient's circulation. Particulate-based clearing agents, for example, are discussed in Example IX. In addition, extracorporeal clearance systems are discussed in Example IX. In vivo clearance protocols employing arterially inserted proteinaceous or polymeric multiloop devices are also described in Example IX.

One embodiment of the present invention in which rapid acting clearing agents are useful is in the delivery of Auger emitters, such as I-125, I-123, Er-165, Sb-119, Hg-197, Ru-97, T1-201 and Br-77, or nucleus-binding drugs to target cell nuclei. In these embodiments of the present invention, targeting moieties that localize to internalizing receptors on target cell surfaces are employed to deliver a targeting moiety-containing conjugate (i.e., a targeting moiety-anti-ligand conjugate in the preferred two-step protocol) to the target cell population. Such internalizing receptors include EGF receptors, transferrin receptors, HER2 receptors, IL-2 receptors, other interleukins and cluster differentiation receptors, somatostatin receptors, other peptide binding receptors and the like.

After the passage of a time period sufficient to achieve localization of the conjugate to target cells, but insufficient to induce internalization of such targeted conjugates by those cells through a receptor-mediated event, a rapidly acting clearing agent is administered. In a preferred two-step protocol, an active agent-containing ligand or anti-ligand conjugate, such as a biotin-Auger emitter or a biotin-nucleus acting drug, is administered as soon as the clearing agent has been given an opportunity to complex with circulating targeting moiety-containing conjugate, with the time lag between clearing agent and active agent administration being less than about 24 hours. In this manner, active agent is readily internalized through target cell receptor-mediated internalization. While circulating Auger emitters are thought to be non-toxic, the rapid, specific targeting afforded by the pretargeting protocols of the present invention increases the potential of shorter half-life Auger emitters, such as I-123, which is available and capable of stable binding.

The 1,4,7,10-tetraazacyclododecane-N,N',N'',N'''-tetra acetic acid (DOTA)-biotin conjugate (DOTA)-LC-biotin) depicted below has been reported to have desirable in vivo biodistribution and is cleared primarily by renal excretion.

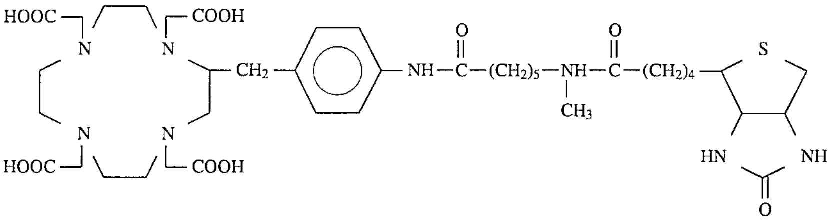

DOTA may also be conjugated to other ligands or to anti-ligands in the practice of the present invention.

Because DOTA strongly binds Y-90 and other radionuclides, it has been proposed for use in radioimmunotherapy. For therapy, it is very important that the radionuclide be stably bound within the DOTA chelate and that the DOTA chelate be stably attached to biotin. Only radiolabeled DOTA-biotin conjugates exhibiting those two characteristics are useful to deliver radionuclides to the targets. Release of the radionuclide from the DOTA chelate or cleavage of the biotin and DOTA conjugate components in serum or at non-target sites renders the conjugate unsuitable for use in therapy.

Serum stability of DOTA-LC-biotin (where LC refers to the "long chain" linker, including an aminocaproyl spacer between the biotin and the DOTA conjugate components) shown above, while reported in the literature to be good, has proven to be problematic. Experimentation has revealed that DOTA-LC-biotin is rapidly cleared from the blood and excreted into the urine as fragments, wherein the biotinamide bond rather than the DOTA-amide bond has been cleaved, as shown below.

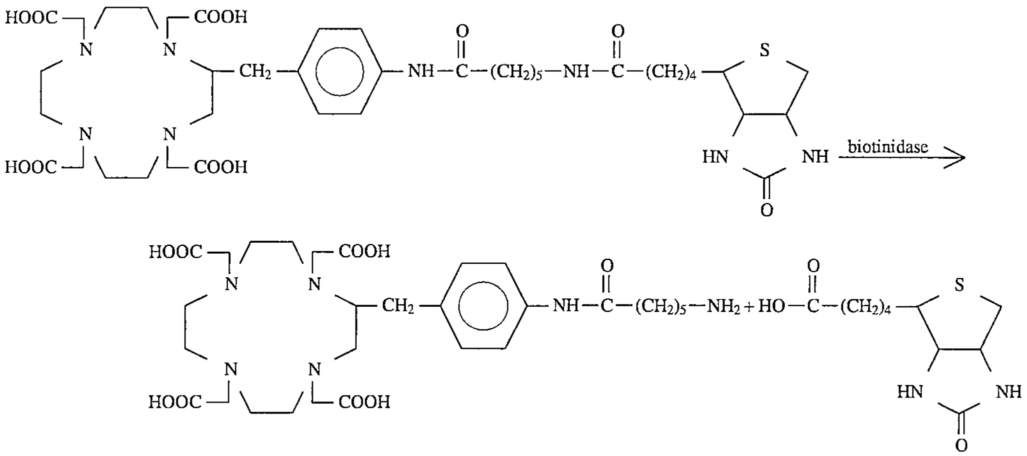

Additional experimentation employing PIP-biocytin conjugates produced parallel results as shown below.

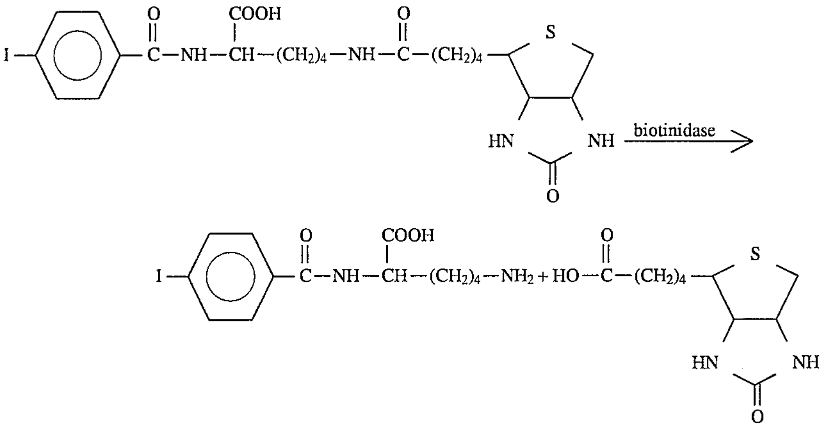

Cleavage of the benzamide was not observed as evidenced by the absence of detectable quantities of iodobenzoic acid in the serum.

It appears that the cleavage results from the action of serum biotinidase. Biotinidase is a hydrolyric enzyme that catalyzes the cleavage of biotin from biotinyl peptides. See, for example, Evangelatos, et al., "Biotinidase Radioassay Using an I-125-Biotin Derivative, Avidin, and Polyethylene Glycol Reagents," *Analytical Biochemistry,* 196: 385–89, 1991.

Drug-biotin conjugates which structurally resemble biotinyl peptides are potential substrates for cleavage by plasma biotinidase. Poor in vivo stability therefore limits the use of drug-biotin conjugates in therapeutic applications. The use of peptide surrogates to overcome poor stability of peptide therapeutic agents has been an area of intense research effort. See, for example, Spatola, Peptide Backbone Modification: A Structure-Activity Analysis of Peptide Containing Amide Bond Surrogates, "*Chemistry and Biochemistry of Amino Acids, Peptides and Proteins,*" vol. 7, Weinstein, ed., Marcel Dekker, New York, 1983; and Kim et al., "A New Peptide Bond Surrogate: 2-Isoxazoline in Pseudodipeptide Chemistry," *Tetrahedron Letters,* 45: 6811–14, 1991.

Elimination of the aminocaproyl spacer of DOTA-LC-biotin gives DOTA-SC-biotin (where the SC indicates the "short chain" linker between the DOTA and biotin conjugate components), which molecule is shown below:

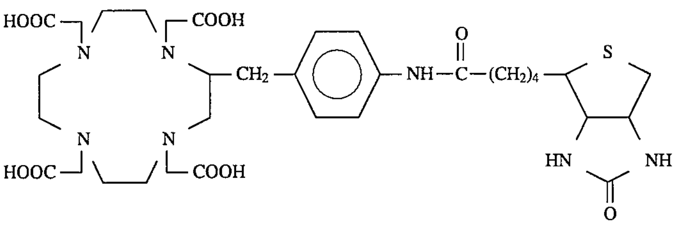

DOTA-SC-biotin exhibits significantly improved serum stability in comparison to DOTA-LC-biotin. This result does not appear to be explainable on the basis of biotinidase activity alone. The experimentation leading to this conclusion is summarized in the Table set forth below.

Time Dependent Cleavage of DOTA-Biotin Conjugates

| Time at 37° C. | % Avidin Binding PIP-Biocytin | Y-90-LC DOTA-Biotin | Y-90-SC DOTA-Biotin |
|---|---|---|---|
| 5 Minutes | 75% | 50% | — |
| 15 Minutes | 57% | 14% | — |
| 30 Minutes | 31% | 12% | — |
| 60 Minutes | — | 0% | 98% |
| 20 Hours | — | 0% | 60% |

where "—" indicates that the value was not measured.

The difference in serum stability between DOTA-LC-biotin and DOTA-SC-biotin might be explained by the fact that the SC derivative contains an aromatic amide linkage in contrast to the aliphatic amide linkage of the LC derivative, with the aliphatic amide linkage being more readily recognized by enzymes as a substrate therefor. This argument cannot apply to biotinidase, however, because biotinidase very efficiently cleaves aromatic amides. In fact, it is recognized that the simplest and most commonly employed biotinidase activity measuring method uses N-(d-biotinyl)-4-aminobenzoate (BPABA) as a substrate, with the hydrolysis of BPABA resulting in the liberation of biotin and 4-aminobenzoate (PABA). See, for example, B. Wolf, et al., "Methods in Enzymology," pp. 103–111, Academic Press Inc., 1990. Consequently, one would predict that DOTA-SC-biotin, like its LC counterpart, would be a biotinidase substrate. Since DOTA-SC-biotin exhibits serum stability, biotinidase activity alone does not adequately explain why some conjugates are serum stable while others are not. A series of DOTA-biotin conjugates was therefore synthesized by the present inventors to determine which structural features conferred serum stability to the conjugates.

Some general strategies for improving serum stability of peptides with respect to enzymatic action are the following:

incorporation of D-amino acids, N-methyl amino acids and alpha-substituted amino acids.

In vivo stable biotin-DOTA conjugates are useful within the practice of the present invention. In vivo stability imparts the following advantages:

1) increased tumor uptake in that more of the radioisotope will be targeted to the previously localized targeting moiety-streptavidin; and
2) increased tumor retention, if biotin is more stably bound to the radioisotope. In addition, the linkage between DOTA and biotin may also have a significant impact on biodistribution (including normal organ uptake, target uptake and the like) and pharmacokinetics.

The strategy for design of the DOTA-containing molecules and conjugates of the present invention involved three primary considerations:

1) in vivo stability (including biotinidase and general peptidase activity resistance), with an initial cut of 100% stability for 1 hour;
2) renal excretion; and
3) ease of synthesis.

The DOTA-biotin conjugates of the present invention reflect the implementation of one or more of the following strategies:

1) substitution of the carbon adjacent to the cleavage susceptible amide nitrogen;
2) alkylation of the cleavage susceptible amide nitrogen;
3) substitution of the amide carbonyl with an alkyl amino group;
4) incorporation of D-amino acids as well as analogs or derivatives thereof; or
5) incorporation of thiourea linkages.

DOTA-biotin conjugates in accordance with the present invention may be generally characterized as follows: conjugates that retain the biotin carboxy group in the structure thereof and those that do not (i.e., the terminal carboxy group of biotin has been reduced or otherwise chemically modified. Structures of such conjugates represented by the following general formula have been devised:

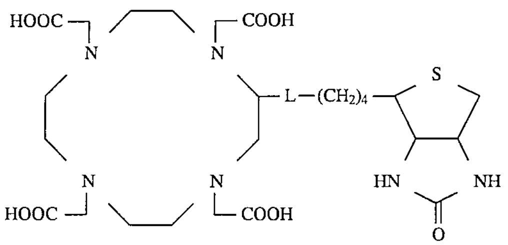

wherein L may alternatively be substituted in one of the following ways on one of the $—CH_2—COOH$ branches of the DOTA structure: $—CH(L)—COOH$ or $—CH_2COOL$ or $—CH_2COL$). When these alternative structures are employed, the portion of the linker bearing the functional group for binding with the DOTA conjugate component is selected for the capability to interact with either the carbon or the carboxy in the branch portions of the DOTA structure, with the serum stability conferring portion of the linker structure being selected as described below.

In the case where the linkage is formed on the core of the DOTA structure as shown above, L is selected according to the following principles, with the portion of the linker designed to bind to the DOTA conjugate component selected for the capability to bind to an amine.

A. One embodiment of the present invention includes linkers incorporating a D-amino acid spacer between a DOTA aniline amine and the biotin carboxy group shown above. Substituted amino acids are preferred for these embodiments of the present invention, because alpha-substitution also confers enzymatic cleavage resistance. Exemplary L moieties of this embodiment of the present invention may be represented as follows:

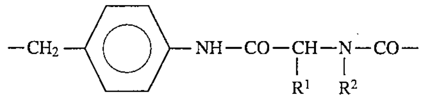

where $R^1$ is selected from lower alkyl, lower alkyl substituted with hydrophilic groups (preferably, $(CH_2)_n—OH$ $(CH_2)_n—OSO_3$, $(CH_2)_n—SO_3$,

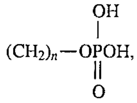

where n is 1 or 2), glucuronide-substituted amino acids or other glucuronide derivatives; and $R^2$ is selected from hydrogen, lower alkyl, substituted lower alkyl (e.g., hydroxy, sulfate, phosphonate or a hydropholic moiety (preferably OH).

For the purposes of the present disclosure, the term "lower alkyl" indicates an alkyl group with from one to five carbon atoms. Also, the term "substituted" includes one or several substituent groups, with a single substituent group preferred.

Preferred L groups of this embodiment of the present invention include the following:

$R^1=CH_3$ and $R^2=H$ (a D-alanine derivative, with a synthetic scheme therefor shown in Example XXI);

$R^1=CH_3$ and $R^2=CH_3$ (an N-methyl-D-alanine derivative);

$R^1=CH_2—OH$ and $R^2=H$ (a D-serine derivative);

$R^1=CH_2OSO_3$ and $R^2=H$ (a D-serine-O-sulfate-derivative); and

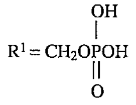

and $R^2=H$ (a D-serine-O-phosphonate-derivative);

Other preferred moieties of this embodiment of the present invention include molecules wherein $R^1$ is hydrogen and $R^2=—(CH_2)_nOH$ or a sulfate or phosphonate derivative thereof and n is 1 or 2 as well as molecules wherein $R^1$ is

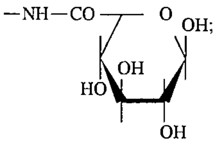 ; or $—(CH_2)_5—NH_2$; or

-continued

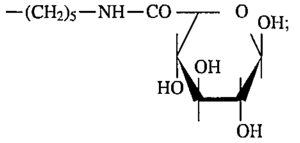

or when $R^2$=H.

Preferred moieties incorporating the glucuronide of D-lysine and the glucuronide of amino pimelate are shown below as I and II, respectively.

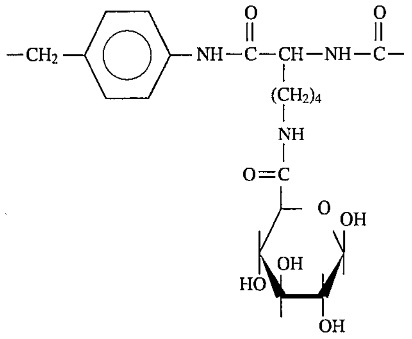

I

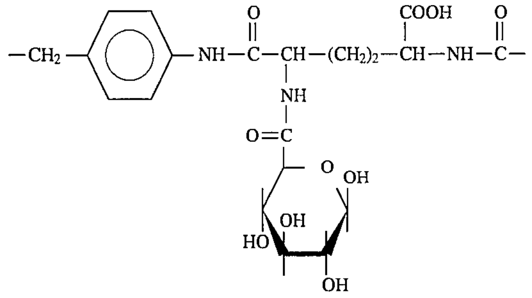

II

A particularly preferred linker of this embodiment of the present invention is the D-alanine derivative set forth above.

B. Linkers incorporating alkyl substitution on one or more amide nitrogen atoms are also encompassed by the present invention, with some embodiments of such linkers preparable from L-amino acids. Amide bonds having a substituted amine moiety are less susceptible to enzymatic cleavage. Such linkers exhibit the following general formula:

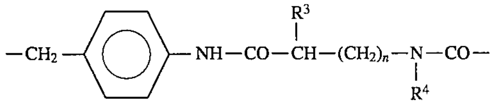

where $R^4$ is selected from hydrogen, lower alkyl, lower alkyl substituted with hydroxy, sulfate, phosphonate or the like and

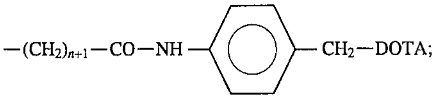

$R_3$ is selected from hydrogen; an amine; lower alkyl; an amino- or a hydroxy-, sulfate- or phosphonate-substituted lower alkyl; a glucuronide or a glucuronide-derivatized amino groups; and n ranges from 0–4.

Preferred linkers of this embodiment of the present invention include:

$R^3$=H and $R^4$=$CH_3$ when n=4, synthesizable as discussed in Example XXI;

$R^3$=H and $R^4$=$CH_3$ when n=0, synthesizable from N-methyl-glycine (having a trivial name of sarcosine) as described in Example XXI;

$R^3$=$NH_2$ and $R^4$=$CH_3$, when n=0;

$R^3$=H and

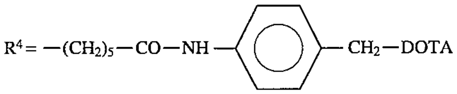

when n=4 (Bis-DOTA-LC-biotin), synthesizable from bromohexanoic acid as discussed in Example XXI; and $R^3$=H and

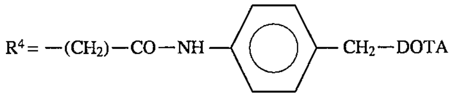

when n=0 (bis-DOTA-SC-biotin), synthesizable from iminodiacetic acid.

The synthesis of a conjugate including a linker wherein $R^3$ is H and $R^4$ is $-CH_2CH_2OH$ and n is 0 is also described in Example XXI. Schematically, the synthesis of a conjugate of this embodiment of the present invention wherein n is 0, $R^3$ is H and $R^4$ is $-CH_2-COOH$ is shown below.

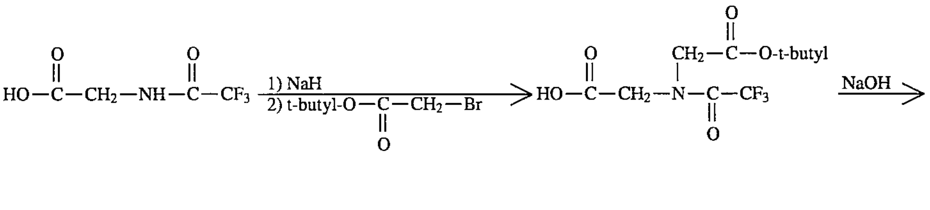

-continued

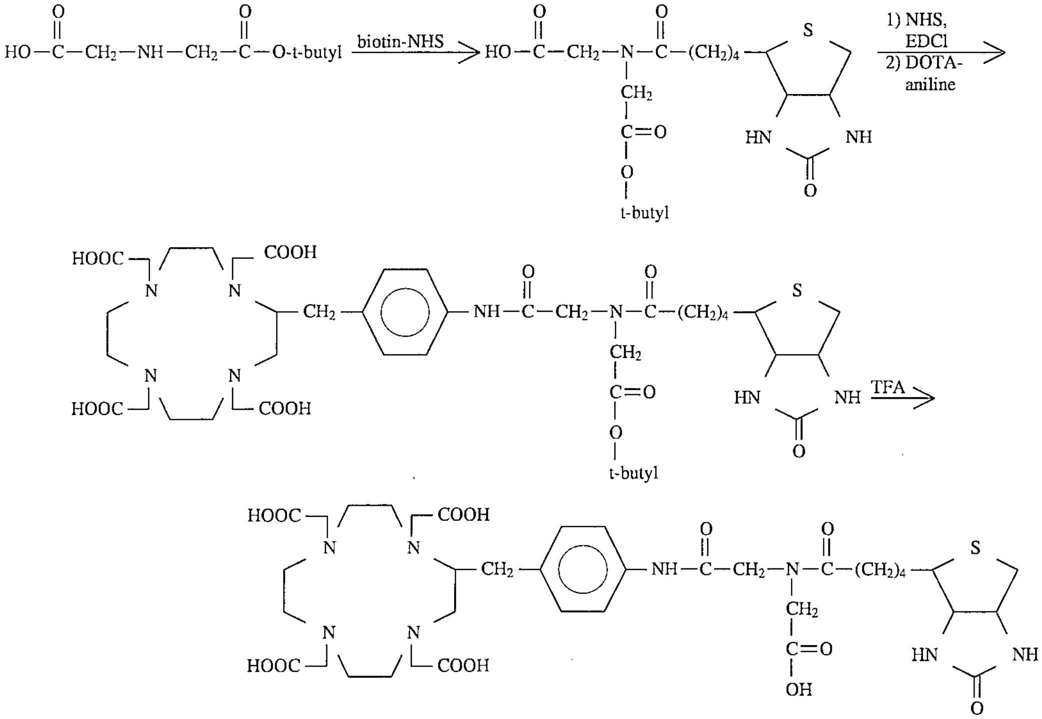

Bis-DOTA-LC-biotin, for example, offers the following advantages:

1) incorporation of two DOTA molecules on one biotin moiety increases the overall hydrophilicity of the biotin conjugate and thereby directs in vivo distribution to urinary excretion; and
2) substitution of the amide nitrogen adjacent to the biotin carboxyl group blocks peptide and/or biotinidase cleavage at that site.

Bis-DOTA-LC-biotin, the glycine-based linker and the N-methylated linker where $R^3$=H, $R^4$=$CH_3$, n=4 are particularly preferred linkers of this embodiment of the present invention.

C. Another linker embodiment incorporates a thiourea moiety therein. Exemplary thiourea adducts of the present invention exhibit the following general formula:

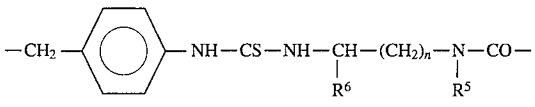

where $R^5$ is selected from hydrogen or lower alkyl;

$R^6$ is selected from H and a hydrophilic moiety; and n ranges from 0–4.

Preferred linkers of this embodiment of the present invention are as follows:

$R^5$=H and $R^6$=H when n=5;

$R^5$=H and $R^6$=COOH when n=5; and $R^5$=$CH_3$ and $R^6$=COOH when n=5.

The second preferred linker recited above can be prepared using either L-lysine or D-lysine. Similarly, the third preferred linker can be prepared using either N-methyl-D-lysine or N-methyl-L-lysine.

Another thiourea adduct of minimized lipophilicity is

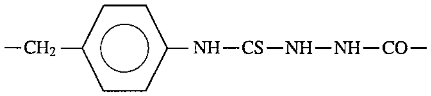

which may be formed via the addition of biotinhydrazide (commercially available from Sigma Chemical Co., St. Louis, Mo.) and DOTA-benzylisothiocyanate (a known compound synthesized in one step from DOTA-aniline), with the thiourea-containing compound formed as shown below.

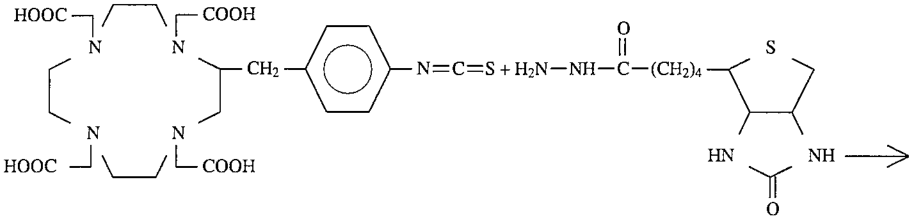

-continued

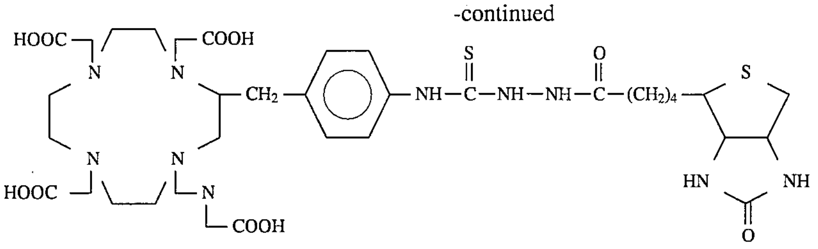

D. Amino acid-derived linkers of the present invention with substitution of the carbon adjacent to the cleavage susceptible amide have the general formula set forth below:

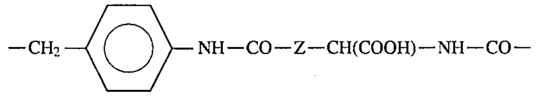

wherein

Z is $—(CH_2)_2—$, conveniently synthesized form glutamic acid; or

Z=$—CH_2—S—CH_2—$, synthesizable from cysteine and iodo-acetic acid; or

Z=$—CH_2—$, conveniently synthesized form aspartic acid; or

Z=$—(CH_2)_n—CO—O—CH_2—$, where n ranges from 1–4 and which is synthesizable from serine.

E. Another exemplary linker embodiment of the present invention has the general formula set forth below:

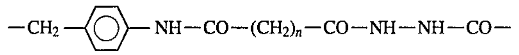

n ranges from 1–5.

F. Another embodiment involves disulfide-containing linkers, which provide a metabolically cleavable moiety (—S—S—) to reduce non-target retention of the biotin-DOTA conjugate. Exemplary linkers of this type exhibit the following formula:

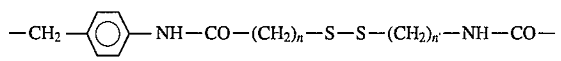

where n and n' preferably range between 0 and 5.

The advantage of using conditionally clearable linkers is an improvement in target/non-target localization of the active agent. Conditionally cleavable linkers include enzymatically clearable linkers, linkers that are cleaved under acidic conditions, linkers that are cleaved under basic conditions and the like. More specifically, use of linkers that are cleaved by enzymes, which are present in non-target tissues but reduced in amount or absent in target tissue, can increase target cell retention of active agent relative to non-target cell retention. Such conditionally clearable linkers are useful, for example, in delivering therapeutic radionuclides to target cells, because such active agents do not require internalization for efficacy, provided that the linker is stable at the target cell surface or protected from target cell degradation.

G. Ether, thioether, ester and thioester linkers are also useful in the practice of the present invention, because such linkages are acid cleavable and therefore facilitate improved non-target retention. Exemplary linkers of this type have the following general formula:

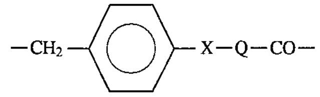

where

X is O or S; and

Q is a bond, a methylene group, a —CO— group or $—CO—(CH_2)_n—NH—$; and n ranges from 1–5.

Other such linkers have the general formula: $—CH_2—X—Q$, where Q and X are defined as set forth above.

H. Another amine-containing linker of the present invention is structured as follows:

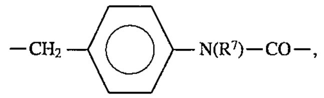

where $R^7$ is lower alkyl, preferably methyl.

In this case, resistance to enzymatic cleavage is conferred by the alkyl substitution on the amine.

I. Polymeric linkers are also contemplated by the present invention. Dextran and cyclodextran are preferred polymers useful in this embodiment of the present invention as a result of the hydrophilicity of the polymer, which leads to favorable excretion of conjugates containing the same. Other advantages of using dextran polymers are that such polymers are substantially non-toxic and non-immunogenic, that they are commercially available in a variety of sizes and that they are easy to conjugate to other relevant molecules. Also, dextran-linked conjugates exhibit advantages when non-target sites are accessible to dextranase, an enzyme capable of cleaving dextran polymers into smaller units while non-target sites are not so accessible.

Other linkers of the present invention are produced prior to conjugation to DOTA and following the reduction of the biotin carboxy moiety. These linkers of the present invention have the following general formula:

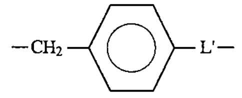

Embodiments of linkers of this aspect of the present invention include the following:

J. An ether linkage as shown below may be formed in a DOTA-biotin conjugate in accordance with the procedure indicated below.

$L'=—NH—CO—(CH_2)_n—O—$ where n ranges from 1 to 5, with 1 preferred.

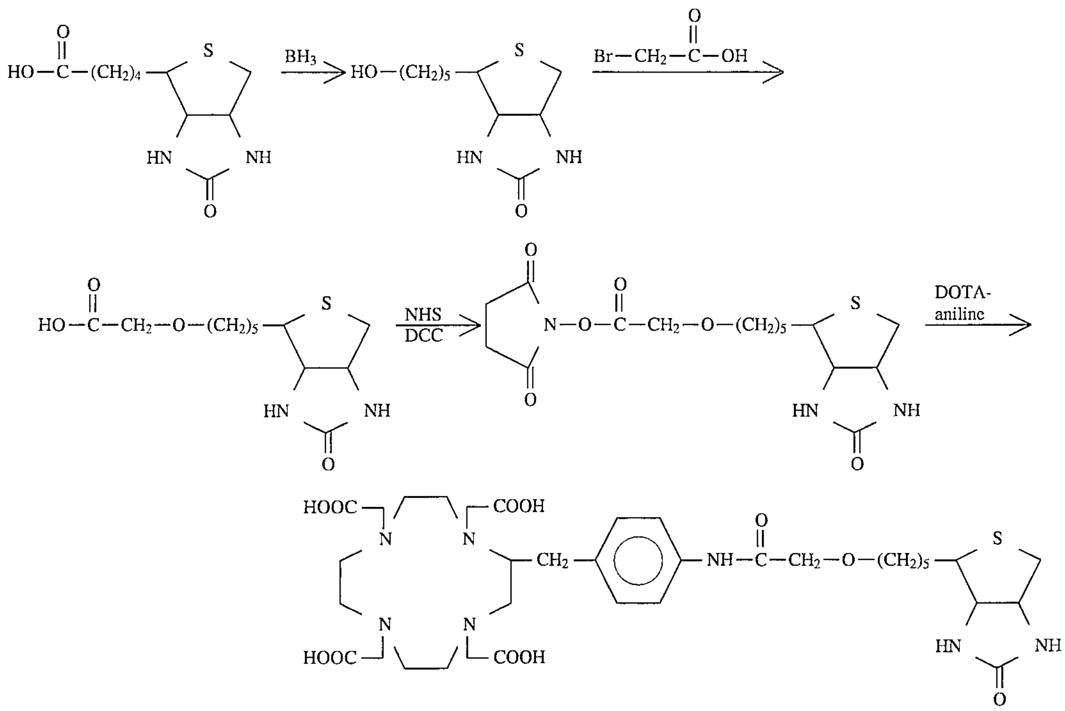

This linker has only one amide moiety which is bound directly to the DOTA aniline (as in the structure of DOTA-SC-biotin). In addition, the ether linkage imparts hydrophilicity, an important factor in facilitating renal excretion.

K. An amine linker formed from reduced biotin (hydroxybiotin or aminobiotin) is shown below, with conjugates containing such a linker formed, for example, in accordance with the procedure described in Example XXI.

L'=—NH—

This linker contains no amide moieties and the unalkylated amine may impart favorable biodistribution properties since unalkylated DOTA-aniline displays excellent renal clearance.

L. Substituted amine linkers, which can form conjugates via amino-biotin intermediates, are shown below.

$$L' = -(CH_2)_q-NH-CO-CH_2-N(R^8)-R^9$$

where $R^8$ is H; $-(CH_2)_2-OH$ or a sulfate or phosphonate derivative thereof; or

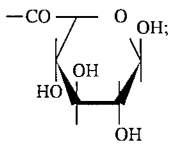

or the like; and $R^9$ is a bond or $-(CH_2)_n-CO-NH-$, where n ranges from 0–5 and is preferably 1 and where q is 0 or 1. These moieties exhibit the advantages of an amide only directly attached to DOTA-aniline and either a nonamide amine imparting a positive charge to the linker in vivo or a N-alkylated glucuronide hydrophilic group, each alternative favoring renal excretion.

M. Amino biotin may also be used as an intermediate in the production of conjugates linked by linkers having favorable properties, such as a thiourea-containing linker of the formula:

L'=—NH—CS—NH—

Conjugates containing this thiourea linker have the following advantages: no cleavable amide and a short, fairly polar linker which favors renal excretion.

A bis-DOTA derivative of the following formula can also be formed from amino-biotin.

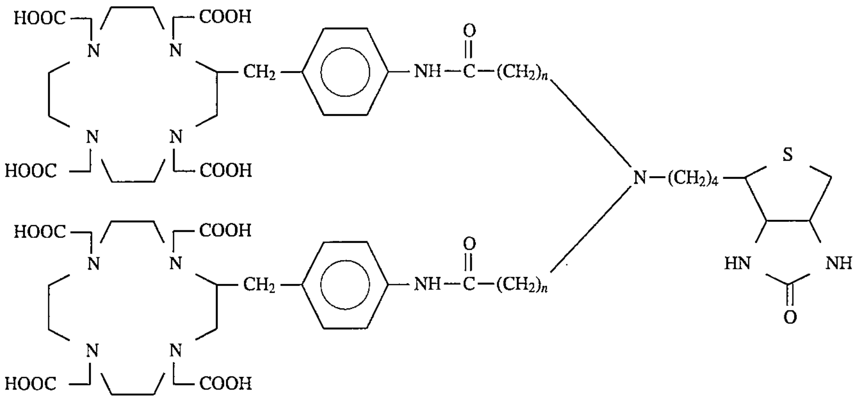

where n ranges from 1 to 5, with 1 and 5 preferred. This molecule offers the advantages of the previously discussed bis-DOTA derivatives with the added advantage of no cleavable amides.

Additional linkers of the present invention which are employed in the production of conjugates characterized by a reduced biotin carboxy moiety are the following:

L=—$(CH_2)_4$—NH—, wherein the amine group is attached to the methylene group corresponding to the reduced biotin carboxy moiety and the methylene chain is attached to a core carbon in the DOTA ring. Such a linker is conveniently synthesizable from lysine.

L=—$(CH_2)_q$—CO—NH—, wherein q is 1 or 2, and wherein the amine group is attached to the methylene group corresponding to the reduced biotin carboxy moiety and the methylene group(s) are attached to a core carbon in the DOTA ring. This moiety is synthesizable from amino-biotin.

The linkers set forth above are useful to produce conjugates having one or more of the following advantages:

bind avidin or streptavidin with the same or substantially similar affinity as free biotin;

bind metal $M^{+3}$ ions efficiently and with high kinetic stability;

are excreted primarily through the kidneys into urine;

are stable to bodily fluid amidases;

penetrate tissue rapidly and bind to pretargeted avidin or streptavidin; and are excreted rapidly with a whole body residence half-life of less than about 5 hours.

Synthetic routes to an intermediate of the DOTA-biotin conjugates depicted above, nitrobenzyl-DOTA, have been proposed. These proposed synthetic routes produce the intermediate compound in suboptimal yield, however. For example, Renn and Meares, "Large Scale Synthesis of Bifunctional Chelating Agent Q-(p-nitrobenzyl)-1,4,7,10-tetraazacyclododecane-N,N', N'',N'''-tetra acetic acid, and the Determination of its Enantiomeric Purity by Chiral Chromatography," *Bioconi. Chem.*, 3: 563–9, 1992, describe a nine-step synthesis of nitrobenzyl-DOTA, including reaction steps that either proceed in low yield or involve cumbersome transformations or purifications. More specifically, the sixth step proceeds in only 26% yield, and the product must be purified by preparative HPLC. Additionally, step eight proceeds in good yield, but the process involves copious volumes of the coreactants.

These difficulties in steps 6–8 of the prior art synthesis are overcome in the practice of the present invention through the use of the following synthetic alternative therefor.

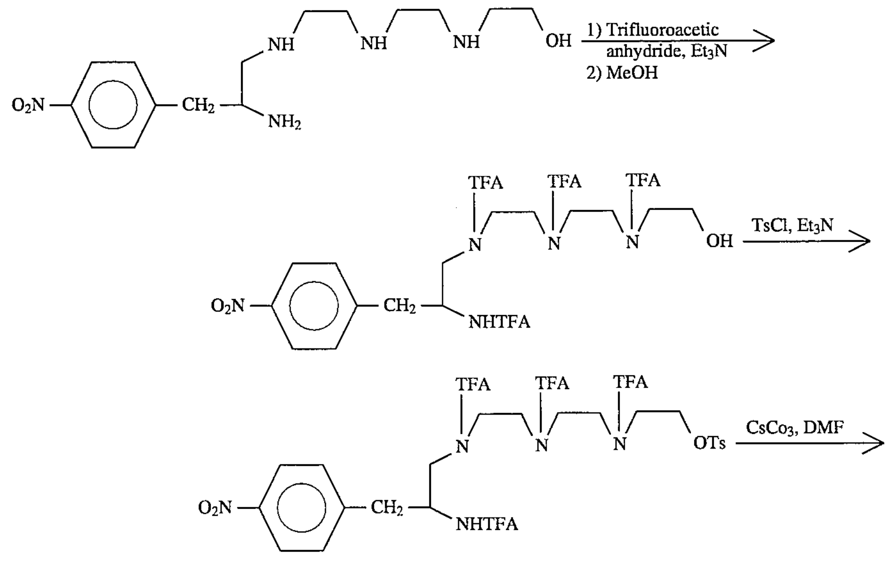

-continued

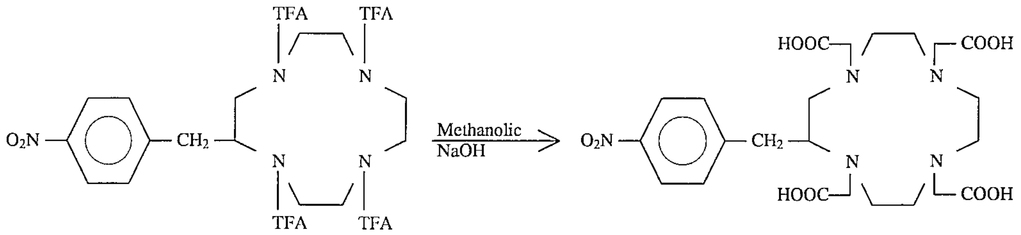

The poor yield in step six of the prior art synthesis procedure, in which a tetra amine alcohol is converted to a tetra-toluenesulfonamide toluenesulfonate as shown below, is the likely result of premature formation of the toluenesulfonate functionality (before all of the amine groups have been converted to their corresponding sulfonamides.

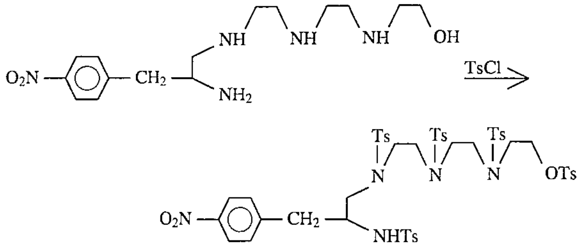

Such a sequence of events would potentially result in unwanted intra- or inter-molecular displacement of the reactive toluene sulfonate by unprotected amine groups, thereby generating numerous undesirable side-products.

This problem is overcome in the aforementioned alternative synthesis scheme of the present invention by reacting the tetra-amine alcohol with trifluoroacetic anhydride. Trifluoroacetates, being much poorer leaving groups than toluenesulfonates, are not vulnerable to analogous side reactions. In fact, the easy hydrolysis of trifluoroacetate groups, as reported in Greene and Wuts, "*Protecting Groups in Organic Synthesis*," John Wiley and Sons, Inc., New York, p. 94, 1991., suggests that addition of methanol to the reaction mixture following consumption of all amines should afford the tetra-fluoroacetamide alcohol as a substantially exclusive product. Conversion of the tetra-fluoroacetamide alcohol to the corresponding toluenesulfonate provides a material which is expected to cyclize analogously to the tetra-toluenesulfonamide toluenesulfonate of the prior art. The cyclic tetra-amide product of the cyclization of the toluenesulfonate of tetra-fluoroacetamide alcohol, in methanolic sodium hydroxide at 15°–25° C. for 1 hour, should afford nitro-benzyl-DOTA as a substantially exclusive product. As a result, the use of trifluoracetamide protecting groups circumvents the difficulties associated with cleavage of the very stable toluenesulfonamide protecting group, which involves heating with a large excess of sulfuric acid followed by neutralization with copious volumes of barium hydroxide.

Another alternative route to nitro-benzyl-DOTA is shown below.

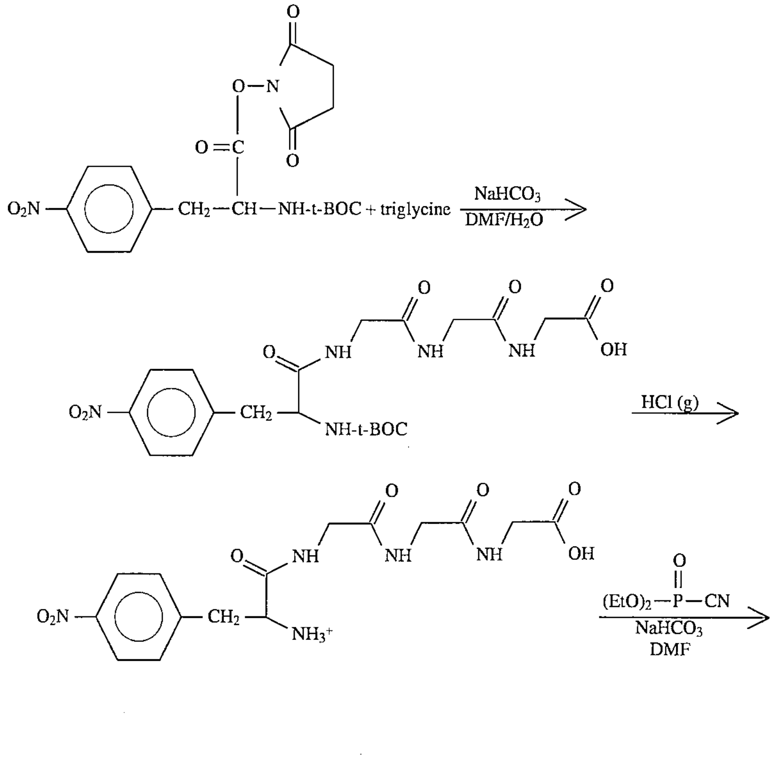

-continued

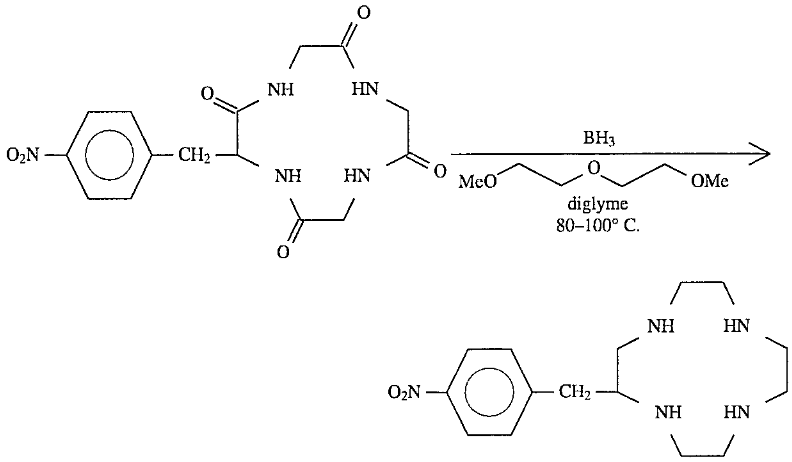

This alternative procedure involves the cyclizaton of p-nitrophenylalanyltriglycine using a coupling agent, such as diethylycyanophosphate, to give the cyclic tetraamide. Subsequent borane reduction provides 2-(p-nitrobenzyl)-1,4,7,10-tetraazacyclododecane, a common precursor used in publised routes to DOTA including the Renn and Meares articles referenced above. This alternative procedure of the present invention offers a synthetic pathway that is considerably shorter than the prior art Renn and Meares route, requiring two rather than four steps.

B. Polylysine Derivitization

Conjugates containing polylysine may also exhibit beneficial biodistribution properties. With whole antibodies, derivitization with polylysine may skew the biodistribution of conjugate toward liver uptake. In contrast, derivitization of Fab fragments with polylysine results in lower levels of both liver and kidney uptake; blood clearance of these conjugates is similar to that of Fab covalently linked to chelate. An exemplary polylysine derivitized chelate-biotin conjugate is illustrated below.

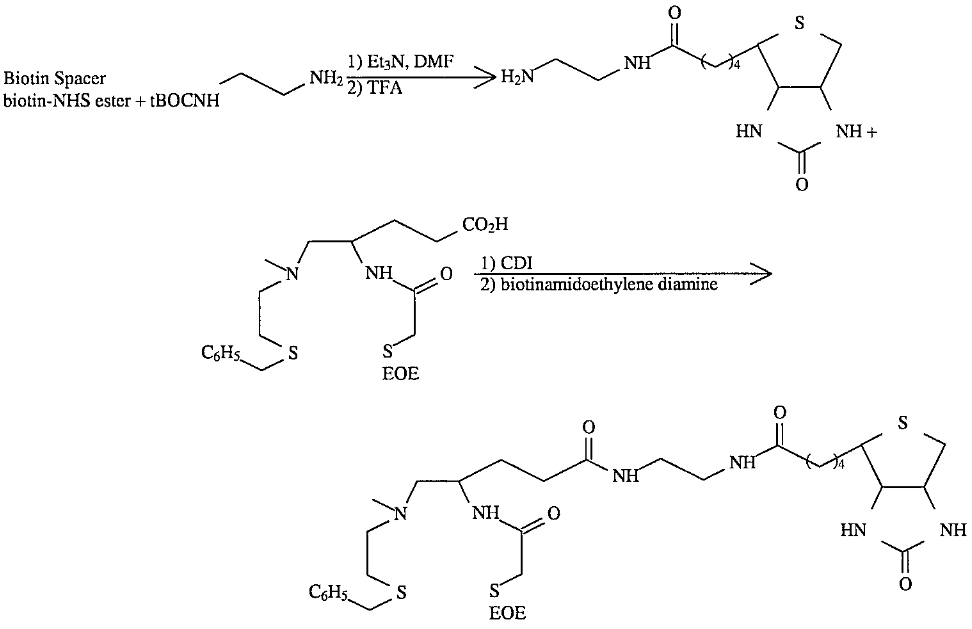

The resultant chelate-biotin conjugate shows superior kidney excretion. Although the net overall charge of the conjugate is neutral, the polycarboxylate nature of the molecule generates regions of hydrophilicity and hydrophobicity. By altering the number and nature of the carboxylate groups within the conjugate, excretion may be shifted from kidney to gastrointestinal routes. For instance, neutral compounds are generally cleared by the kidneys; anionic compounds are generally cleared through the GI system.

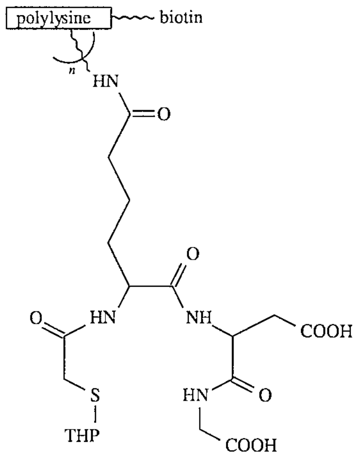

Inclusion of polylysine in radiometal-chelate-biotin conjugates is therefore useful for minimizing or eliminating RES sequestration while maintaining good liver and kidney clearance of the conjugate. For improved renal excretion properties, polylysine derivatives are preferably succinylated following biotinylation. Polylysine derivatives offer the further advantages of: (1) increasing the specific activity of the radiometal-chelate-biotin conjugate; (2) permitting control of rate and route of blood clearance by varying the molecular weight of the polylysine polymer; and (3) increasing the circulation half-life of the conjugate for optimal tumor interaction.

Polylysine derivitization is accomplished by standard methodologies. Briefly, poly-L-lysine is acylated according to standard amino group acylation procedures (aqueous bicarbonate buffer, pH 8, added biotin-NHS ester, followed by chelate NHS ester). Alternative methodology involves anhydrous conditions using nitrophenyl esters in DMSO and triethyl amine. The resultant conjugates are characterized by UV and NMR spectra.

The number of biotins attached to polylysine is determined by the HABA assay. Spectrophotometric titration is used to assess the extent of amino group derivitization. The radiometal-chelate-biotin conjugate is characterized by size exclusion.

C. Cleavable Linkage

Through insertion of a cleavable linker between the chelate and biotin portion of a radiometal-chelate-biotin conjugate, retention of the conjugate at the tumor relative to normal tissue may be enhanced. More specifically, linkers that are cleaved by enzymes present in normal tissue but deficient or absent in tumor tissue can increase tumor retention. As an example, the kidney has high levels of γ-glutamyl transferase; other normal tissues exhibit in vivo cleavage of γ-glutamyl prodrugs. In contrast, tumors are generally deficient in enzyme peptidases. The glutamyl-linked biotin conjugate depicted below is cleaved in normal tissue and retained in the tumor.

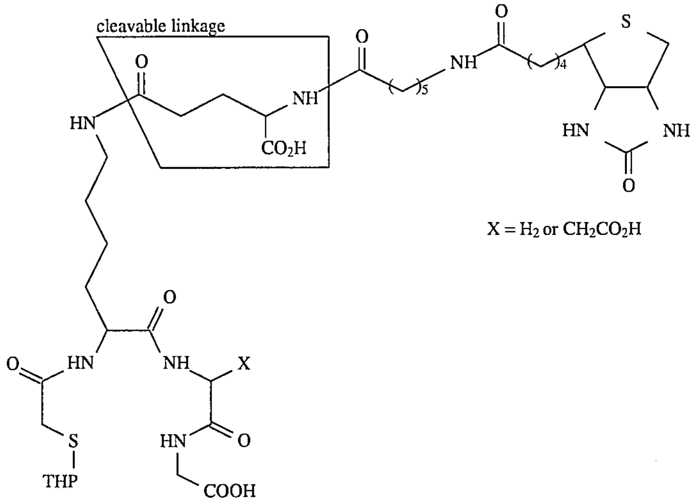

X = $H_2$ or $CH_2CO_2H$

D. Serine Linker With O-Polar Substituent

Sugar substitution of $N_3S$ chelates renders such chelates water soluble. Sulfonates, which are fully ionized at physiological pH, improve water solubility of the chelate-biotin conjugate depicted below.

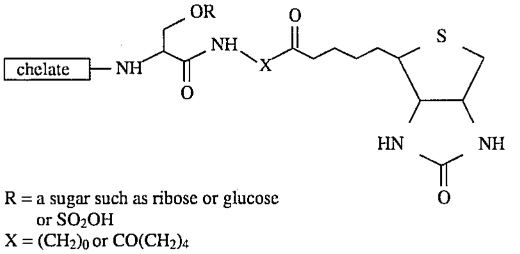

R = a sugar such as ribose or glucose or $SO_2OH$
X = $(CH_2)_0$ or $CO(CH_2)_4$ This compound is synthesized according to the standard reaction procedures. Briefly, biocytin is condensed with N-t-BOC-(O-sulfonate or O-glucose) serine NHS ester to give N-t-BOC-(O-sulfonate or O-glucose) serine biocytinamide. Subsequent cleavage of the N-t-BOC group with TFA and condensation with ligand NHS ester in DMF with triethylamine provides ligand-amidoserine(O-sulfonate or O-glucose)biocytinamide.

EXAMPLE VII

Preparation and Characterization of PIP-Radioiodinated Biotin Radioiodinated biotin derivatives prepared by exposure of poly-L-lysine to excess NHS-LC-biotin and then to Bolton-Hunter N-hydroxysuccinimide esters in DMSO has been reported. After purification, this product was radiolabeled by the iodogen method (see, for instance, Del Rosario et al., *J. Nucl. Med.* 32:5, 1991, 993 (abstr.)). Because of the high molecular weight of the resultant radioiodinated biotin derivative, only limited characterization of product (i.e., radio-HPLC and binding to immobilized streptavidin) was possible.

Preparation of radioiodinated biotin according to the present invention provides certain advantages. First, the radioiodobiotin derivative is a low molecular weight compound that is amenable to complete chemical characterization. Second, the disclosed methods for preparation involve a single step and eliminate the need for a purification step.

Briefly, iodobenzamide derivatives corresponding to biocytin (R=COOH) and biotinamidopentylamine (R=H) were prepared according to the following scheme. In this scheme, "X" may be any radiohalogen, including $^{125}I$, $^{131}I$, $^{123}I$, $^{211}At$ and the like.

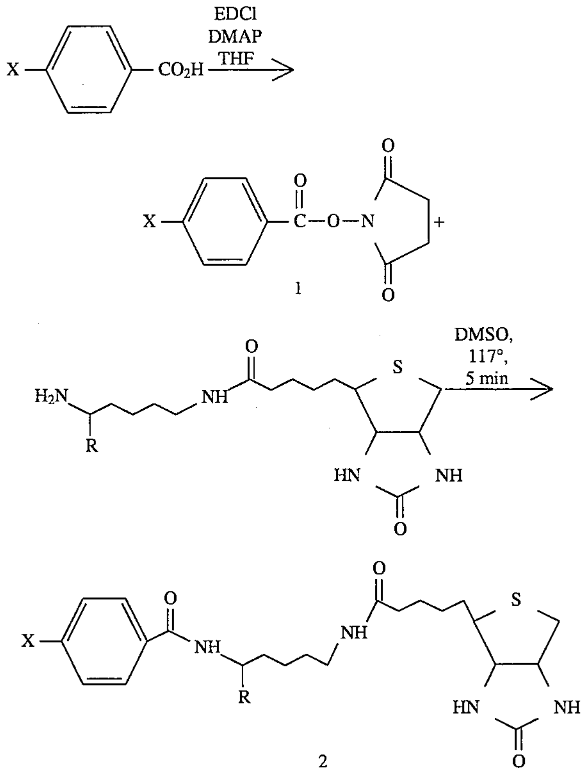

1

2

Preparation of 1 was generally according to Wilbur et al., *J. Nucl. Med.* 30:216–26, 1989, using a tributyltin intermediate. Water soluble carbodiimide was used in the above-depicted reaction, since the NHS ester 1 formed intractable mixtures with DCU. The NHS ester was not compatible with chromatography; it was insoluble in organic and aqueous solvents and did not react with biocytin in DMF or in buffered aqueous acetonitrile. The reaction between 1 and biocytin or delivered therefore becomes the biotin binding capacity at the target (i.e., the amount of antibody at the target and the avidin equivalent attached thereto).

For these embodiments of the pretargeting methods of the present invention, particle emitting therapeutic radionuclides resulting from transmutation processes (without non-radioactive carrier forms present) are preferred. Exemplary radionuclides include Y-90, Re-188, At-211, Bi-212 and the like. Other reactor-produced radionuclides are useful in the practice of these embodiments of the present invention, if they are able to bind in amounts delivering a therapeutically effective amount of radiation to the target. A therapeutically effective amount of radiation ranges from about 1500 to about 10,000 cGy depending upon several factors known to nuclear medicine practitioners.

Intraarterial administration pretargeting can be applied to targets present in organs or tissues for which supply arteries are accessible. Exemplary applications for intraarterial delivery aspects of the pretargeting methods of the present invention include treatment of liver tumors through hepatic artery administration, brain primary tumors and metastases through carotid artery administration, lung carcinomas through bronchial artery administration and kidney carcinomas through renal artery administration. Intraarterial administration pretargeting can be conducted using chemotherapeutic drug, toxin and anti-tumor active agents as discussed below. High potency drugs, lymphokines, such as IL-2 and tumor necrosis factor, drug/lymphokine-carrier-biotin molecules, biotinylated drugs/lymphokines, and drug/lymphokine/toxin-loaded, biotin-derivitized liposomes are exemplary of active agents and/or dosage forms useful for the delivery thereof in the practice of this embodiment of the present invention.

A problem associated with solid tumor target sites, for example, is penetration of the therapeutic agent into the active site. If homogeneous penetration of such target sites is achieved, more effective therapy is possible. One method that may be employed to enhance target site penetration of ligand or anti-ligand conjugated to a targeting agent or anti-ligand or ligand conjugated to a therapeutic moiety is the administration of a permeability enhancing moiety that induces or promotes vascular leakiness, disrupts cell-to-cell associations or similarly facilitates more homogeneous delivery of an administered conjugate to a target site characterized by a three dimensional cellular array. Preferably, permeability enhancing moieties of the present invention achieve their effects rapidly (e.g., within from about 30 seconds to about 1 hour following administration).

One example of this aspect of the present invention involves anti-ligand-targeting moiety conjugate administration (e,g., systemically, intraarterially, locally via catheter or the like) followed, for example, by intravascular perfusion catheter administration of a permeability enhancing moiety (e.g., an agent that induces gaps in the endothelium of venules through action on the postcapillary venules such as histamine, serotonin or bradykinin; or through action on the entire capillary bed such as bacterial endotoxins; or the like) which disrupts the target three dimensional structure and induces microvascular leakiness, thereby permitting simultaneously or subsequently administered ligand-therapeutic agent conjugates to achieve a higher interstitial concentration at the target site. One method to achieve site specificity for the therapeutic agent conjugate administration is to administer that agent via catheter. The optimal route of administration for each administered component will be dictated by the recipient's physiological condition and the specific treatment selected therefor by an experienced medical practitioner. Optionally, a clearing agent may be administered prior or subsequent to the permeability enhancing moiety, with prior administration preferred.

The use of this aspect of the present invention also facilitates the delivery of higher molecular weight therapeutic agent-bearing conjugates to target sites characterized by a three dimensional cellular array. For example, one or more ligand or anti-ligand molecules as well as a plurality of therapeutic agent molecules may be conjugated to a polymer to form an entity of the following formula:

$$\text{Therapeutic Agent}_{1-30}\text{-Polymer-Ligand or Anti-ligand}_{1-10}$$

A specific embodiment of this aspect of the present invention, useful particularly for target sites characterized by an accessible (for administration purposes) arterial supply as discussed herein, involves intraarterial administration of permeability enhancing agent followed by such administration of therapeutic agent-polymer-ligand or -anti-ligand conjugate. An exemplary conjugate suitable for such delivery is a biotinylated derivative of the hydroxy-propyl-methacrylate-adriamycin conjugate discussed by R. Duncan and J. Kopecek, *Advances in Polymer Science,* 57: 52–101 (1984) and R. Duncan, *Anticancer Drugs,* 3: 175–210 (1992).

Alternatively, the permeability enhancing moiety may be administered prior to administration of the targeting moiety-ligand or -anti-ligand conjugate to facilitate more homogenous targeting of that administered conjugate which serves as a receptor for subsequently administered anti-ligand- or ligand-therapeutic agent conjugate. Additionally, permeability enhancing moieties may also be employed in three-step pretargeting protocols of the present invention.

Preferred permeability enhancing moieties of the present invention induce gaps in the endothelium of venules through "specific" or "non-specific" interaction. For the purposes of this discussion, non-specific permeability enhancing moieties are those that act upon the entire capillary bed. Exemplary permeability enhancing moieties of the non-specific type are bacterial endotoxins, metabolic inhibitors, drugs that alter microfilaments or microtubules and the like. Specific permeability enhancing moieties act on a portion of the capillary bed (e.g., on the postcapillary venules, capillaries or the like). Exemplary permeability enhancing agents of the specific type are histamine, serotonin, bradykinin, and the like. Other permeability enhancing moieties are mannitol, tumor necrosis factor, nitric oxide, prostaglandin E2, leukotriene, leukokinin and the like.

Alternatively, enhanced delivery of a diagnostic or therapeutic substance, for example, into a target tumor mass, can be achieved by systemically administering a conjugate containing a targeting moiety, a member of a ligand/anti-ligand binding pair and an amount of a permeability enhancing agent sufficient to achieve disruption of cell-to-cell association within the tumor mass. Such a permeability enhancing moiety may also be locally administered, for example, in the practice of the local or intraarterial administration protocols described above.

Exemplary permeability enhancing moieties of the present invention include any substance capable of disrupting cell-to-cell association within a three dimensional target cell array. Some preferred moieties include trichothecenes, which are small molecule protein synthesis inhibitors, ionophores, membrane-active compounds (particularly inhibitors of microtubule or microfilament polymerization, polymyxins and polyene antibiotics), cyclic toxin peptides, cytochalasins and combinations thereof. Verrucarin A, microcystin (from *Microcystin aeruginosa*), cycloheximide and puromycin are particularly preferred permeability enhancing moieties.

Moieties possessing a macrocyclic ring, a functional epoxide group or both are also preferred within the present invention. However, cytotoxic compounds that are devoid of macrocyclic rings may also be suitable for use herein.

Small permeability enhancing moieties having a molecular weight less than or equal to about 2,000 daltons, and particularly those having a molecular weight less than or equal to 1,000 daltons, are also preferred. Such small permeability enhancing moieties are able to pass freely between adjacent cells whose cytoplasms are coupled via gap junctional complexes.

In a systemic administration embodiment, a permeability enhancing moiety having a molecular weight of about 1,000 daltons or less is conjugated to a targeting moiety (preferably also having a ligand or an anti-ligand bound thereto) through a selectively cleavable covalent linkage. In this embodiment, after delivery of the conjugate to a target cell, the permeability enhancing moiety is released at the target cell, and is then distributed to adjacent cells through gap junctions. Free diffusion of the released moiety will increase the efficiency, for example, of tumor mass disruption.

For some permeability enhancing moieties, it may be advantageous to conjugate multiple moieties to a carrier molecule through a selectively cleavable covalent linkage. As used herein, "carrier molecule" includes, but is not limited to, a large protein or polymer capable of binding many permeability enhancing moieties to a single targeting moiety. Preferred carrier molecules include albumin, dextran, hydroxy-propylmethacrylamide, poly-L-lysine and polyglutamate, all of which have a molecular weight in excess of 5,000 daltons. Carrier molecules may also be produced through chemical syntheses or recombinant DNA technology. A carrier molecule generally is derivatized with small selectively cleavable linking groups, which enable binding of one or more permeability enhancing moieties to the carrier. The "permeability enhancing moiety loaded" carrier is then either locally or intraarterially administered or systemically administered after being covalently attached to a targeting moiety (directly or through a linker).

Alternatively, specific target site vascular permeability is achievable by administering an effective amount of a permeability enhancing moiety which is a target cell inflammatory response mediator. A preferred permeability enhancing moiety of this type is a substance that is capable of localizing at a target site and capable of mediating complement-dependent inflammation at the target site within a patient. Such moieties are recognized by their ability to mediate complement-dependent cytotoxicity in vitro with the recipient's serum. Permeability enhancing moieties may be monoclonal antibodies, polyclonal antibodies, chimeric antibodies, human or humanized antibodies or other moiety having the capabilities described above.

Permeability enhancing moieties of this type may also be administered as a conjugate with a vasoactive complement-derived peptide, such as a peptide derived from C2. Complement-derived peptides are linked to the permeability enhancing moieties in a manner permitting release of the complement-derived peptide at the target site, such as through a labile linkage (i.e., a Schiff base linkage).

Preferably, a subset of antibodies, such as mouse antibodies, human/mouse chimeric antibodies or humanized antibodies are used to induce target site-specific increases in vascular permeability. These monoclonal antibodies mediate target cell lysis and/or target cell inflammatory responses in vitro which contribute to target site-specific vascular permeability increases. Both direct and indirect action on target cells may be accomplished by mediation of complement-dependent cytotoxicity. The ability to mediate complement-dependent cytotoxicity in vitro is indicative of the ability to mediate complement-dependent inflammation in vivo.

The invention exploits one attribute of antibodies—possession of isotype- and/or subclass-specific functions. For example, murine $IgG_3$ and human/mouse chimeric antibodies having human $IgG_1$ or $IgG_3$ constant portions are generally considered superior to other immunoglobulins of murine or murine/human nature for mediating antibody-dependent cell-mediated inflammation (ADCC) or complement-dependent cellular toxicity. Antibodies or other moieties effective in mediating target-site complement-dependent cytotoxicity must be capable of utilizing the serum complement native to the ultimate recipient having confirmed or potential target sites. Consequently, human antibodies are expected to be capable of utilizing human serum. Antibodies of other types are therefore tested for this ability when administration to human recipients is contemplated.

Exemplary moieties known to mediate dependent cytotoxicity are NR-CO-04, a murine $IgG_3$ antibody directed to colon carcinoma; NR-LU-13, a murine/human chimeric antibody featuring a human constant region and murine variable region of NR-LU-10, an antibody directed to a 37–40 kilodalton pancarcinoma glycoprotein; NR-LU-03, an $IgG_3$ antibody generated by immune complex immunization with NR-LU-10; R24, an $IgG_3$ antibody directed against GD3 disclosed by Houghton et al., *Proc. Natl. Acad. Sci* (USA), 82:1242–1246, 1985; antibody 3F8, a mouse $IgG_3$ directed against GD2 disclosed by Munn et al., *Cancer Res.*, 47:6600–6605, 1987 and Cheung et al., *J. Clin. Invest.*, 81:1122–1128, 1988; and the like.

Some polymers useful in the practice of this permeability enhancing aspect of the present invention serve solely as a carrier for multiple therapeutic agents. Preferred polymers, also direct the biodistribution of the ligand or anti-ligand and therapeutic agents to which the polymer is bound to renal rather than, for example, hepatobiliary excretion. For many administered therapeutic agents (e.g., radionuclides), renal excretion is preferred, especially for therapeutic protocols.

Exemplary polymers for use in the practice of the present invention are excreted or which metabolites thereof are excreted through a renal pathway when administered to a mammalian recipient and that is capable of covalently or non-covalently binding to one or more drugs, anti-tumor agents, peptides, chelates, ligands, anti-ligands or other small molecules and imposing a renal route of excretion upon the associated molecule(s). Such polymers include polar molecules having a molecular weight ranging from about 3 kD to about 70 kD).

Exemplary polymers useful in permeability enhancing aspects of the present invention are dextran; dextran derivatives including carboxymethyl dextran, anionic or polar derivatives thereof such as carboxymethyl-dextran, 3-mercapto-2-hydroxypropyl dextran and the like; hyaluronic acid, inulin, carboxymethyl cellulose; hydroxy-propylmethacrylamide (HPMA) polymers; succinylated polylysine; polyaspartate; polyglutamate; polyethyleneglycol (PEG); and the like. Dextran polymers are described herein as the prototypical polymers for use in the permeability enhancing aspects of the invention.

For use in the present invention, dextran polymers preferably range between about 5 and about 15 kD in size, although larger moieties may also be used. When larger (from about 40 to about 70 kD) polymers are employed in accordance with the present invention, the rate of clearance of the conjugate from a recipient is slowed, but the renal pathway for excretion is maintained. In this manner, the moieties bound to the polymer exhibit increased bioavailability as a result of the increased circulation time thereof.

Such bound molecules remain directed to renal excretion, however.

Exemplary dextran-containing conjugates of the present invention are dextran-biotin conjugates. Chelate-biotin-dextran conjugates of the present invention are formed, for example, from oxidized dextran by conjugating biocytin hydrazide thereto followed by reaction with a chelate active ester, such as a N-hydroxy succinimidyl ester, a tetrafluorophenyl ester and the like. Alternatively, chelate-biotindextran can be formed by reacting dextran hydrazide with the carboxy terminus of a chelate-biocytin conjugate. Preferably, the carboxy terminus has been derivitized to form an active ester, such as an N-hydroxysuccinimidyl ester or the like, an alternative protocol of general applicability to different polymers is discussed in Example XVII.

Biotin-dextran, lysine fixable (BDLF, available from Sigma Chemical Company, St. Louis, Mo.) is a preferred polymer-ligand for use in the practice of the present invention.

Active agents can be bound to dextran polymers characterized by short term serum stable linkages disposed between monomeric, dimeric, trimeric or other convenient unit thereof. Such conjugates are also preferably large (exhibiting a molecular weight ranging from about 40 to about 70 kD). One advantage of the use of such polymers is that the molecules affixed thereto will exhibit an increased circulation time as well as decreased liver uptake. More specifically, the circulation time of the bound molecules is dictated by the maintenance of polymeric structural integrity in vivo. Depolymerization releases bound molecule-monomer, -dimer, -trimer or like moieties that are themselves rapidly cleared from the recipient's circulation, preferably via the renal pathway.

Depolymerization may be controlled in any convenient manner therefor, including, for example, the following methods:

Use of linkages between dextran units containing chemical groups that are stable in serum for a period of time sufficient to provide an appropriate circulation time to the small molecules bound thereto (e.g., 1 to 3 hours for active agent in both the pretargeting and targeted, direct labeled protocols); or Use of linkages between dextran units that are enzymatically cleaved upon administration of enzyme after the passage of an appropriate amount of bound molecule circulation time.

In the first approach, groups such as esters, acetals, disulfides, thioacetals or the like are employed. For example, an ester linkage, having a serum stability of 1–3 hours such as phenyl or activated phenyl or phthalyl (e.g., chloro-substituted, fluoro-substituted, multi-halogen-substituted, nitro-substituted or the like), may be employed to attach dextran polymer units. Such a linkage is stable in serum for a time sufficient to facilitate localization of the molecules bound to the polymer to the target site.

The second approach includes the use of dextran units susceptible to cleavage by an administrable enzyme that is not found in large amounts in human serum. Exemplary enzymes useful in the practice of this aspect of the present invention include dextranase, alpha-amylase, pullulanase (a bacterial alpha-1,6-polysaccharidase) and the like. The enzymes are administered, by any convenient route in any convenient dosage form therefor. Such enzymes are optionally conjugated or formed as fusion proteins with long circulating proteins, including albumin, immunoglobulins or portions thereof, and the like. In this manner, the administered enzymes remain in circulation for a time sufficient to effect depolymerization of the polymer.

As discussed previously, cross-linking of moieties bound to a target cell surface results in internalization of those bound moieties by the cell. This cross-linking phenomena can be exploited in several ways using the 2-step and 3-step pretargeting protocols of the present invention. Three exemplary protocols of the cross-linking/internalization aspect of the present invention using the exemplary biotin/avidin ligand/anti-ligand pair can be described as follows:

1) (two-step) administer targeting moiety-biotin-therapeutic agent conjugate (or biotin-targeting moiety-therapeutic agent conjugate); and administer avidin or streptavidin to cross-link the previously localized conjugate. A variation of this protocol involves administration of targeting moiety-biotin conjugate followed by administration of therapeutic agent-avidin or -streptavidin conjugate.

2) (two-step) administer avidin- or streptavidin-targeting moiety-therapeutic agent conjugate (or therapeutic agent-avidin- or streptavidin-targeting moiety conjugate; or a therapeutic agent-containing conjugate that also incorporates Antibody-(avidin or streptavidin)$_2$ or (Antibody)$_2$-avidin or -streptavidin); and administer multiple biotin-polymer conjugate to cross-link the previously localized conjugate. A variation of this protocol involves administration of a targeting moiety-avidin or -streptavidin conjugate, Antibody-(avidin or streptavidin)$_2$ conjugate or (Antibody)$_2$-avidin or -streptavidin conjugate followed by administration of multiple biotin-polymer therapeutic agent conjugate.

3) (three-step) administer targeting moiety-biotin conjugate;

administer avidin or streptavidin;

administer multiple biotin-polymertherapeutic agent conjugate to either cross-link the previously localized avidin or streptavidin or to be internalized into the cell as a result of the avidin or streptavidin cross-linking of previously localized biotin-containing conjugate.

These cross-linking/internalization embodiments of the present invention are exemplified below with reference to the biotin/avidin ligand/anti-ligand pair, monoclonal antibody targeting moieties and trichothecene therapeutic agents; however, the embodiments are amenable to use with other administered components.

Exemplary simple trichothecenes useful in the practice of this and other aspects of the present invention are as follows:

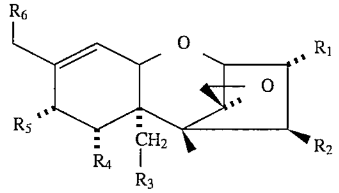

wherein:

$R_1$ is H, OH,

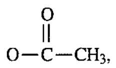

SH or $L_1$, $L_2$, $L_3$, or $L_4$;

$R_2$ is H, OH, or

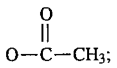

$R_3$ is H, OH, or

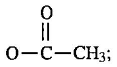

$R_4$ is H, or forms an epoxide group with $R_5$;

$R_5$ is H, OH,

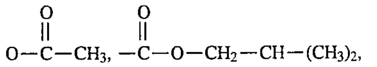

SH, $OCH_3$, $SCH_3$, $NH_2$, $NHCH_3$, $N(CH_3)_2$, $L_3$, $L_4$, or forms an epoxide group with $R_4$; and $R_6$ is H, OH, SH, $OCH_3$, $SCH_3$, $NH_2$, $NHCH_3$, $N(CH_3)_2$, $L_3$, or $L_4$ provided that at least one of $R_1$, $R_5$ and $R_6$ is $L_1$, $L_2$, $L_3$, or $L_4$ and further provided that $R_5$ and $R_6$ are not $L_1$ or $L_2$ and wherein $L_1$ is

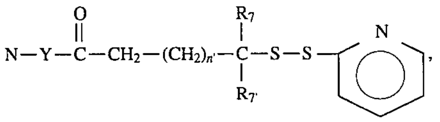

$L_2$ is

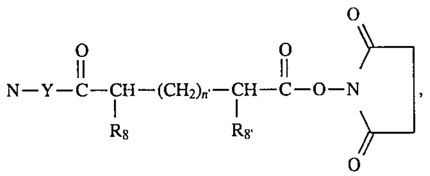

$L_3$ is

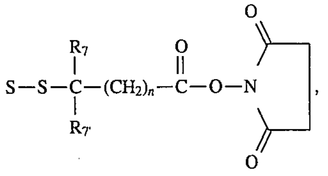

or $L_4$ is

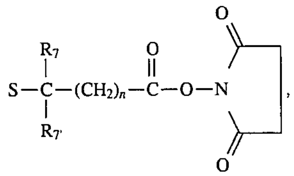

and wherein

Y is O or NH, $R_7$ or $R_{7'}$ is H or $CH_3$, $R_8$ or $R_{8'}$ is H or OH, n is one to ten; and n' is zero to ten.

Preferred simple trichothecenes are compounds where $R_2$ and $R_3$ are both

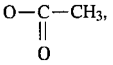

and $R_4$ and $R_5$ are both H. Other preferred trichothecenes are characterized as follows:

(1) $R_1$ is $L_1$ or $L_2$ and Y is NH, $R_7$ and $R_{7'}$ are independently either H or $CH_3$, $R_8$ and $R_{8'}$ are independently either H or OH, and n' is zero to ten; further provided that $R_2$ and $R_3$ are both

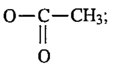

$R_4$ is H; and $R_5$ and $R_6$ are selected from the group consisting of H, OH, SH, $OCH_3$, $SCH_3$, $NH_2$, $NHCH_3$, $N(CH_3)_2$;

(2) $R_1$ is H, OH or SH; and $R_5$ and $R_6$ are selected from the group consisting of H, OH, SH, $OCH_3$, $SCH_3$, $NH_2$, $NHCH_3$, $N(CH_3)_2$, or $L_3$, wherein $R_7$ and $R_{7'}$ are independently either H or $CH_3$ and n is one to ten;

(3) $R_1$ is H, OH or SH; and $R_5$ or $R_6$ is selected from the group consisting of H, OH, SH, $OCH_3$, $SCH_3$, $NH_2$, $NHCH_3$, $N(CH_3)_2$, or $L_4$, wherein n is one to ten, and $R_7$ and $R_{7'}$ are independently either H or $CH_3$;

(4) $R_1$ is $L_3$ or $L_4$ wherein $R_7$ and $R_{7'}$ and independently either H or $CH_3$ and n is one to ten; and $R_5$ and $R_6$ are selected from the group consisting of H, OH, SH, $OCH_3$, $SCH_3$, $NH_2$, $NHCH_3$, $N(CH_3)_2$.

A prototypical simple trichothecene is anguidine or the 3-keto derivative thereof which may be used in protocol number 1 set forth above as, for example, Biotin-NR-LU-10monoclonal antibody-S—S—$(CH_2)_2$—CONH—N=(3-keto anguidine). Similarly, this simple trichothecene may be utilized in the protocols numbered 2 and 3 above as, for example, $(Biotin)_{18-20}$-Dextran-anguidine. Within the context of the above presented structures a prototypical simple trichothecene is characterized as follows: $R_1$ is $L_1$ and Y is NH, $R_7$ and $R_{7'}$ are both H, and n' is zero; $R_4$, $R_5$, $R_6$ are H; and $R_2$ and $R_3$ are both

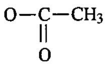

Exemplary macrocyclic trichothecenes useful in the practice of this and other aspects of the present invention are as follows:

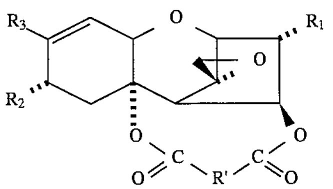

wherein R' is selected from the group consisting of

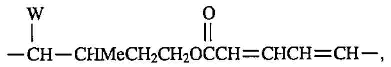

-continued

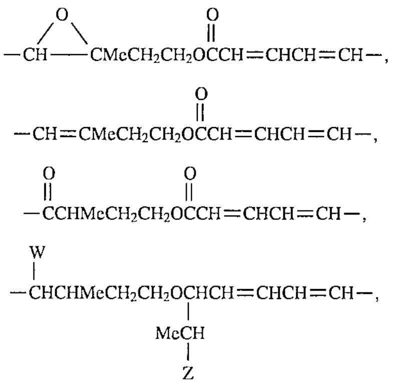

provided at least one of $R_1$, W and Z is $L_1$, $L_2$, $L_3$, or $L_4$, and further provided W and Z are not both $L_1$, $L_2$, $L_3$, or $L_4$ wherein $L_1$ is

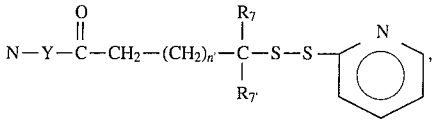

$L_2$ is

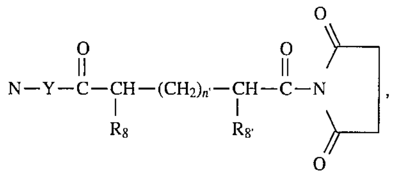

$L_3$ is

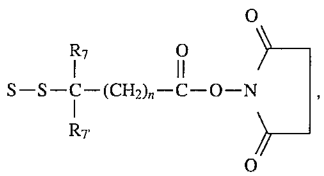

or $L_4$ is

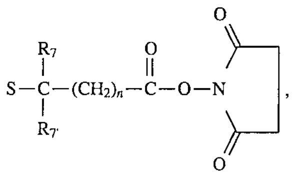

and wherein

Y is O or NH, $R_7$ or $R_{7'}$ is H or $CH_3$, $R_8$ or $R_{8'}$ is H or OH, n is one to ten; and n' is zero to ten;

and further provided that W can be an epoxide group between 2' and 3' and still further provided that W and Z can be independently either H, OH, or SH when W and Z are not $L_1$, $L_2$, $L_3$, or $L_4$; $R_1$ is H, OH, or SH when R1 is not $L_1$, $L_2$, $L_3$, or L4; and $R_2$ and $R_3$ are selected from the group consisting of, H, OH, SH, $OCH_3$, $SCH_3$, $NH_2$, $NHCH_3$, $N(CH_3)_2$, $L_3$ or $L_4$.

Preferred macrocyclic trichothecenes are compounds wherein R' is

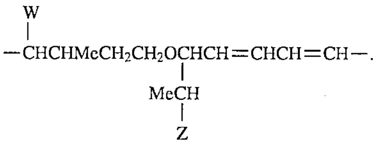

Such preferred compounds are derivatives of Roridin A. More preferred macrocyclic trichothecenes of this type are characterized as follows:

(1) $R_1$ is $L_1$, $L_2$, $L_3$, or $L_4$ wherein

Y is O or NH, $R_7$ and $R_{7'}$ are independently either H or $CH_3$, $R_8$ and $R_{8'}$ are independently either H or OH, n is one to ten, n' is zero to ten;

when $R_2$ and $R_3$ are selected from the group consisting of, H, OH, SH, $OCH_3$, $SCH_3$, $NH_2$, $NHCH_3$, $N(CH_3)_2$; and W and Z are independently either H, OH, or SH;

(2) $R_1$ and W are independently either H, OH, or SH; $R_2$ and $R_3$ are selected from the group consisting of, H, OH, SH, $OCH_3$, $SCH_3$, $NH_2$, $NHCH_3$, $N(CH_3)_2$; and Z is $L_1$, $L_2$, $L_3$, or $L_4$ and wherein Y is O or NH, R7 or $R_{7'}$ is H or $CH_3$, $R_8$ or $R_{8'}$ is H or OH, n is one to ten; and n' is zero to ten;

(3) $R_1$ and Z are H, SH, or OH; $R_2$ and $R_3$ are selected from the group consisting of, H, OH, SH, $OCH_3$, $SCH_3$, $NH_2$, $NHCH_3$, $N(CH_3)_2$; and W is either $L_1$, $L_2$, $L_3$, or $L_4$ and wherein Y is O or NH, $R_7$ or $R_{7'}$ is H or $CH_3$, $R_8$ or $R_{8'}$ is H or OH, n is one to ten, and n' is zero to ten; and (4) $R_1$, W and Z are independently either SH or OH; $R_2$ and $R_3$ are selected from the group consisting of H, OH, SH, $OCH_3$, $SCH_3$, $NH_2$, $NHCH_3$, $N(CH_3)_2$, $L_3$, or $L_4$ wherein $R_7$ and $R_{7'}$ are either H or $CH_3$, and n is one to ten;

provided that $R_2$ and $R_3$ are not both simultaneously $L_3$ or $L_4$.

Prototypical macrocyclic trichothecenes are Roridin A and derivatives thereof such as the 2'-oxo or the 13'-oxo derivatives. These trichothecenes may be used in protocol number 1 set forth above as, for example, Biotin-NR-LU-10monoclonal antibody-S—S—$(CH_2)_2$—CONH—N=(2'-oxo Roridin A), Biotin-NR-LU-10 monoclonal antibody-S—S—$(CH_2)_2$—CONH—N=(13'-oxo Roridin A), 2'-oxo-Roridin A—S—S—(CH $_2)_2$—CONH-lysine-NR-LU-10 monoclonal antibody-biotin and the like. Similarly, these macrocyclic trichothecenes may be utilized in the protocols numbered 2 and 3 above as, for example, $(Biotin)_{18-20}$-Dextran-2'-oxo Roridin A.

Prototypical Roridin A derivative macrocyclic trichothecenes may be characterized as follows:

$R_1$ and $R_2$ are both H; $R_3$ is $CH_3$; W is $L_1$, Y is NH, $R_{7'}$ are both H, n' is zero; and Z is OH;

$R_1$ and $R_2$ are both H; $R_3$ is $CH_3$; W is

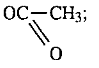

and

Z is $L_1$, Y is NH, $R_7$ and $R_{7'}$ are both H, n' is zero; and $R_1$ and $R_2$ are both H; $R_3$ is $CH_3$; W is $L_3$, $R_7$ and $R_{7'}$ are both H, n is one; and Z is OH.

Acid labile linker technology, e.g., hydrazone linkers, facilitate release of therapeutic agent in target cell endosomes and lysosomes (pH 3.5–5.5) where the released agent can exert its therapeutic effect (e.g., inhibition of protein synthesis). Disulfide linkages also promote release of therapeutic agent in endosomes and lysosomes of the target cells.

Exemplary protocols for trichothecene-linker preparation are discussed in Example XVIII. Exemplary protocols for trichothecene-antibody conjugation are set forth in Example XIX (A and B). Also, an exemplary protocol for the preparation of trichothecene-polymer conjugates is set forth in Example XIX (C).

In embodiments of the present invention employing radionuclide therapeutic agents, the rapid clearance of nontargeted therapeutic agent decreases the exposure of nontarget organs, such as bone marrow, to the therapeutic agent. Consequently, higher doses of radiation can be administered absent dose limiting bone marrow toxicity. In addition, pretargeting methods of the present invention optionally include administration of short duration bone marrow protecting agents, such as WR 2721. As a result, even higher doses of radiation can be given, absent dose limiting bone marrow toxicity.

While the pretargeting protocols set forth above have been described primarily in combination with delivery of a radionuclide diagnostic or therapeutic moiety, the protocols are amenable to use for delivery of other moieties, including anti-tumor agents, chemotherapeutic drugs and the like. For example, most naturally occurring and recombinant cytokines have short in vivo half lives. This characteristic limits the clinical effectiveness of these molecules, because near toxic doses are often required. Dose-limiting toxicities in humans have been observed upon high dose IL-2 or tumor necrosis factor administrations, for example.

A protocol, such as administration of streptavidin-targeting moiety conjugate followed by administration of biotinylated cytokine, is also contemplated by the present invention. Such pretargeting of anti-ligand serves to improve the performance of cytokine therapeutics by increasing the amount of cytokine localized to target cells.

Streptavidin-antibody conjugates generally exhibit pharmacokinetics similar to the native antibody and localize well to target cells, depending upon their construction. Biotinylated cytokines retain a short in vivo half-life; however, cytokine may be localized to the target as a result of the affinity of biotin for avidin. In addition, biotin-avidin experience a pH-dependent dissociation which occurs at a slow rate, thereby permitting a relatively constant, sustained release of cytokine at the target site over time. Also, cytokines complexed to target cells through biotin-avidin association are available for extraction and internalization by cells involved in cellular-mediated cytotoxicity.

A pre-formed antibody-streptavidin-biotin-cytokine preparation may also be employed in the practice of these methods of the present invention. In addition, a three-step protocol of the present invention may also be employed to deliver a cytokine, such as IL-2, to a target site.

Other anti-tumor agents that may be delivered in accordance with the pretargeting techniques of the present invention are selectins, including L-selectin, P-selectin and E-selectin. The presence of cytokines stimulates cells, such as endothelial cells, to express selectins on the surfaces thereof. Selectins bind to white blood cells and aid in delivering white blood cells where they are needed. Consequently, a protocol, such as administration of streptavidin- or avidin-targeting moiety conjugate followed by administration of biotinylated selectins, is also contemplated by the present invention. Such pretargeting of anti-ligand serves to improve the performance of selectin therapeutics by increasing the amount of selectin localized to target cells. In this manner, the necessity of cytokine induction of selectin expression is obviated by the localization and retention of selectin at a target cell population. A three-step protocol may also be employed to deliver selectins to a target site.

Chemotherapeutic drugs also generally exhibit short in vivo half-lives at a therapeutically effective dose. Consequently, another example of a protocol of the present invention includes administration of avidin-targeting moiety conjugate followed by administration of a biotin-chemotherapeutic drug conjugate or complex, such as a drug-carrier-biotin complex. A three-step protocol of the present invention may also be employed to deliver a chemotherapeutic drug, such as methotrexate, adriamycin, high potency adriamycin analogs, trichothecenes, potent enediynes, such as esperamycins and calicheamycins, cytoxan, vinca alkaloids, actinamycin D, taxol, taxotere or the like to a target site.

An additional aspect of the present invention is a method of eradicating target cells within a mammal, involving the steps of:

1) extracting effector cells (or precursors thereof) from the mammal;

2) cultivating the extracted effector cells in vitro with both an effector cell growth factor and a first immunogenic molecule, thereby producing sensitized effector cells recognizing the first immunogenic molecule or a moiety thereof;

3) administering to the mammal a second immunogenic molecule comprising an antibody, an antibody fragment or another targeting moiety which binds to the target cells and a member of a ligand/anti-ligand pair, and having at least one moiety in common with the first immunogenic molecule;

4) administering the sensitized effector cells produced in step 2 to the mammal; and 5) administering an effector cell growth factor bound to a member of the ligand/anti-ligand pair that is complementary to the member administered in step 2.

In this aspect of the present invention, the targeting moiety serves as a carrier to implant a strong predetermined antigenic signal on the target cells, ensuring that those target cells are sufficiently "immunogenic" for subsequent therapy. The engineered antigen bound to the target cells in vivo attracts subsequently administered presensitized effector cells to the target cells. In effect, this procedure constitutes an amplification of the tumor-associated antigen. The ligand/anti-ligand pair conjugate components are employed both to deliver effector cell growth factor to the target site and to avoid toxicity associated with circulating effector cell growth factor by decoupling the slow targeting moiety localization step from delivery of the growth factor.

An alternative method for eradicating target cells within a mammal comprises administering to the mammal an immunogenic molecule comprising an antibody- or other targeting moiety-ligand/anti-ligand pair member-immunogen conjugate which binds to the target cells in vivo. Subsequently, the complementary member of the ligand/anti-ligand pair is administered while conjugated to an effector cell growth factor. This in vivo embodiment may be employed when the immunogenic molecule is capable of inducing a therapeutic response in vivo. In this case, the antigenic signal is not predetermined, but is sufficiently strong to recruit a therapeutically effective number of effector cells to the target site. The binding of the immunogenic molecule to the target cells within the mammal induces a cytotoxic effector cell response directed at the target cells. Delivery of effector cell growth factor to the target site enhances the activity of the effector cells at that site.

In accordance with the present invention, effector cells are extracted from a mammal or recruited from within a mammal. These effector cells are cells capable of being "sensitized" such that the sensitized effector cells recognize a particular antigen, and have a cytotoxic effect on target cells bearing that antigen. The effector cells useful in the practice of this aspect of the present invention are cells designated as "committed T-cells," along with a variety of cytotoxic cells designated otherwise, including LAK cells, natural killer (NK) cells and other leukocytes and macrophages which could potentially be sensitized and manipulated similarly. In a preferred embodiment of the present invention, the effector cells are cytotoxic T-lymphocytes, also called cytotoxic T-cells.

Effector cells can be extracted from the mammal to be treated by any suitable procedure for collecting those cells from the patient and separating the desired effector cells from other cell types or biological materials which may be simultaneously extracted. Conventional cell harvesting or cytopheresis (e.g., leukopheresis) procedures may be used, and the effector cell extraction procedure may be repeated to obtain a larger quantity of effector cells. For example, the mammal may be subjected to one leukapheresis procedure per day for one or more days (e.g., for five days to collect a large number of effector cells such as T-cells).

The effector cell growth factor used may vary according to the type of effector cells employed, and may be any growth factor which stimulates the propagation of the cultured cells or enhances the activation thereof so that sensitized cytotoxic effector cells are produced. Among suitable growth factors are monokines for monocytes and lymphokines (e.g., IL-2) for lymphocytes such as T-lymphocytes).

The first immunogenic molecule (that with which the effector cells are incubated) may be the same as or different from the second immunogenic molecule (that which is administered to the mammal), provided that the two immunogenic molecules have at least one moiety in common. The proviso ensures that effector cells sensitized in vitro in the presence of the first immunogenic molecule will recognize the second immunogenic molecule in vivo.

When the targeting moiety, the ligand/anti-ligand pair member or the combination thereof is sufficiently immunogenic (i.e., is capable of inducing sensitization of effector cells), the targeting moiety-ligand/anti-ligand pair member conjugate may serve as the first as well as the second immunogenic molecule. Alternatively, a sufficiently immunogenic portion of the conjugate may be used as the first immunogenic molecule with the entire conjugate serving as the second immunogenic molecule.

When the targeting moiety-ligand/anti-ligand pair member conjugate or any portion thereof is not sufficiently immunogenic (i.e., is incapable of inducing sensitization of effector cells) various compounds may be attached to the targeting moiety or ligand/anti-ligand pair member to increase the immuogenicity thereof. In this case, the immunogen-targeting moiety-ligand/anti-ligand pair member conjugate is administered as the second immunogenic molecule.

Among the types of compounds that may be attached to a targeting moiety or ligand/anti-ligand pair member to increase the immunogenicity thereof are haptens or polypeptides which are "foreign" to the intended mammalian recipient (such as antigens, mitogens, other foreign proteins or fragments thereof, peptides that activate cytotoxic T-cells or the like). In some circumstances, attachment of the immunogen to the targeting moiety or ligand/anti-ligand pair member through a spacer (i.e., a linker molecule that serves to physically separate the components) may increase the immunogenicity of the linked first immunogenic molecule.

Haptens that are useful in the practice of the present invention include benzoate groups, nitrophenol groups, other small molecules such as acetic acid and derivatives thereof, penicillinic acid and derivatives thereof, sulfanilic acid derivatives, hexoseamines, ribonucleotides, ribonucleosides, isocyanates, isothiocyanates and the like. Preferred haptens are benzoic acid, dinitro-chlorobenzene, dinitro-fluorobenzene, picrylchloride, p-aminobenzenearsonate, p-azo-benzenearsonate, acetic acid, dinitrophenol, trinitrophenol, trinitrophenol-epsilon-aminocaproic acid, 3-iodo-4-hydroxyl-5-nitrophenylacetic acid, p-hydroxyphenylacetic acid, p-sulfanilic acid, 2,4-diisocyanate, fluorescein isothiocyanate, N-acetyl-glucosamine and the like.

"Foreign" polypeptides useful in the practice of this aspect of the present invention include flagellins, fragments of keyhole limpet hemocyanin, histocompatibility antigens, bacterial cell surface proteins, viral coat proteins, fragments thereof and the like. Small polypeptide fragments are generally preferred in order to avoid interference with the biodistribution of the targeting moiety-containing conjugate. T-cell mitogens such as the proteins pokeweed antiviral protein and phytohemagglutinin also may be used.

A specific example of the in vitro sensitization embodiment of this aspect of the present invention may be described as follows:

1) extracting effector cells (or precursors thereof) from the mammal;
2) cultivating the extracted effector cells in vitro with interleukin-2 (IL-2) and avidin or streptavidin, thereby producing sensitized effector cells recognizing avidin or streptavidin or a moiety thereof;
3) administering to the mammal a targeting moiety-avidin or -streptavidin conjugate;
4) administering the sensitized effector cells produced in step 2 to the mammal; and
5) administering an IL-2-biotin conjugate. A three-step pretargeting approach may be designed for the practice of this aspect of the present invention.

Another specific example of an in vitro embodiment of the present invention involves the following steps:

1) extracting effector cells (or precursors thereof) from a mammal;
2) cultivating the effector cells with IL-2;
3) conjugating the cultivated effector cells with biotin;
4) administering a targeting moiety-avidin or targeting moiety-streptavidin to the mammal, wherein the targeting moiety is specific for the cells upon which effector cell action is desired; and
5) administering effector cell-biotin conjugate to the mammal.

In this embodiment of the present invention, steps 3 and 4 may be conducted in reverse order. Also, a clearing agent may be administered between steps 4 and 5. In addition, a three-step pretargeting protocol may be employed.

A specific example of the in vivo sensitization embodiment of this aspect of the present invention may be described as follows:

1) administering to the mammal a hapten-targeting moiety-avidin or -streptavidin conjugate to induce sensitization of effector cells; and 2) administering to the mammal an IL-2-biotin conjugate. A three-step pretargeting protocol may also be designed for the practice of this embodiment of the present invention.

Another protocol employing the concepts of the effector cell sensitization involves principles incident to organ transplantation. The HLA system in humans, including class I and class II antigens, corresponds to the MHC complex of mice, for example, and is a major factor in self/non-self recognition. For this reason, HLA matching is conducted in selecting candidates for organ transplants. Persons with more similar HLA (i.e., twins, siblings, parents and the like) are the most preferably organ transplant donors, because the donated organ is less likely to be recognized as non-self by the recipient.

Some HLA antigens are relatively rare in humans, i,e., are infrequently present in the human HLA display. For example, the HLA-B7 antigen is present on only 5% of the human population. Consequently, HLA-B7 is recognized as non-self in 95% of humans. Such relatively rare antigens can therefore be targeted to target sites within an individual that does not exhibit the antigen. Due to the presence of the antigen at the target site, the target will be recognized as non-self by the recipient, thereby recruiting the recipient's immune system to combat the target. Since some targets (e.g., certain tumors) are poorly recognized as non-self, the presence of a recognized non-self antigen at that site will improve the recipient's immune system response to the target.

HLA antigen that is not present in a recipient can be delivered to a target site by conjugation with a targeting moiety, as part of a fusion protein with a targeting moiety or as part of a conjugate or fusion protein with a ligand or an anti-ligand in the two-step or three-step pretargeting protocols described herein.

The invention is further described through presentation of the following examples. These examples are offered by way of illustration, and not by way of limitation.

EXAMPLE I

Synthesis of a Chelate-Biotin Conjugate

A chelating compound that contains an $N_3S$ chelating core was attached via an amid linkage to biotin. Radiometal labeling of an exemplary chelate-biotin conjugate is illustrated below.

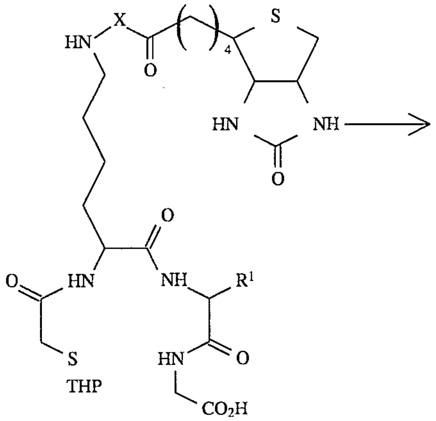

X = $(CH_2)_0$, short chain
X = $CO(CH_2)_5NH$, long chain
$R^1$ = H or $CH_2CO_2H$

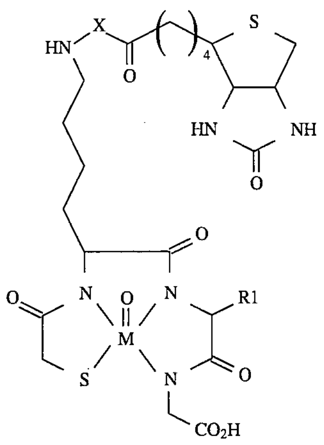

M = Tc or Re

The spacer group "X" permits the biotin portion of the conjugate to be sterically available for avidin binding. When "$R^1$" is a carboxylic acid substituent (for instance, $CH_2COOH$), the conjugate exhibits improved water solubility, and further directs in vivo excretion of the radiolabeled biotin conjugate toward renal rather than hepatobiliary clearance.

Briefly, N-α-Cbz-N-Σ-t-BOC protected lysine was converted to the succinimidyl ester with NHS and DCC, and then condensed with aspartic acid β-t-butyl ester. The resultant dipeptide was activated with NHS and DCC, and then condensed with glycine t-butyl ester. The Cbz group was removed by hydrogenolysis, and the amine was acylated using tetrahydropyranyl mercaptoacetic acid succinimidyl ester, yielding S-(tetrahydropyranyl)-mercaptoacetyl-lysine. Trifluoroacetic acid cleavage of the N-t-BOC group and n-butyl esters, followed by condensation with LC-biotin-NHS ester provided (Σ-caproylamide biotin)-aspartyl glycine. This synthetic method is illustrated below.

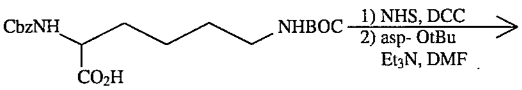

-continued

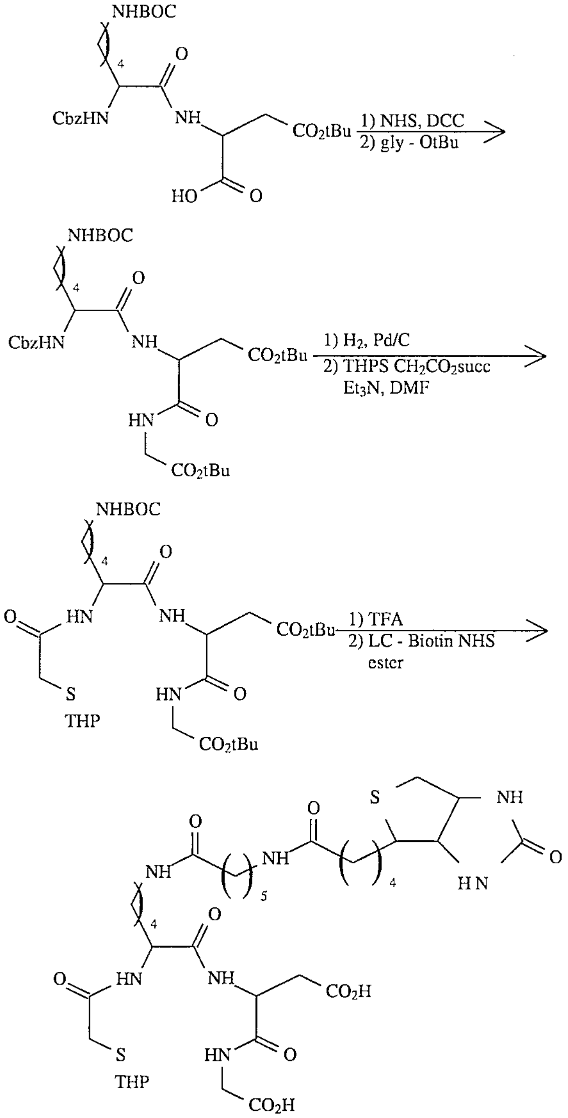

$^{1}H$ NMR: ($CD_3OD$, 200 MHz Varian): 1.25–1.95 (m, 24H), 2.15–2.25 (broad t, 4H), 2.65–3.05 (m, 4H), 3.30–3.45 (dd, 2H), 3.50–3.65 (ddd, 2H), 3.95 (broad s, 2H), 4.00–4.15 (m, 1H), 4.25–4.35 (m, 1H), 4.45–4.55 (m, 1H), 4.7–5.05 (m overlapping with HOD).

Elemental Analysis: C, H, N for $C_{35}H_{57}N_7O_{11}S_2.H_2O$ calculated: 50.41, 7.13, 11.76 found: 50.13, 7.14, 11.40

EXAMPLE II

Preparation of a Technetium or Rhenium Radiolabeled Chelate-Biotin Conjugate The chelate-biotin conjugate of Example I was radiolabeled with either $^{99m}$Tc pertechnetate or $^{186}$Re perrhenate. Briefly, $^{99m}$Tc pertechnetate was reduced with stannous chloride in the presence of sodium gluconate to form an intermediate Tc-gluconate complex. The chelate-biotin conjugate of Example I was added and heated to 100° C. for 10 min at a pH of about 1.8 to about 3.3. The solution was neutralized to a pH of about 6 to about 8, and yielded an $N_3S$-coordinated $^{99m}$Tc-chelate-biotin conjugate. C-18 HPLC gradient elution using 5–60% acetonitrile in 1% acetic acid demonstrated two anomers at 97% or greater radiochemical yield using 67 (gamma ray) detection.

Alternatively, $^{186}$Re perrhenate was spiked with cold ammonium perrhenate, reduced with stannous chloride, and complexed with citrate. The chelate-biotin conjugate of Example I was added and heated to 90° C. for 30 min at a pH of about 2 to 3. The solution was neutralized to a pH of about 6 to about 8, and yielded an $N_3S$-coordinated $^{186}$Re-chelate-biotin conjugate. C-18 HPLC gradient elution using 5–60% acetonitrile in 1% acetic acid resulted in radiochemical yields of 85–90%. Subsequent purification over a C-18 reverse phase hydrophobic column yielded material of 99% purity.

EXAMPLE III

In Vitro Analysis of Radiolabeled Chelate-Biotin Conjugates

Both the $^{99m}$Tc- and $^{186}$Re-chelate-biotin conjugates were evaluated in vitro. When combined with excess avidin (about 100-fold molar excess), 100% of both radiolabeled biotin conjugates complexed with avidin.

A $^{99m}$Tc-biotin conjugate was subjected to various chemical challenge conditions. Briefly, $^{99m}$Tc-chelate-biotin conjugates were combined with avidin and passed over a 5 cm size exclusion gel filtration column. The radiolabeled biotin-avidin complexes were subjected to various chemical challenges (see Table 1), and the incubation mixtures were centrifuged through a size exclusion filter. The percent of radioactivity retained (indicating avidin-biotin-associated radiolabel) is presented in Table 1. Thus, upon chemical challenge, the radiometal remained associated with the macromolecular complex.

TABLE 1

Chemical Challenge of $^{99m}$Tc-Chelate-Biotin-Avidin Complexes

| Challenge Medium | pH | % Radioactivity Retained 1 h, 37° C. | 18 h, RT |
|---|---|---|---|
| PBS | 7.2 | 99 | 99 |
| Phosphate | 8.0 | 97 | 97 |
| 10 mM cysteine | 8.0 | 92 | 95 |
| 10 mM DTPA | 8.0 | 99 | 98 |
| 0.2 M carbonate | 10.0 | 97 | 94 |

In addition, each radiolabeled biotin conjugate was incubated at about 50 μg/ml with serum; upon completion of the incubation, the samples were subjected to instant thin layer chromatography (ITLC) in 80% methanol. Only 2–4% of the radioactivity remained at the origin (i.e., associated with protein); this percentage was unaffected by the addition of exogenous biotin. When the samples were analyzed using size exclusion H-12 FPLC with 0.2M phosphate as mobile phase, no association of radioactivity with serum macromolecules was observed.

Each radiolabeled biotin conjugate was further examined using a competitive biotin binding assay. Briefly, solutions containing varying ratios of D-biotin to radiolabeled biotin conjugate were combined with limiting avidin at a constant total biotin:avidin ratio. Avidin binding of each radiolabeled biotin conjugate was determined by ITLC, and was compared to the theoretical maximum stoichiometric binding (as determined by the HABA spectrophotometric assay of Green, *Biochem. J.* 94:23c–24c, 1965). No significant difference in avidin binding was observed between each radiolabeled biotin conjugate and D-biotin.

EXAMPLE IV

In Vivo Analysis of Radiolabeled Chelate-Biotin Conjugates Administered After Antibody Pretargeting The $^{186}$Re-chelate-biotin conjugate of Example I was studied in an animal model of a three-step antibody pretargeting protocol. Generally, this protocol involved: (i) prelocalization of biotinylated monoclonal antibody; (ii) administration of avidin for formation of a "sandwich" at the target site and for clearance of residual circulating biotinylated antibody; and (iii) administration of the $^{186}$Re-biotin conjugate for target site localization and rapid blood clearance.

A. Preparation and Characterization of Biotinylated Antibody

Biotinylated NR-LU-10 was prepared according to either of the following procedures. The first procedure involved derivitization of antibody via lysine ε-amino groups. NR-LU-10 was radioiodinated at tyrosines using chloramine T and either $^{125}$I or $^{131}$I sodium iodide. The radioiodinated antibody (5–10 mg/ml) was then biotinylated using biotinamido caproate NHS ester in carbonate buffer, pH 8.5, containing 5% DMSO according to the scheme below.

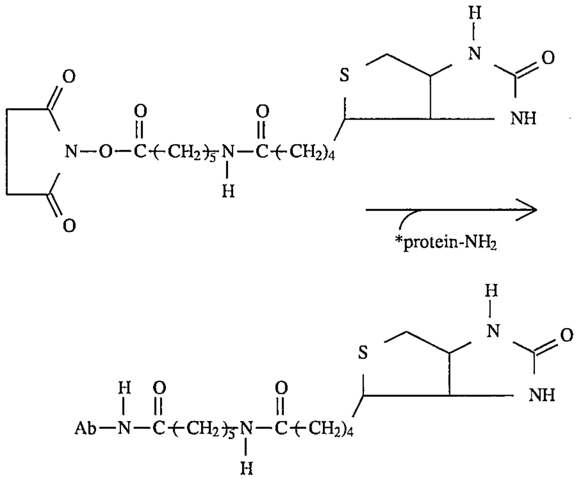

The impact of lysine biotinylation on antibody immunoreactivity was examined. As the molar offering of biotin:antibody increased from 5:1 to 40:1, biotin incorporation increased as expected (measured using the HABA assay and pronase-digested product) (Table 2, below). Percent of biotinylated antibody immunoreactivity as compared to native antibody was assessed in a limiting antigen ELISA assay. The immunoreactivity percentage dropped below 70% at a measured derivitization of 11.1:1; however, at this level of derivitization, no decrease was observed in antigen-positive cell binding (performed with LS-180 tumor cells at antigen excess). Subsequent experiments used antibody derivitized at a biotin:antibody ratio of 10:1.

TABLE 2

Effect of Lysine Biotinylation on Immunoreactivity

| Molar Offering (Biotins/Ab) | Measured Derivitization (Biotins/Ab) | Immunoassessment (%) ELISA | Immunoassessment (%) Cell Binding |
|---|---|---|---|
| 5:1 | 3.4 | 86 | |
| 10:1 | 8.5 | 73 | 100 |
| 13:1 | 11.1 | 69 | 102 |
| 20:1 | 13.4 | 36 | 106 |
| 40:1 | 23.1 | 27 | |

Alternatively, NR-LU-10 was biotinylated using thiol groups generated by reduction of cystines. Derivitization of thiol groups was hypothesized to be less compromising to antibody immunoreactivity. NR-LU-10 was radioiodinated using p-aryltin phenylate NHS ester (PIP-NHS) and either $^{125}$I or $^{131}$I sodium iodide. Radioiodinated NR-LU-10 was incubated with 25 mM dithiothreitol and purified using size exclusion chromatography. The reduced antibody (containing free thiol groups) was then reacted with a 10- to 100-fold molar excess of N-iodoacetyl-n'-biotinyl hexylene diamine in phosphate-buffered saline (PBS), pH 7.5, containing 5% DMSO (v/v).

TABLE 3

Effect of Thiol Biotinylation on Immunoreactivity

| Molar Offering (Biotins/Ab) | Measured Derivitization (Biotins/Ab) | Immunoassessment (%) ELISA | Immunoassessment (%) Cell Binding |
|---|---|---|---|
| 10:1 | 4.7 | 114 | |
| 50:1 | 6.5 | 102 | 100 |
| 100:1 | 6.1 | 95 | 100 |

As shown in Table 3, at a 50:1 or greater biotin:antibody molar offering, only 6 biotins per antibody were incorporated. No significant impact on immunoreactivity was observed.

The lysine- and thiol-derivitized biotinylated antibodies ("antibody (lysine)" and "antibody (thiol)", respectively) were compared. Molecular sizing on size exclusion FPLC demonstrated that both biotinylation protocols yielded monomolecular (monomeric) IgGs. Biotinylated antibody (lysine) had an apparent molecular weight of 160 kD, while biotinylated antibody (thiol) had an apparent molecular weight of 180 kD. Reduction of endogenous sulfhydryls (i.e, disulfides) to thiol groups, followed by conjugation with biotin, may produce a somewhat unfolded macromolecule. If so, the antibody (thiol) may display a larger hydrodynamic radius and exhibit an apparent increase in molecular weight by chromatographic analysis. Both biotinylated antibody species exhibited 98% specific binding to immobilized avidin-agarose.

Further comparison of the biotinylated antibody species was performed using non-reducing SDS-PAGE, using a 4% stacking gel and a 5% resolving gel. Biotinylated samples were either radiolabeled or unlabeled and were combined with either radiolabeled or unlabeled avidin or streptavidin. Samples were not boiled prior to SDS-PAGE analysis. The native antibody and biotinylated antibody (lysine) showed similar migrations; the biotinylated antibody (thiol) produced two species in the 50–75 kD range. These species may represent two thiol-capped species. Under these SDS-PAGE conditions, radiolabeled streptavidin migrates as a 60 kD tetramer. When 400 μg/ml radiolabeled streptavidin was combined with 50 μg/ml biotinylated antibody (analogous to "sandwiching" conditions in vivo), both antibody species formed large molecular weight complexes. However, only the biotinylated antibody (thiol)-streptavidin complex moved from the stacking gel into the resolving gel, indicating a decreased molecular weight as compared to the biotinylated antibody (lysine)-streptavidin complex.

B. Blood Clearance of Biotinylated Antibody Species

Radioiodinated biotinylated NR-LU-10 (lysine or thiol) was intravenously administered to non-tumored nude mice at a dose of 100 μg. At 24 h post-administration of radioiodinated biotinylated NR-LU-10, mice were intravenously injected with either saline or 400 μg of avidin. With saline administration, blood clearances for both biotinylated antibody species were biphasic and similar to the clearance of native NR-LU-10 antibody.

In the animals that received avidin intravenously at 24 h, the biotinylated antibody (lysine) was cleared (to a level of 5% of injected dose) within 15 min of avidin administration (avidin:biotin=10:1). With the biotinylated antibody (thiol), avidin administration (10:1 or 25:1) reduced the circulating antibody level to about 35% of injected dose after two hours. Residual radiolabeled antibody activity in the circulation after avidin administration was examined in vitro using immobilized biotin. This analysis revealed that 85% of the biotinylated antibody was complexed with avidin. These data suggest that the biotinylated antibody (thiol)-avidin complexes that were formed were insufficiently cross-linked to be cleared by the RES.

Blood clearance and biodistribution studies of biotinylated antibody (lysine) 2 h post-avidin or post-saline administration were performed. Avidin administration significantly reduced the level of biotinylated antibody in the blood (see FIG. 1), and increased the level of biotinylated antibody in the liver and spleen. Kidney levels of biotinylated antibody were similar.

EXAMPLE V

In Vivo Characterization of $^{186}$Re-Chelate-Biotin Conjugates In a Three-Step Pretargeting Protocol A $^{186}$Re-chelate-biotin conjugate of Example I (MW≈1000; specific activity=1–2 mCi/mg) was examined in a three-step pretargeting protocol in an animal model. More specifically, 18–22 g female nude mice were implanted subcutaneously with LS-180 human colon tumor xenografts, yielding 100–200 mg tumors within 10 days of implantation.

NR-LU-10 antibody (MW≈150 kD) was radiolabeled with $^{125}$I/Chloramine T and biotinylated via lysine residues (as described in Example IV.A, above). Avidin (MW≈66 kD) was radiolabeled with $^{131}$I/PIP-NHS (as described for radioiodination of NR-LU-10 in Example IV.A., above). The experimental protocol was as follows:

| | |
|---|---|
| Group 1: | Time 0, inject 100 μg $^{125}$I-labeled, biotinylated NR-LU-10<br>Time 24 h, inject 400 μg $^{131}$I-labeled avidin<br>Time 26 h, inject 60 μg $^{186}$Re-chelate-biotin conjugate |
| Group 2: (control) | Time 0, inject 400 μg $^{131}$I-labeled avidin<br>Time 2 h, inject 60 μg $^{186}$Re-chelate-biotin conjugate |
| Group 3: (control) | Time 0, inject 60 μg $^{186}$Re-chelate-biotin conjugate |

The three radiolabels employed in this protocol are capable of detection in the presence of each other. It is also noteworthy that the sizes of the three elements involved are logarithmically different—antibody≅150,000; avidin≅66,000; and biotin≅1,000. Biodistribution analyses were performed at 2, 6, 24, 72 and 120 h after administration of the $^{186}$Re-chelate-biotin conjugate.

Certain preliminary studies were performed in the animal model prior to analyzing the $^{186}$Re-chelate-biotin conjugate in a three-step pretargeting protocol. First, the effect of biotinylated antibody on blood clearance of avidin was examined. These experiments showed that the rate and extent of avidin clearance was similar in the presence or absence of biotinylated antibody. Second, the effect of biotinylated antibody and avidin on blood clearance of the $^{186}$Re-chelate-biotin conjugate was examined; blood clearance was similar in the presence or absence of biotinylated antibody and avidin. Further, antibody immunoreactivity was found to be uncompromised by biotinylation at the level tested.

Third, tumor uptake of biotinylated antibody administered at time 0 or of avidin administered at time 24 h was examined. The results of this experimentation are shown in FIG. 1. At 25 h, about 350 pmol/g biotinylated antibody was present at the tumor; at 32 h the level was about 300 pmol/g; at 48 h, about 200 pmol/g; and at 120 h, about 100 pmol/g. Avidin uptake at the same time points was about 250, 150, 50 and 0 pmol/g, respectively. From the same experiment, tumor to blood ratios were determined for biotinylated antibody and for avidin. From 32 h to 120 h, the ratios of tumor to blood were very similar.

Rapid and efficient removal of biotinylated antibody from the blood by complexation with avidin was observed. Within two hours of avidin administration, a 10-fold reduction in blood pool antibody concentration was noted (FIG. 1), resulting in a sharp increase in tumor to blood ratios. Avidin is cleared rapidly, with greater than 90% of the injected dose cleared from the blood within 1 hour after administration. The Re-186-biotin chelate is also very rapidly cleared, with greater than 99% of the injected dose cleared from the blood by 1 hour after administration.

The three-step pretargeting protocol (described for Group 1, above) was then examined. More specifically, tumor uptake of the $^{186}$Re-chelate-biotin conjugate in the presence or absence of biotinylated antibody and avidin was determined. In the absence of biotinylated antibody and avidin, the $^{186}$Re-chelate-biotin conjugate displayed a slight peak 2 h post-injection, which was substantially cleared from the tumor by about 5 h. In contrast, at 2 h post-injection in the presence of biotinylated antibody and avidin (specific), the $^{186}$Re-chelate-biotin conjugate reached a peak in tumor approximately 7 times greater than that observed in the absence of biotinylated antibody and avidin. Further, the specifically bound $^{186}$Re-chelate-biotin conjugate was retained at the tumor at significant levels for more than 50 h. Tumor to blood ratios determined in the same experiment increased significantly over time (i.e., T:B=≈8 at 30 h; 15 at 100 h; ≈35 at 140 h).

Tumor uptake of the $^{186}$Re-chelate-biotin conjugate has further been shown to be dependent on the dose of biotinylated antibody administered. At 0 μg of biotinylated antibody, about 200 pmol/g of $^{186}$Re-chelate-biotin conjugate was present at the tumor at 2 h after administration; at 50 μg antibody, about 500 pmol/g of $^{186}$Re-chelate-biotin conjugate; and at 100 μg antibody, about 1,300 pmol/g of $^{186}$Re-chelate-biotin conjugate.

Figure 2:
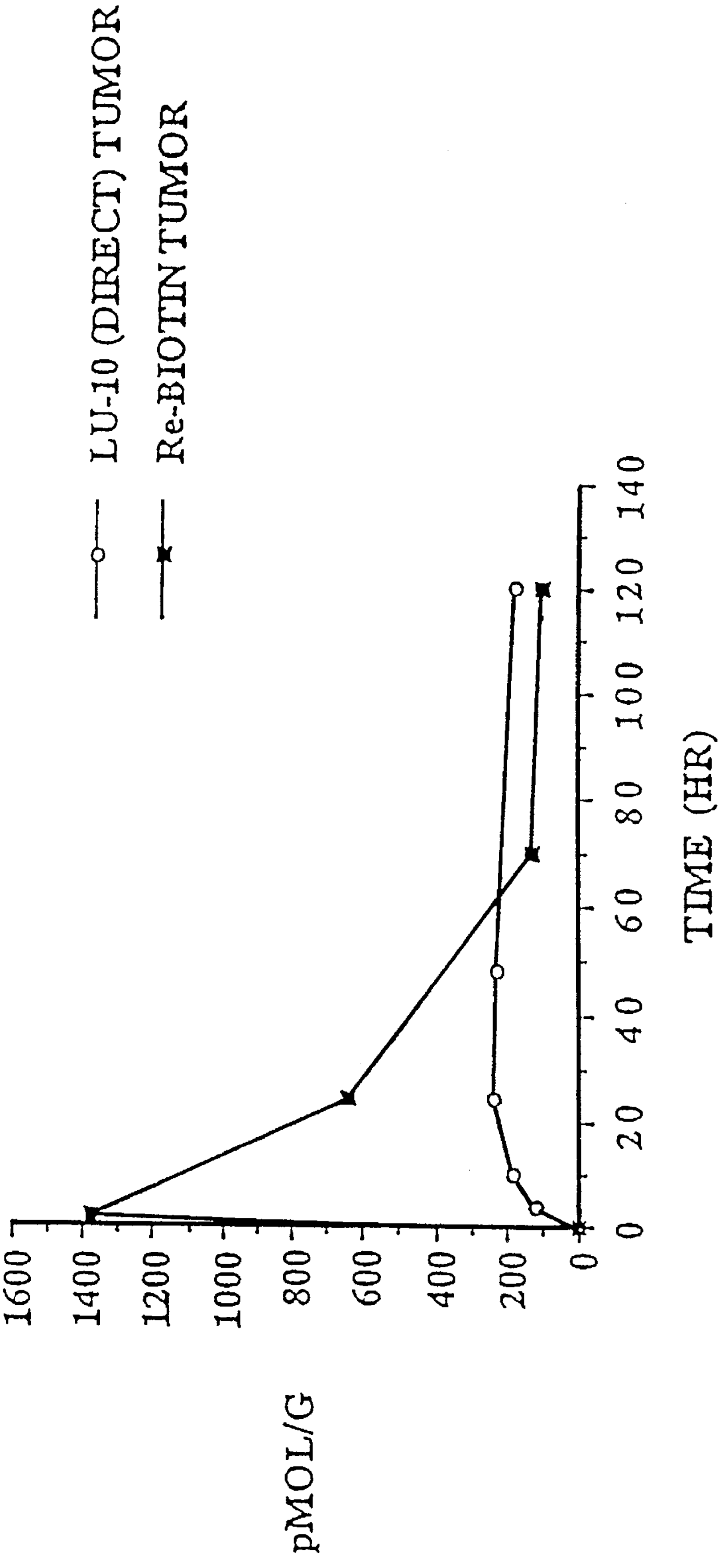
FIG. 2 depicts radiorhenium tumor uptake in a three-step pretargeting protocol, as compared to administration of radiolabeled antibody (conventional means involving antibody that is covalently linked to chelated radiorhenium).

Rhenium tumor uptake via the three-step pretargeting protocol was compared to tumor uptake of the same antibody radiolabeled through chelate covalently attached to the antibody (conventional procedure). The results of this comparison are depicted in FIG. 2. Blood clearance and tumor uptake were compared for the chelate directly labeled rhenium antibody conjugate and for the three-step pretargeted sandwich. Areas under the curves (AUC) and the ratio of $AUC_{tumor}/AUC_{blood}$ were determined. For the chelate directly labeled rhenium antibody conjugate, the ratio of $AUC_{tumor}/AUC_{blood}$=24055/10235 or 2.35; for the three-step pretargeted sandwich, the ratio of $AUC_{tumor}/AUC_{blood}$=46764/6555 or 7.13.

Tumor uptake results are best taken in context with radioactivity exposure to the blood compartment, which directly correlates with bone marrow exposure. Despite the fact that 100-fold more rhenium was administered to animals in the three-step protocol, the very rapid clearance of the small molecule (Re-186-biotin) from the blood minimizes the exposure to Re-186 given in this manner. In the same matched antibody dose format, direct labeled (conventional procedure) NR-LU-10 whole antibody yielded greater exposure to rhenium than did the 100-fold higher dose given in the three-step protocol. A clear increase in the targeting ratio (tumor exposure to radioactivity:blood exposure to radioactivity—$AUC_{tumor}:AUC_{blood}$) was observed for three-step pretargeting (approximately 7:1) in comparison to the direct labeled antibody approach (approximately 2.4:1).

EXAMPLE VI

Preparation of Chelate-Biotin Conjugates Having Improved Biodistribution Properties The biodistribution of $^{111}$In-labeled-biotin derivatives varies greatly with structural changes in the chelate and the conjugating group. Similar structural changes may affect the biodistribution of technetium- and rhenium-biotin conjugates. Accordingly, methods for preparing technetium- and rhenium-biotin conjugates having optimal clearance from normal tissue are advantageous.

A. Neutral MAMA Chelate/Conjugate

A neutral MAMA chelate-biotin conjugate is prepared according to the following scheme.

a) MAMA ligand

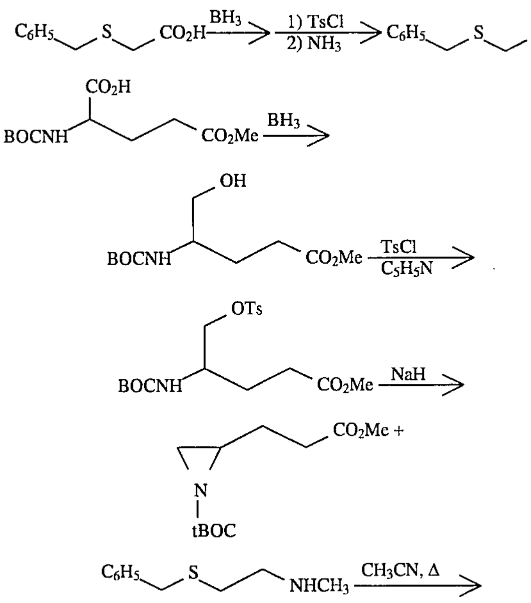

-continued

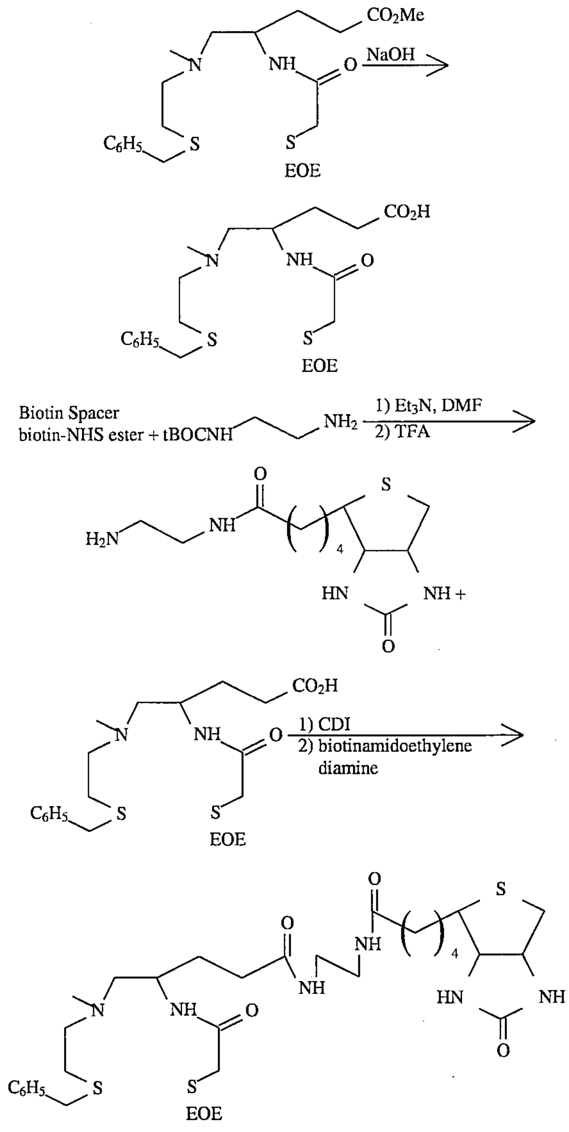

The resultant chelate-biotin conjugate shows superior kidney excretion. Although the net overall charge of the conjugate is neutral, the polycarboxylate nature of the molecule generates regions of hydrophilicity and hydrophobicity. By altering the number and nature of the carboxylate groups within the conjugate, excretion may be shifted from kidney to gastrointestinal routes. For instance, neutral compounds are generally cleared by the kidneys; anionic compounds are generally cleared through the GI system.

B. Polylysine Derivitization

Conjugates containing polylysine may also exhibit beneficial biodistribution properties. With whole antibodies, derivitization with polylysine may skew the biodistribution of conjugate toward liver uptake. In contrast, derivitization of Fab fragments with polylysine results in lower levels of both liver and kidney uptake; blood clearance of these conjugates is similar to that of Fab covalently linked to chelate. An exemplary polylysine derivitized chelate-biotin conjugate is illustrated below.

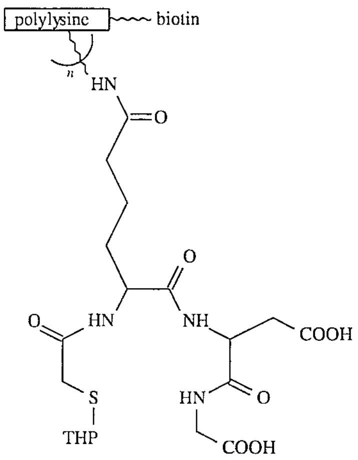

Inclusion of polylysine in radiometal-chelate-biotin conjugates is therefore useful for minimizing or eliminating RES sequestration while maintaining good liver and kidney clearance of the conjugate. For improved renal excretion properties, polylysine derivatives are preferably succinylated following biotinylation. Polylysine derivatives offer the further advantages of: (1) increasing the specific activity of the radiometal-chelate-biotin conjugate; (2) permitting control of rate and route of blood clearance by varying the molecular weight of the polylysine polymer; and (3) increasing the circulation half-life of the conjugate for optimal tumor interaction.

Polylysine derivitization is accomplished by standard methodologies. Briefly, poly-L-lysine is acylated according to standard amino group acylation procedures (aqueous bicarbonate buffer, pH 8, added biotin-NHS ester, followed by chelate NHS ester). Alternative methodology involves anhydrous conditions using nitrophenyl esters in DMSO and triethyl amine. The resultant conjugates are characterized by UV and NMR spectra.

The number of biotins attached to polylysine is determined by the HABA assay. Spectrophotometric titration is used to assess the extent of amino group derivitization. The radiometal-chelate-biotin conjugate is characterized by size exclusion.

C. Cleavable Linkage

Through insertion of a cleavable linker between the chelate and biotin portion of a radiometal-chelate-biotin conjugate, retention of the conjugate at the tumor relative to normal tissue may be enhanced. More specifically, linkers that are cleaved by enzymes present in normal tissue but deficient or absent in tumor tissue can increase tumor retention. As an example, the kidney has high levels of γ-glutamyl transferase; other normal tissues exhibit in vivo cleavage of γ-glutamyl prodrugs. In contrast, tumors are generally deficient in enzyme peptidases. The glutamyl-linked biotin conjugate depicted below is cleaved in normal tissue and retained in the tumor.

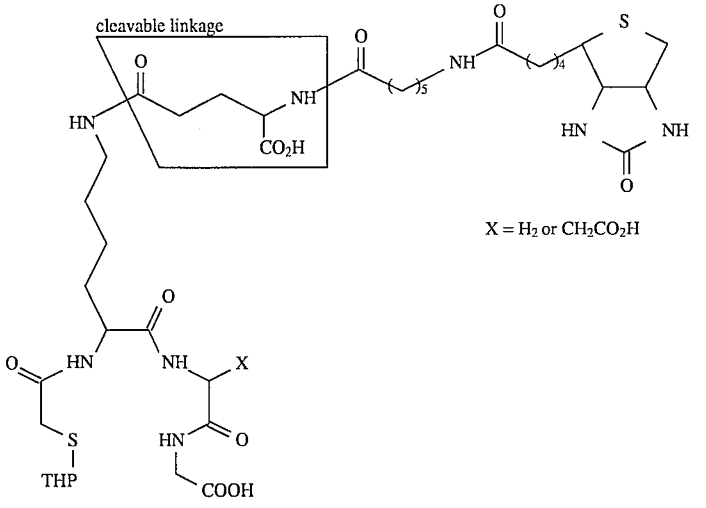

X = $H_2$ or $CH_2CO_2H$

D. Serine Linker With O-Polar Substituent

Sugar substitution of $N_3S$ chelates renders such chelates water soluble. Sulfonates, which are fully ionized at physiological pH, improve water solubility of the chelate-biotin conjugate depicted below.

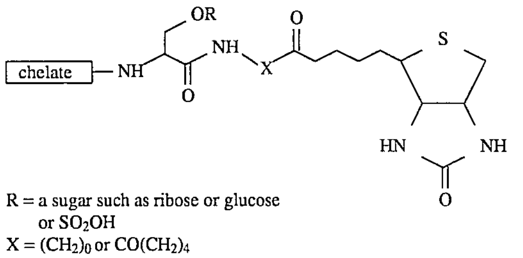

R = a sugar such as ribose or glucose or $SO_2OH$
X = $(CH_2)_0$ or $CO(CH_2)_4$ This compound is synthesized according to the standard reaction procedures. Briefly, biocytin is condensed with N-t-BOC-(O-sulfonate or O-glucose) serine NHS ester to give N-t-BOC-(O-sulfonate or O-glucose) serine biocytinamide. Subsequent cleavage of the N-t-BOC group with TFA and condensation with ligand NHS ester in DMF with triethylamine provides ligand-amidoserine (O-sulfonate or O-glucose) biocytinamide.

EXAMPLE VII

Preparation and Characterization of PIP-Radioiodinated Biotin

Radioiodinated biotin derivatives prepared by exposure of poly-L-lysine to excess NHS-LC-biotin and then to Bolton-Hunter N-hydroxysuccinimide esters in DMSO has been reported. After purification, this product was radiolabeled by the iodogen method (see, for instance, Del Rosario et al., *J. Nucl. Med.* 32:5, 1991, 993 (abstr.)). Because of the high molecular weight of the resultant radioiodinated biotin derivative, only limited characterization of product (i.e., radio-HPLC and binding to immobilized streptavidin) was possible.

Preparation of radioiodinated biotin according to the present invention provides certain advantages. First, the radioiodobiotin derivative is a low molecular weight compound that is amenable to complete chemical characterization. Second, the disclosed methods for preparation involve a single step and eliminate the need for a purification step.

Briefly, iodobenzamide derivatives corresponding to biocytin (R=COOH) and biotinamidopentylamine (R=H) were prepared according to the following scheme. In this scheme, "X" may be any radiohalogen, including $^{125}I$, $^{131}I$, $^{123}I$, $^{211}At$ and the like.

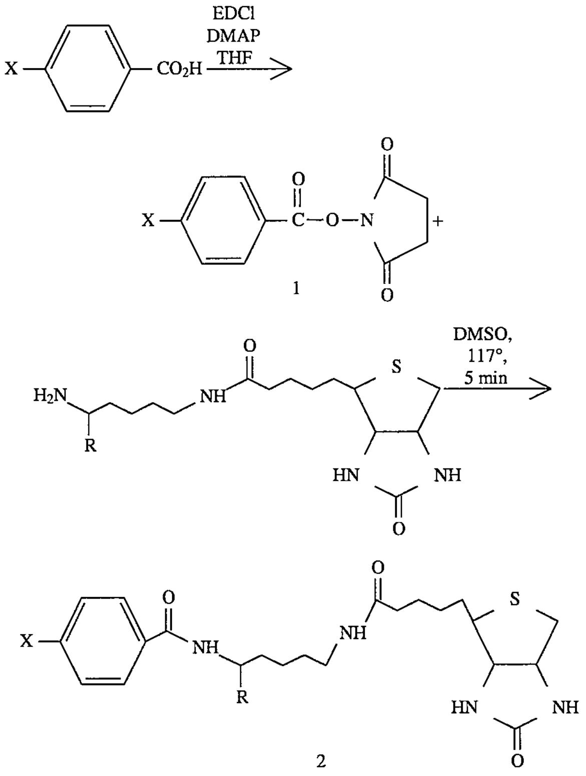

1

2

Preparation of 1 was generally according to Wilbur et al., *J. Nucl. Med.* 30:216–26, 1989, using a tributyltin intermediate. Water soluble carbodiimide was used in the above-depicted reaction, since the NHS ester 1 formed intractable mixtures with DCU. The NHS ester was not compatible with chromatography; it was insoluble in organic and aqueous solvents and did not react with biocytin in DMF or in buffered aqueous acetonitrile. The reaction between 1 and biocytin or 5-(biotinamido) pentylamine was sensitive to base. When the reaction of 1 and biocytin or the pentylamine was performed in the presence of triethylamine in hot DMSO, formation of more than one biotinylated product resulted. In contrast, the reaction was extremely clean and complete when a suspension of and biocytin (4 mg/ml) or the pentylamine (4 mg/ml) was heated in DMSO at 117° C. for about 5 to about 10 min. The resultant $^{125}$I-biotin derivatives were obtained in 94% radiochemical yield. Optionally, the radioiodinated products may be purified using C-18 HPLC and a reverse phase hydrophobic column. Hereinafter, the resultant radioiodinated products 2 are referred to as PIP-biocytin (R═COOH) and PIP-pentylamine (R═H).

Both iodobiotin derivatives 2 exhibited ≧95% binding to immobilized avidin. Incubation of the products 2 with mouse serum resulted in no loss of the ability of 2 to bind to immobilized avidin. Biodistribution studies of 2 in male BALB/c mice showed rapid clearance from the blood (similar to $^{186186}$Re-chelate-biotin conjugates described above). The radioiodobiotin 2 had decreased hepatobiliary excretion as compared to the $^{186}$Re-chelate-biotin conjugate; urinary excretion was increased as compared to the $^{186}$Re-chelate-biotin conjugate. Analysis of urinary metabolites of 2 indicated deiodination and cleavage of the biotin amide bond; the metabolites showed no binding to immobilized avidin. In contrast, metabolites of the $^{186}$Re-chelate-biotin conjugate appear to be excreted in urine as intact biotin conjugates. Intestinal uptake of 2 is <50% that of the $^{186}$Re-chelate-biotin conjugate. These biodistribution properties of provided enhanced whole body clearance of radioisotope and indicate the advantageous use of 2 within pretargeting protocols.

$^{131}$I-PIP-biocytin was evaluated in a two-step pretargeting procedure in tumor-bearing mice. Briefly, female nude mice were injected subcutaneously with LS-180 tumor cells; after 7 d, the mice displayed 50–100 mg tumor xenografts. At t=0, the mice were injected with 200 μg of NR-LU-10 -avidin conjugate labeled with $^{125}$I using PIP-NHS (see Example IV.A.). At t=36 h, the mice received 42 μg of $^{131}$I-PIP-biocytin. The data showed immediate, specific tumor localization, corresponding to ≈1.5 $^{131}$I-PIP-biocytin molecules per avidin molecule.

The described radiohalogenated biotin compounds are amenable to the same types of modifications described in Example VI above for $^{186}$Re-chelate-biotin conjugates. In particular, the following PIP-polylysine-biotin molecule is made by trace labeling polylysine with $^{125}$I-PIP, followed by extensive biotinylation of the polylysine.

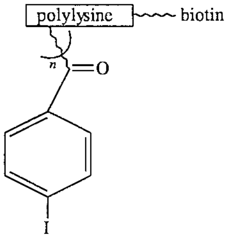

Assessment of $^{125}$I binding to immobilized avidin ensures that all radioiodinated species also contain at least an equivalent of biotin.

EXAMPLE VIII

Preparation of Biotinylated Antibody (Thiol) Through Endogenous Antibody Sulfhydryl Groups Or Sulfhydryl-Generating Compounds Certain antibodies have available for reaction endogenous sulfhydryl groups. If the antibody to be biotinylated contains endogenous sulfhydryl groups, such antibody is reacted with N-iodoacetyl-n'-biotinyl hexylene diamine (as described in Example IV.A., above). The availability of one or more endogenous sulfhydryl groups obviates the need to expose the antibody to a reducing agent, such as DTT, which can have other detrimental effects on the biotinylated antibody.

Alternatively, one or more sulfhydryl groups are attached to a targeting moiety through the use of chemical compounds or linkers that contain a terminal sulfhydryl group. An exemplary compound for this purpose is iminothiolane. As with endogenous sulfhydryl groups (discussed above), the detrimental effects of reducing agents on antibody are thereby avoided.

EXAMPLE IX

Two-Step Pretargeting Methodology That Does Not Induce Internalization

A NR-LU-13-avidin conjugate is prepared as follows. Initially, avidin is derivitized with N-succinimidyl 4-(N-maleimidomethyl)cyclohexane-1-carboxylate (SMCC). SMCC-derived avidin is then incubated with NR-LU-13 in a 1:1 molar ratio at pH 8.5 for 16 h. Unreacted NR-LU-13 and SMCC-derived avidin are removed from the mixture using preparative size exclusion HPLC. Two conjugates are obtained as products—the desired 1:1 NR-LU-13-avidin conjugate as the major product; and an incompletely characterized component as the minor product.

A $^{99m}$Tc-chelate-biotin conjugate is prepared as in Example II, above. The NR-LU-13-avidin conjugate is administered to a recipient and allowed to clear from the circulation. One of ordinary skill in the art of radioimmunoscintigraphy is readily able to determine the optimal time for NR-LU-13-avidin conjugate tumor localization and clearance from the circulation. At such time, the $^{99m}$Tc-chelate-biotin conjugate is administered to the recipient. Because the $^{99m}$Tc-chelate-biotin conjugate has a molecular weight of≈1,000, cross-linking of NR-LU-13-avidin molecules on the surface of the tumor cells is dramatically reduced or eliminated. As a result, the $^{99m}$Tc diagnostic agent is retained at the tumor cell surface for an extended period of time. Accordingly, detection of the diagnostic agent by imaging techniques is optimized; further, a lower dose of radioisotope provides an image comparable to that resulting from the typical three-step pretargeting protocol.

Optionally, clearance of NR-LU-13-avidin from the circulation may be accelerated by plasmapheresis in combination with a biotin affinity column. Through use of such column, circulating NR-LU-13-avidin will be retained extracorporeally, and the recipient's immune system exposure to a large, proteinaceous immunogen (i.e., avidin) is minimized.

Exemplary methodology for plasmapheresis/column purification useful in the practice of the present invention is discussed in the context of reducing radiolabeled antibody titer in imaging and in treating tumor target sites in U.S. Pat. No. 5,078,673. Briefly, for the purposes of the present invention, an example of an extracorporeal clearance methodology may include the following steps:

administering a ligand- or anti-ligand-targeting moiety conjugate to a recipient;

after a time sufficient for localization of the administered conjugate to the target site, withdrawing blood from the recipient by, for example, plasmapheresis;

separating cellular element from said blood to produce a serum fraction and returning the cellular elements to the recipient; and reducing the titer of the administered conjugate in the serum fraction to produce purified serum;

infusing the purified serum back into the recipient.

Clearance of NR-LU-13-avidin is also facilitated by administration of a particulate-type clearing agent (e,g., a polymeric particle having a plurality of biotin molecules bound thereto). Such a particulate clearing agent preferably constitutes a biodegradable polymeric carrier having a plurality of biotin molecules bound thereto. Particulate clearing agents of the present invention exhibit the capability of binding to circulating administered conjugate and removing that conjugate from the recipient. Particulate clearing agents of this aspect of the present invention may be of any configuration suitable for this purpose. Preferred particulate clearing agents exhibit one or more of the following characteristics:

microparticulate (e.g., from about 0.5 micrometers to about 100 micrometers in diameter, with from about 0.5 to about 2 micrometers more preferred), free flowing powder structure;

biodegradable structure designed to biodegrade over a period of time between from about 3 to about 180 days, with from about 10 to about 21 days more preferred, or non-biodegradable structure;

biocompatible with the recipients physiology over the course of distribution, metabolism and excretion of the clearing agent, more preferably including biocompatible biodegradation products;

and capability to bind with one or more circulating conjugates to facilitate the elimination or removal thereof from the recipient through one or more binding moieties (preferably, the complementary member of the ligand/anti-ligand pair). The total molar binding capacity of the particulate clearing agents depends upon the particle size selected and the ligand or anti-ligand substitution ratio. The binding moieties are capable of coupling to the surface structure of the particulate dosage form through covalent or non-covalent modalities as set forth herein to provide accessible ligand or anti-ligand for binding to its previously administered circulating binding pair member.

Preferable particulate clearing agents of the present invention are biodegradable or non-biodegradable microparticulates. More preferably, the particulate clearing agents are formed of a polymer containing matrix that biodegrades by random, nonenzymatic, hydrolyric scissioning.

Polymers derived from the condensation of alpha hydroxycarboxylic acids and related lactones are more preferred for use in the present invention. A particularly preferred moiety is formed of a mixture of thermoplastic polyesters (e.g., polylactide or polyglycolide) or a copolymer of lactide and glycolide components, such as poly(lactide-co-glycolide). An exemplary structure, a random poly(DL-lactide-co-glycolide), is shown below, with the values of x and y being manipulable by a practitioner in the art to achieve desirable microparticulate properties.

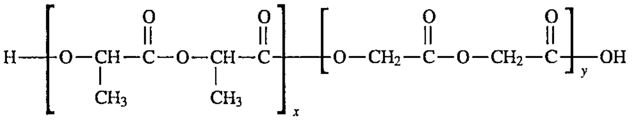

Other agents suitable for forming particulate clearing agents of the present invention include polyorthoesters and polyacetals (*Polymer Letters,* 18:293, 1980) and polyorthocarbonates (U.S. Pat. No. 4,093,709) and the like.

Preferred lactic acid/glycolic acid polymer containing matrix particulates of the present invention are prepared by emulsion-based processes, that constitute modified solvent extraction processes such as those described by Cowsar et al., "Poly(Lactide-Co-Glycolide) Microcapsules for Controlled Release of Steroids," *Methods Enzymology,* 112:101–116, 1985 (steroid entrapment in microparticulates); Eldridge et al., "Biodegradable and Biocompatible Poly(DL-Lactide-Co-Glycolide) Microspheres as an Adjuvant for Staphylococcal Enterotoxin B Toxoid Which Enhances the Level of Toxin-Neutralizing Antibodies," *Infection and Immunity,* 59:2978–2986, 1991 (toxoid entrapment); Cohen et al., "Controlled Delivery Systems for Proteins Based on Poly(Lactic/Glycolic Acid) Microspheres, " *Pharmaceutical Research,* 8(6):713–720, 1991 (enzyme entrapment); and Sanders et al., "Controlled Release of a Luteinizing Hormone-Releasing Hormone Analogue from Poly(D,L-Lactide-Co-Glycolide) Microspheres, " *J. Pharmaceutical Science*, 73(9):1294–1297, 1984 (peptide entrapment).

In general, the procedure for forming particulate clearing agents of the present invention involves dissolving the polymer in a halogenated hydrocarbon solvent and adding an additional agent that acts as solvent for the halogenated hydrocarbon solvent but not for the polymer. The polymer precipitates out from the polymer-halogenated hydrocarbon solution. Following particulate formation, they are washed and hardened with an organic solvent. Water washing and aqueous non-ionic surfactant washing steps follow, prior to drying at room temperature under vacuum.

For biocompatibility purposes, particulate clearing agents are sterilized prior to packaging, storage or administration. Sterilization may be conducted in any convenient manner therefor. For example, the particulates can be irradiated with gamma radiation, provided that exposure to such radiation does not adversely impact the structure or function of the binding moiety attached thereto. If the binding moiety is so adversely impacted, the particulate clearing agents can be produced under sterile conditions.

The preferred lactide/glycolide structure is biocompatible with the mammalian physiological environment. Also, these preferred sustained release dosage forms have the advantage that biodegradation thereof forms lactic acid and glycolic acid, both normal metabolic products of mammals.

Functional groups required for binding moiety—particulate bonding, are optionally included in the particulate structure, along with the non-degradable or biodegradable polymeric units. Functional groups that are exploitable for this purpose include those that are reactive with ligands or anti-ligands, such as carboxyl groups, amine groups, sulfhydryl groups and the like. Preferred binding enhancement moieties include the terminal carboxyl groups of the preferred (lactide-glycolide) polymer containing matrix or the like. A practitioner in the art is capable of selecting appropriate functional groups and monitoring conjugation reactions involving those functional groups.

Advantages garnered through the use of particulate clearing agents of the type described above are as follows:

particles in the "micron" size range localize in the RES and liver, with galactose derivatization or charge modification enhancement methods for this capability available, and, preferably, are designed to remain in circulation for a time sufficient to perform the clearance function;

the size of the particulates facilitates central vascular compartment retention thereof, substantially precluding equilibration into the peripheral or extravascular compartment;

desired substituents for ligand or anti-ligand binding to the particulates can be introduced into the polymeric structure;

ligand- or anti-ligand-particulate linkages having desired properties (e.g., serum biotinidase resistance thereby reducing the release of biotin metabolite from a particle-biotin clearing agent) and multiple ligands or anti-ligands can be bound to the particles to achieve optimal cross-linking of circulating targeting agent-ligand or -anti-ligand conjugate and efficient clearance of cross-linked species. This advantage is best achieved when care is taken to prevent particulate aggregation both in storage and upon in vivo administration.

Clearance of NR-LU-13-avidin may also be accelerated by an arterially inserted proteinaceous or polymeric multiloop device. A catheter-like device, consisting of thin loops of synthetic polymer or protein fibers derivitized with biotin, is inserted into a major artery (e.g., femoral artery) to capture NR-LU-13-avidin. Since the total blood volume passes through a major artery every 70 seconds, the in situ clearing device is effective to reduce circulating NR-LU-13-avidin within a short period of time. This device offers the advantages that NR-LU-13-avidin is not processed through the RES; removal of NR-LU-13 avidin is controllable and measurable; and fresh devices with undiminished binding capacity are insertable as necessary. This methodology is also useful with intraarterial administration embodiments of the present invention.

An alternative procedure for clearing NR-LU-13-avidin from the circulation without induction of internalization involves administration of biotinylated, high molecular weight molecules, such as liposomes, IgM and other molecules that are size excluded from ready permeability to tumor sites. When such biotinylated, high molecular weight molecules aggregate with NR-LU-13-avidin, the aggregated complexes are readily cleared from the circulation via the RES.

EXAMPLE X

Enhancement of Therapeutic Agent Internalization Through Avidin Crosslinking The ability of multivalent avidin to crosslink two or more biotin molecules (or chelate-biotin conjugates) is advantageously used to improve delivery of therapeutic agents. More specifically, avidin cross-linking induces internalization of crosslinked complexes at the target cell surface.

Biotinylated NR-CO-04 (lysine) is prepared according to the methods described in Example IV.A., above. Doxorubicin-avidin conjugates are prepared by standard conjugation chemistry. The biotinylated NR-CO-04 is administered to a recipient and allowed to clear from the circulation. One of ordinary skill in the art of radioimmunotherapy is readily able to determine the optimal time for biotinylated NR-CO-04 tumor localization and clearance from the circulation. At such time, the doxorubicin-avidin conjugate is administered to the recipient. The avidin portion of the doxorubicin-avidin conjugate cross-links the biotinylated NR-CO-04 on the cell surface, inducing internalization of the complex. Thus, doxorubicin is more efficiently delivered to the target cell.

In a first alternative protocol, a standard three-step pretargeting methodology is used to enhance intracellular delivery of a drug to a tumor target cell. By analogy to the description above, biotinylated NR-LU-05 is administered, followed by avidin (for blood clearance and to form the middle layer of the sandwich at the target cell-bound biotinylated antibody). Shortly thereafter, and prior to internalization of the biotinylated NR-LU-05-avidin complex, a methotrexate-biotin conjugate is administered.

In a second alternative protocol, biotinylated NR-LU-05 is further covalently linked to methotrexate. Subsequent administration of avidin induces internalization of the complex and enhances intracellular delivery of drug to the tumor target cell.

In a third alternative protocol, NR-CO-04-avidin is administered to a recipient and allowed to clear from the circulation and localize at the target site. Thereafter, a polybiotinylated species (such as biotinylated poly-L-lysine, as in Example IV.B., above) is administered. In this protocol, the drug to be delivered may be covalently attached to either the antibody-avidin component or to the polybiotinylated species. The polybiotinylated species induces internalization of the (drug)-antibody-avidin-polybiotin-(drug) complex.

EXAMPLE XI

Targeting Moiety-Anti-Ligand Conjugate for Two-Step Pretargeting In Vivo

A. Preparation of SMCC-derivitized streptavidin.

31 mg (0.48 μmol) streptavidin was dissolved in 9.0 ml PBS to prepare a final solution at 3.5 mg/ml. The pH of the solution was adjusted to 8.5 by addition of 0.9 ml of 0.5M borate buffer, pH 8.5. A DMSO solution of SMCC (3.5 mg/ml) was prepared, and 477 μl (4.8 μmol) of this solution was added dropwise to the vortexing protein solution. After 30 minutes of stirring, the solution was purified by G-25 (PD-10, Pharmacia, Piscataway, New Jersey) column chromatography to remove unreacted or hydrolyzed SMCC. The purified SMCC-derivitized streptavidin was isolated (28 mg, 1.67 mg/ml).

B. Preparation of DTT-reduced NR-LU-10. To 77 mg NR-LU-10 (0.42 μmol) in 15.0 ml PBS was added 1.5 ml of 0.5M borate buffer, pH 8.5. A DTT solution, at 400 mg/ml (165 μl) was added to the protein solution. After stirring at room temperature for 30 minutes, the reduced antibody was purified by G-25 size exclusion chromatography. Purified DTT-reduced NR-LU-10 was obtained (74 mg, 2.17 mg/ml).

C. Conjugation of SMCC-streptavidin to DTT-reduced NR-LU-10. DTT-reduced NR-LU-10 (63 mg, 29 ml, 0.42 μmol) was diluted with 44.5 ml PBS. The solution of SMCC-streptavidin (28 mg, 17 ml, 0.42 μmol) was added rapidly to the stirring solution of NR-LU-10. Total protein concentration in the reaction mixture was 1.0 mg/ml. The progress of the reaction was monitored by HPLC (Zorbax® GF-250, available from MacMod). After approximately 45 minutes, the reaction was quenched by adding solid sodium tetrathionate to a final concentration of 5 mM.

D. Purification of conjugate. For small scale reactions, monosubstituted conjugate was obtained using HPLC Zorbax (preparative) size exclusion chromatography. The desired monosubstituted conjugate product eluted at 14.0–14.5 min (3.0 ml/min flow rate), while unreacted NR-LU-10 eluted at 14.5–15 min and unreacted derivitized streptavidin eluted at 19–20 min.

For larger scale conjugation reactions, monosubstituted adduct is isolatable using DEAE ion exchange chromatography. After concentration of the crude conjugate mixture, free streptavidin was removed therefrom by eluting the column with 2.5% xylitol in sodium borate buffer, pH 8.6. The bound unreacted antibody and desired conjugate were then sequentially eluted from the column using an increasing salt gradient in 20 mM diethanolamine adjusted to pH 8.6 with sodium hydroxide.

E. Characterization of Conjugate.

1. HPLC size exclusion was conducted as described above with respect to small scale purification.

2. SDS-PAGE analysis was performed using 5% polyacrylamide gels under non-denaturing conditions. Conjugates to be evaluated were not boiled in sample buffer containing SDS to avoid dissociation of streptavidin into its 15 kD subunits. Two product bands were observed on the gel, which correspond to the mono- and di- substituted conjugates.

3. Immunoreactivity was assessed, for example, by competitive binding ELISA as compared to free antibody. Values obtained were within 10% of those for the free antibody.

4. Biotin binding capacity was assessed, for example, by titrating a known quantity of conjugate with p-[I-125]iodobenzoylbiocytin. Saturation of the biotin binding sites was observed upon addition of 4 equivalences of the labeled biocytin.

5. In vivo studies are useful to characterize the reaction product, which studies include, for example, serum clearance profiles, ability of the conjugate to target antigen-positive tumors, tumor retention of the conjugate over time and the ability of a biotinylated molecule to bind streptavidin conjugate at the tumor. These data facilitate determination that the synthesis resulted in the formation of a 1:1 streptavidin-NR-LU-10 whole antibody conjugate that exhibits blood clearance properties similar to native NR-LU-10 whole antibody, and tumor uptake and retention properties at least equal to native NR-LU-10.

Figure 3:
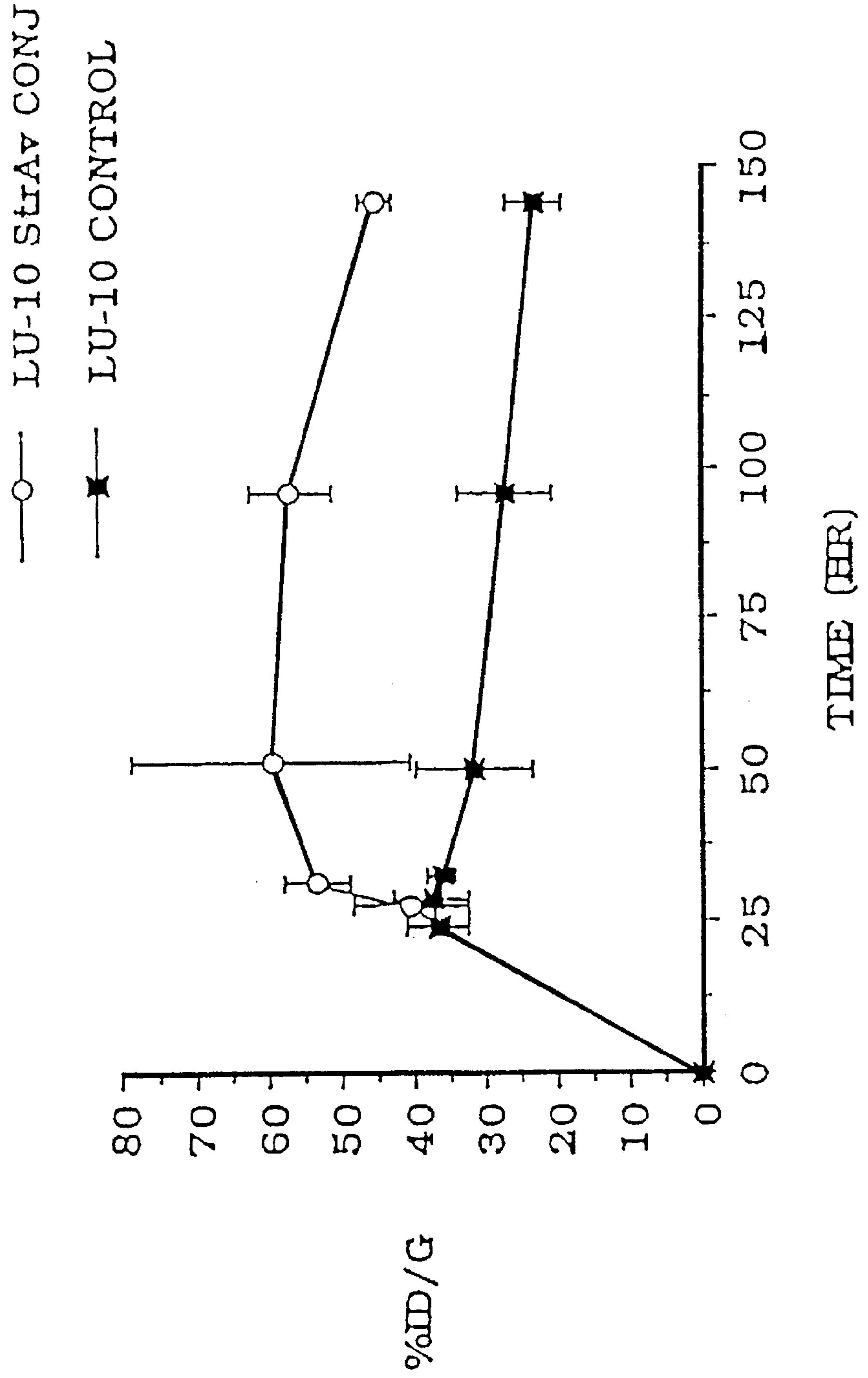
FIG. 3 depicts the tumor uptake profile of NR-LU-10-streptavidin conjugate (LU-10-StrAv) in comparison to a control profile of native NR-LU-10 whole antibody.

For example, FIG. 3 depicts the tumor uptake profile of the NR-LU-10-streptavidin conjugate (LU-10-StrAv) in comparison to a control profile of native NR-LU-10 whole antibody. LU-10-StrAv was radiolabeled on the streptavidin component only, giving a clear indication that LU-10-StrAv localizes to target cells as efficiently as NR-LU-10 whole antibody itself.

EXAMPLE XII

Two-Step Pretargeting In Vivo

A $^{186}$Re-chelate-biotin conjugate (Re-BT) of Example I (MW≈1000; specific activity=1–2 mCi/mg) and a biotin-iodine-131 small molecule, PIP-Biocytin (PIP-BT, MW approximately equal to 602; specific activity=0.5–1.0 mCi/mg), as discussed in Example VII above, were examined in a three-step pretargeting protocol in an animal model, as described in Example V above. Like Re-BT, PIP-BT has the ability to bind well to avidin and is rapidly cleared from the blood, with a serum half-life of about 5 minutes. Equivalent results were observed for both molecules in the two-step pretargeting experiments described herein.

Figure 4:
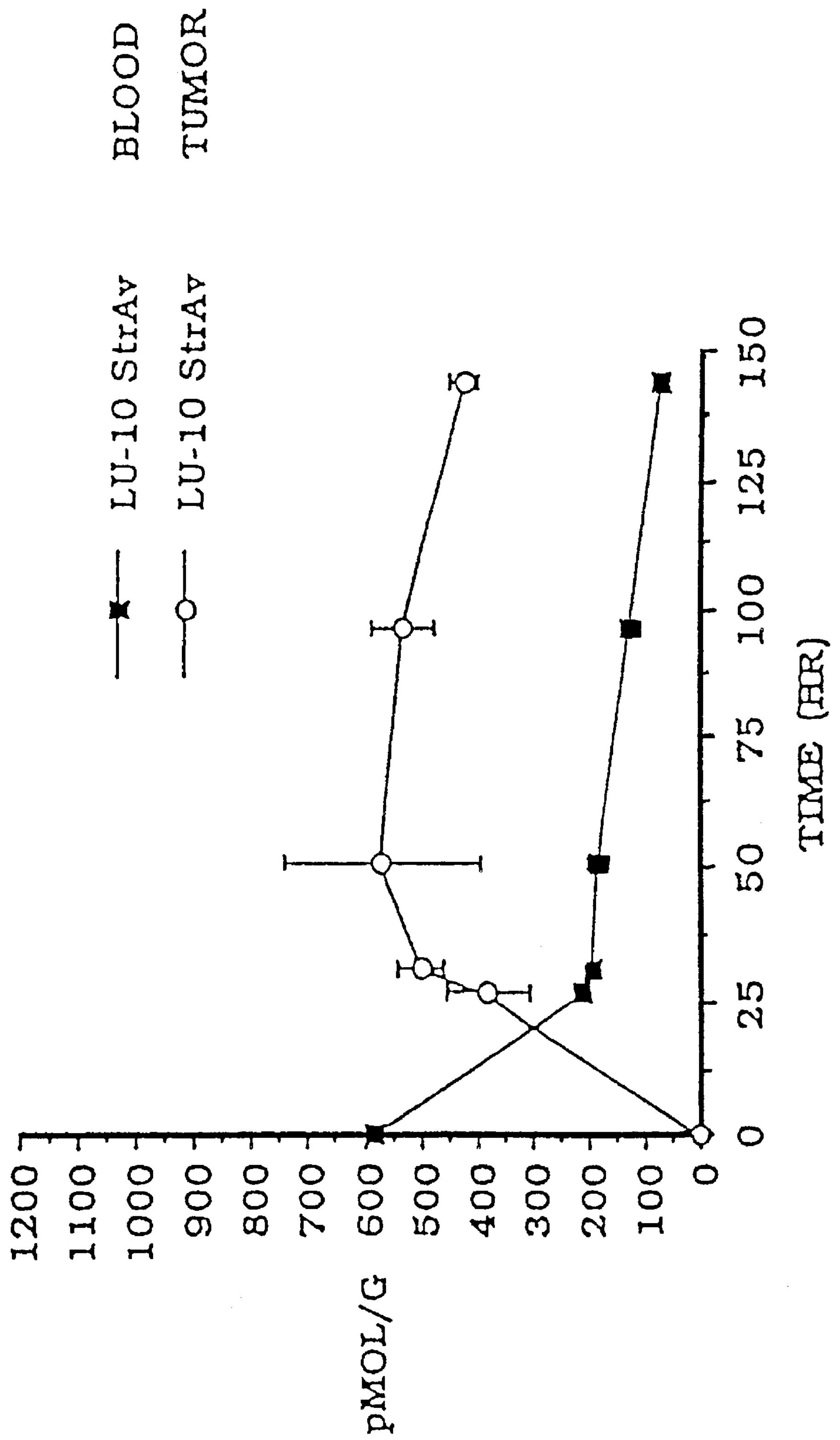
FIG. 4 depicts the tumor uptake and blood clearance profiles of NR-LU-10-streptavidin conjugate.

NR-LU-10 antibody (MW≈150 kD) was conjugated to streptavidin (MW≈66 kD) (as described in Example XI above) and radiolabeled with $^{125}$I/PIP-NHS (as described for radioiodination of NR-LU-10 in Example IV.A., above). The experimental protocol was as follows:

Time 0 inject (i.v.) 200 μg NR-LU-10-StrAv conjugate;

Time 24–48 h inject (i.v.) 60–70 fold molar excess of radiolabeled biotinyl molecule;

and perform biodistributions at 2, 6, 24, 72, 120 hours after injection of radiolabeled biotinyl molecule NR-LU-10-streptavidin has shown very consistent patterns of blood clearance and tumor uptake in the LS-180 animal model. A representative profile is shown in FIG. 4. When either PIP-BT or Re-BT is administered after allowing the LU-10-StrAv conjugate to localize to target cell sites for at least 24 hours, the tumor uptake of therapeutic radionuclide is high in both absolute amount and rapidity. For PIP-BT administered at 37 hours following LU-10-StrAv (I-125) administration, tumor uptake was above 500 pMOL/G at the 40 hour time point and peaked at about 700 pMOL/G at 45 hours post-LU-10-StrAv administration.

This almost instantaneous uptake of a small molecule therapeutic into tumor in stoichiometric amounts comparable to the antibody targeting moiety facilitates utilization of the therapeutic radionuclide at its highest specific activity. Also, the rapid clearance of radionuclide that is not bound to LU-10-StrAv conjugate permits an increased targeting ratio (tumor:blood) by eliminating the slow tumor accretion phase observed with directly labeled antibody conjugates. The pattern of radionuclide tumor retention is that of whole antibody, which is very persistent.

Experimentation using the two-step pretargeting approach and progressively lower molar doses of radiolabeled biotinyl molecule was also conducted. Uptake values of about 20% ID/G were achieved at no-carrier added (high specific activity) doses of radiolabeled biotinyl molecules. At less than saturating doses, circulating LU-10 -StrAv was observed to bind significant amounts of administered radiolabeled biotinyl molecule in the blood compartment.

EXAMPLE XIII

Asialoorosomucoid Clearing Agent and Two-Step Pretargeting

In order to maximize the targeting ratio (tumor:blood), clearing agents were sought that are capable of clearing the blood pool of targeting moiety-anti-ligand conjugate (e.g., LU-10-StrAv), without compromising the ligand binding capacity thereof at the target sites. One such agent, biotinylated asialoorosomucoid, which employs the avidin-biotin interaction to conjugate to circulating LU-10-StrAv, was tested.

A. Derivitization of orosomucoid. 10 mg human orosomucoid (Sigma N-9885) was dissolved in 3.5 ml of pH 5.5 0.1M sodium acetate buffer containing 160 mM NaCl. 70 μl of a 2% (w/v) CaCl solution in deionized (D.I.) water was added and 11 μl of neuraminidase (Sigma N-7885), 4.6 U/ml, was added. The mixture was incubated at 37° C. for 2 hours, and the entire sample was exchanged over a Centricon-10® ultrafiltration device (available from Amicon, Danvers, Mass.) with 2 volumes of PBS. The asialoorosomucoid and orosomucoid starting material were radiolabeled with I-125 using PIP technology, as described in Example IV above.

Figure 5:
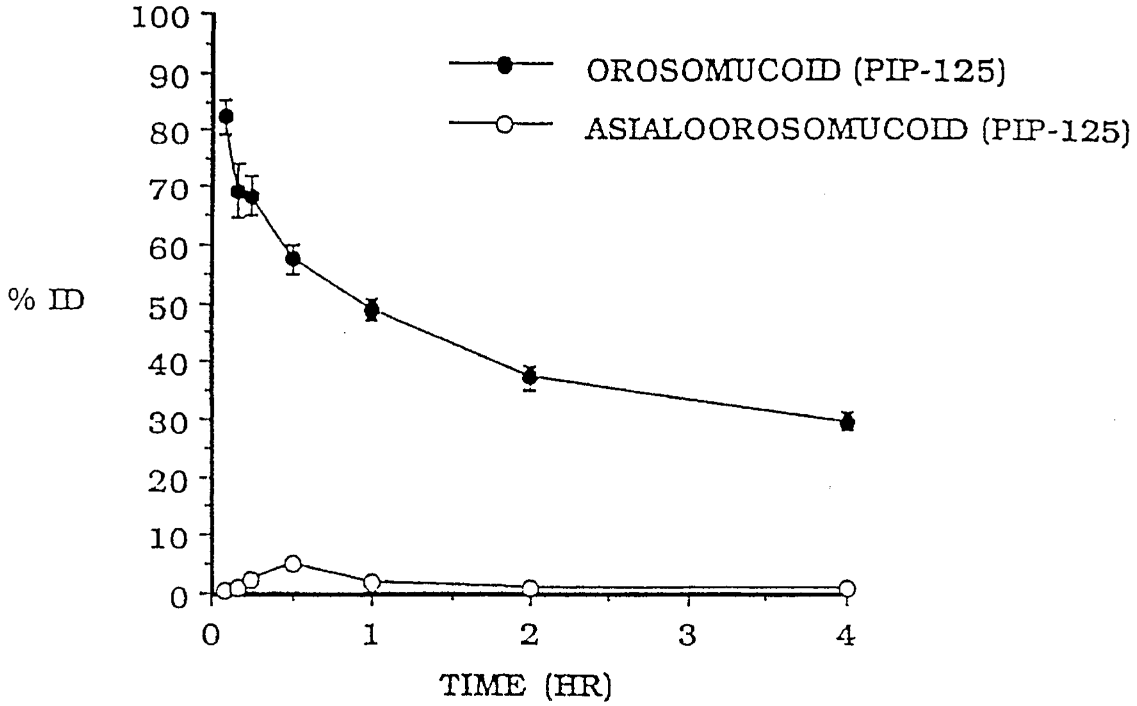
FIG. 5 depicts the rapid clearance from the blood of asialoorosomucoid in comparison with orosomucoid in terms of percent injected dose of I-125-labeled protein.

The two radiolabeled preparations were injected i.v. into female BALB/c mice (20–25 g), and blood clearance was assessed by serial retro-orbital eye bleeding of each group of three mice at 5, 10, 15 and 30 minutes, as well as at 1, 2 and 4 hours post-administration. The results of this experiment are shown in FIG. 5, with asialoorosomucoid clearing more rapidly than its orosomucoid counterpart.

Figure 6:
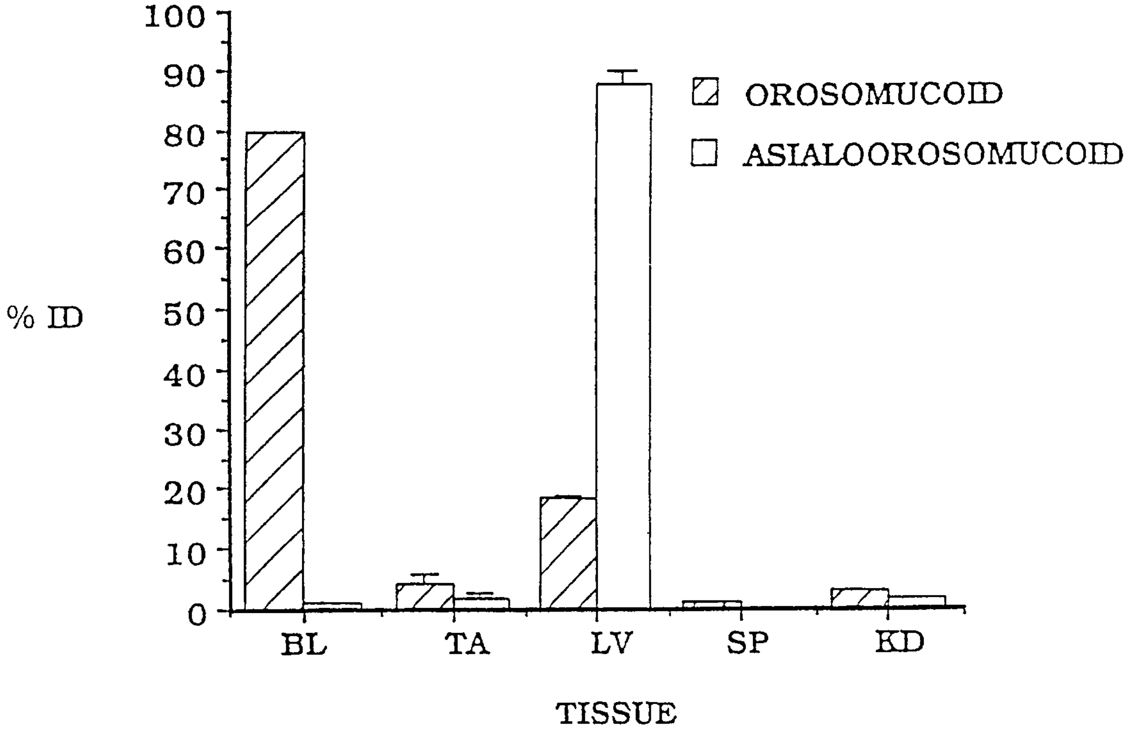
FIG. 6 depicts the 5 minute limited biodistribution of asialoorosomucoid in comparison with orosomucoid in terms of percent injected dose of I-125-labeled protein.

In addition, two animals receiving each compound were sacrificed at 5 minutes post-administration and limited biodistributions were performed. These results are shown in FIG. 6. The most striking aspects of these data are the differences in blood levels (78% for orosomucoid and 0.4% for asialoorosomucoid) and the specificity of uptake of asialoorosomucoid in the liver (86%), as opposed to other tissues.

B. Biotinylation of asialoorosomucoid clearing agent add orosomucoid control. 100 μl of 0.2M sodium carbonate buffer, pH 9.2, was added to 2 mg (in 1.00 ml PBS) of PIP-125-labeled orosomucoid and to 2 mg PIP-125-labeled asialoorosomucoid. 60 μl of a 1.85 mg/ml solution of NHS-amino caproate biotin in DMSO was then added to each compound. The reaction mixtures were vortexed and allowed to sit at room temperature for 45 minutes. The material was purified by size exclusion column chromatography (PD-10, Pharmacia) and eluted with PBS. 1.2 ml fractions were taken, with fractions 4 and 5 containing the majority of the applied radioactivity (>95%). Streptavidin-agarose beads (Sigma S-1638) or -pellets were washed with PBS, and 20 μg of each biotinylated, radiolabeled protein was added to 400 μl of beads and 400 μl of PBS, vortexed for 20 seconds and centrifuged at 14,000 rpm for 5 minutes. The supernatant was removed and the pellets were washed with 400 μl PBS. This wash procedure was repeated twice more, and the combined supernatants were assayed by placing them in a dosimeter versus their respective pellets. The values are shown below in Table 4.

TABLE 4

| Compound | Supernatant | Pellet |
|---|---|---|
| orosomucoid | 90% | 10% |
| biotin-oroso | 7.7% | 92.% |
| asialoorosomucoid | 92% | 8.0% |
| biotin-asialo | 10% | 90% |

C. Protein-Streptavidin Binding in vivo. Biotin-asialoorosomucoid was evaluated for the ability to couple with circulating LU-10-StrAv conjugate in vivo and to remove it from the blood. Female BALB/c mice (20–25 g) were injected i.v. with 200 μg LU-10-StrAv conjugate. Clearing agent (200 μl PBS—group 1; 400 μg non-biotinylated asialoorosomucoid—group 2; 400 μg biotinylated asialoorosomucoid—group 3; and 200 μg biotinylated asialoorosomucoid—group 4) was administered at 25 hours following conjugate administration. A fifth group received PIP-I-131-LU-10-StrAv conjugate which had been saturated prior to injection with biotin—group 5. The 400 μg dose constituted a 10:1 molar excess of clearing agent over the initial dose of LU-10-StrAv conjugate, while the 200 μg dose constituted a 5:1 molar excess. The saturated PIP-I-131-LU-10-StrAv conjugate was produced by addition of a 10-fold molar excess of D-biotin to 2 mg of LU-10-StrAv followed by size exclusion purification on a G-25 PD-10 column.

Three mice from each group were serially bled, as described above, at 0.17, 1, 4 and 25 hours (pre-injection of clearing agent), as well as at 27, 28, 47, 70 and 90 hours. Two additional animals from each group were sacrificed at 2 hours post-clearing agent administration and limited biodistributions were performed.

Figure 7:
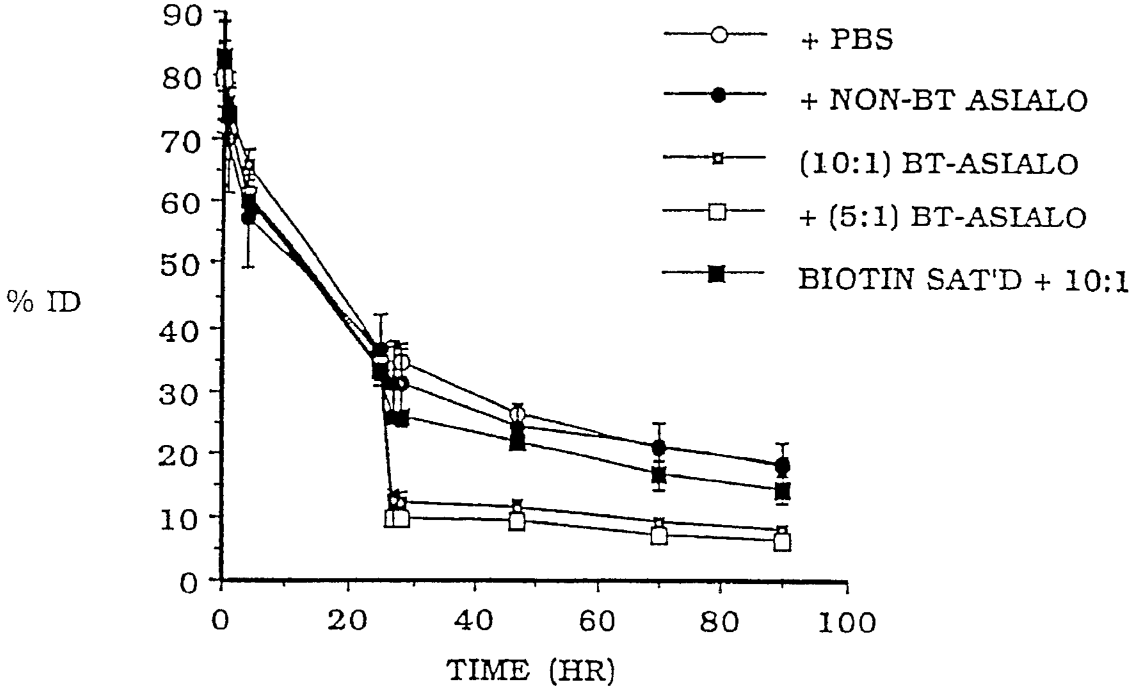
FIG. 7 depicts NR-LU-10-streptavidin conjugate blood clearance upon administration of three controls (○, ●, ■) and two doses of a clearing agent (☆, □) at 25 hours post-conjugate administration.

The blood clearance data are shown in FIG. 7. These data indicate that circulating LU-10-StrAv radioactivity in groups 3 and 4 was rapidly and significantly reduced, in comparison to those values obtained in the control groups 1, 2 and 5. Absolute reduction in circulating antibody-streptavidin conjugate was approximately 75% when compared to controls.

Biodistribution data are shown in tabular form in FIG. 8. The biodistribution data show reduced levels of conjugate for groups 3 and 4 in all tissues except the liver, kidney and intestine, which is consistent with the processing and excretion of radiolabel associated with the conjugate after complexation with biotinylated asialoorosomucoid.

Figure 9:
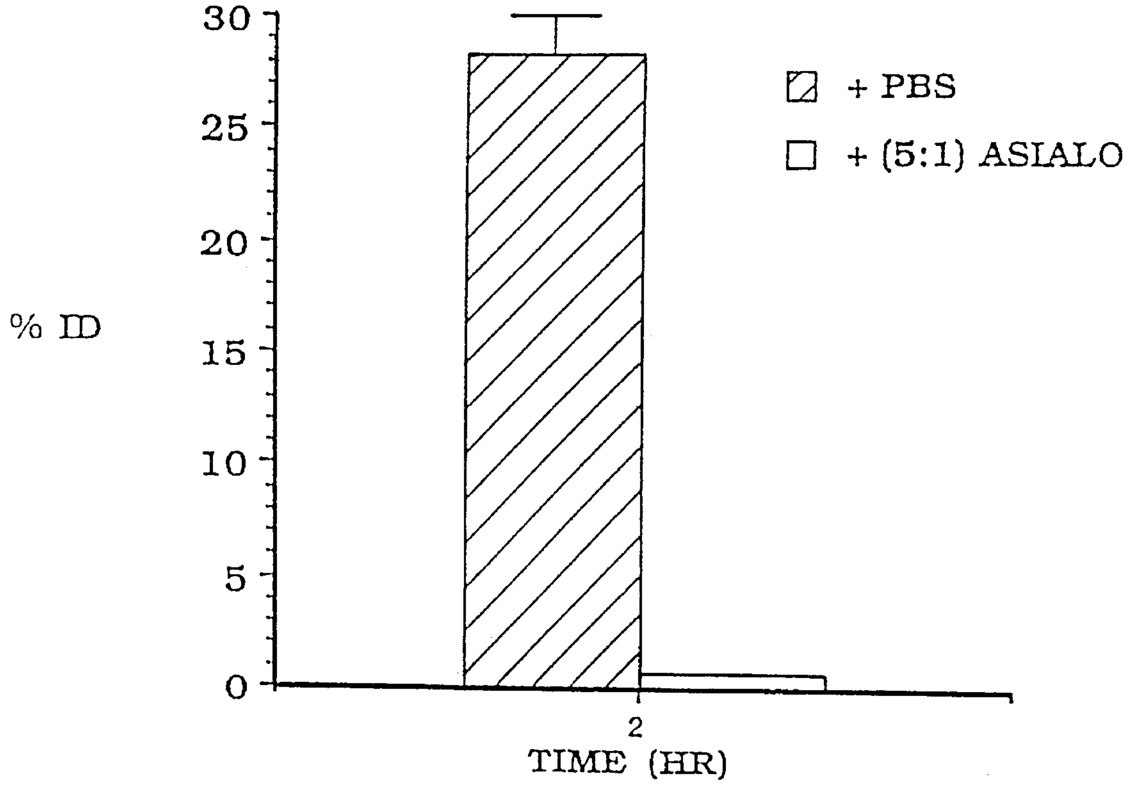
FIG. 9 depicts NR-LU-10-streptavidin conjugate serum biotin binding capability at 2 hours post-clearing agent administration.

Furthermore, residual circulating conjugate was obtained from serum samples by cardiac puncture (with the assays conducted in serum+PBS) and analyzed for the ability to bind biotin (immobilized biotin on agarose beads), an indicator of functional streptavidin remaining in the serum. Group 1 animal serum showed conjugate radiolabel bound about 80% to immobilized biotin. Correcting the residual circulating radiolabel values by multiplying the remaining percent injected dose (at 2 hours after clearing agent administration) by the remaining percent able to bind immobilize biotin (the amount of remaining functional conjugate) leads to the graph shown in FIG. 9. Administration of 200 μg biotinylated asialoorosomucoid resulted in a 50-fold reduction in serum biotin-binding capacity and, in preliminary studies in tumored animals, has not exhibited cross-linking and removal of prelocalized LU-10-StrAv conjugate from the tumor. Removal of circulating targeting moiety-anti-ligand without diminishing biotin-binding capacity at target cell sites, coupled with an increased radiation dose to the tumor resulting from an increase in the amount of targeting moiety-anti-ligand administered, results in both increased absolute rad dose to tumor and diminished toxicity to non-tumor cells, compared to what is currently achievable using conventional radioimmunotherapy.

Figure 10:
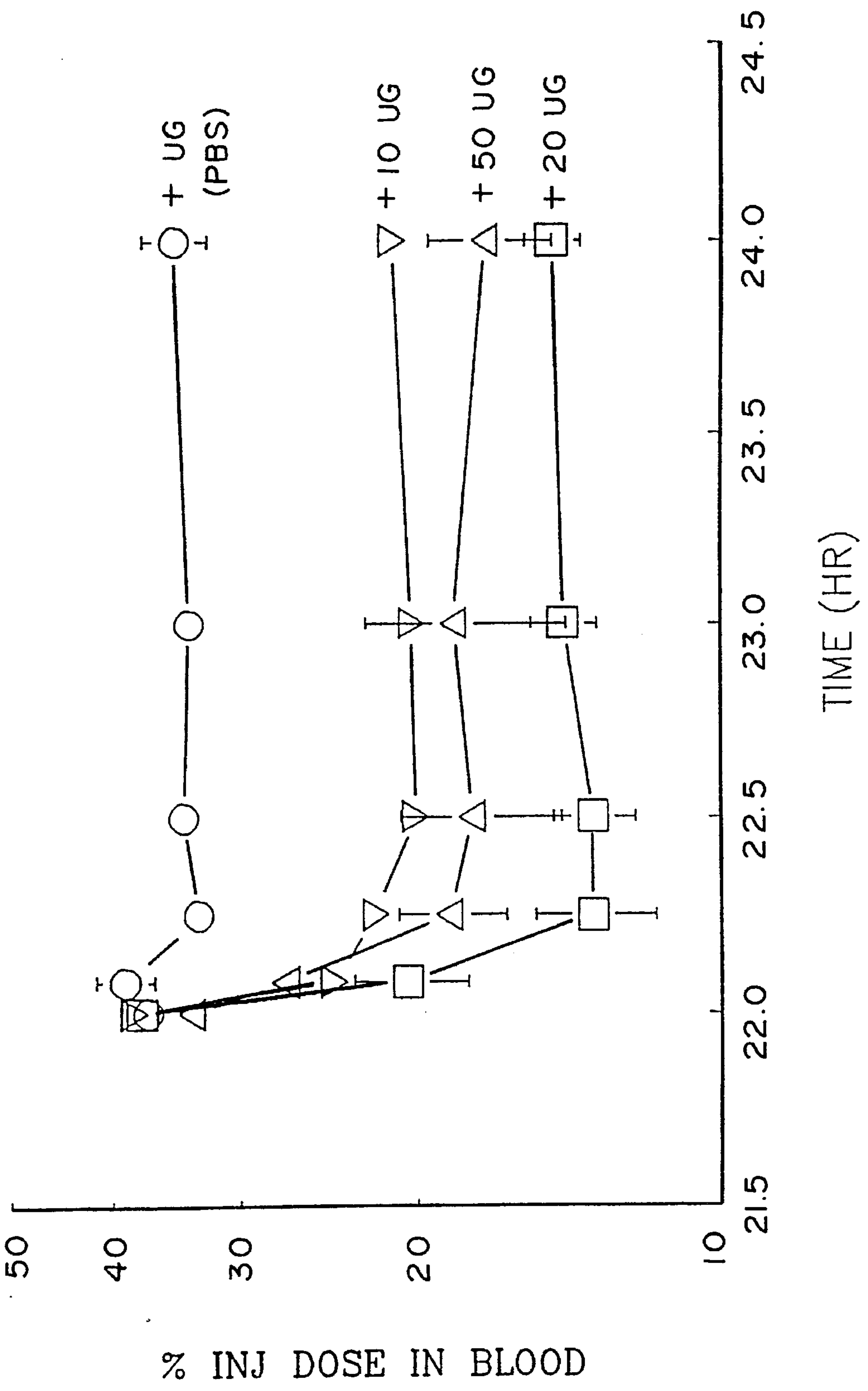
FIG. 10 depicts NR-LU-10-streptavidin conjugate blood clearance over time upon administration of a control (○) and three doses of a clearing agent (∇, Δ, □) at 24 hours post-conjugate administration.
Figure 11A:
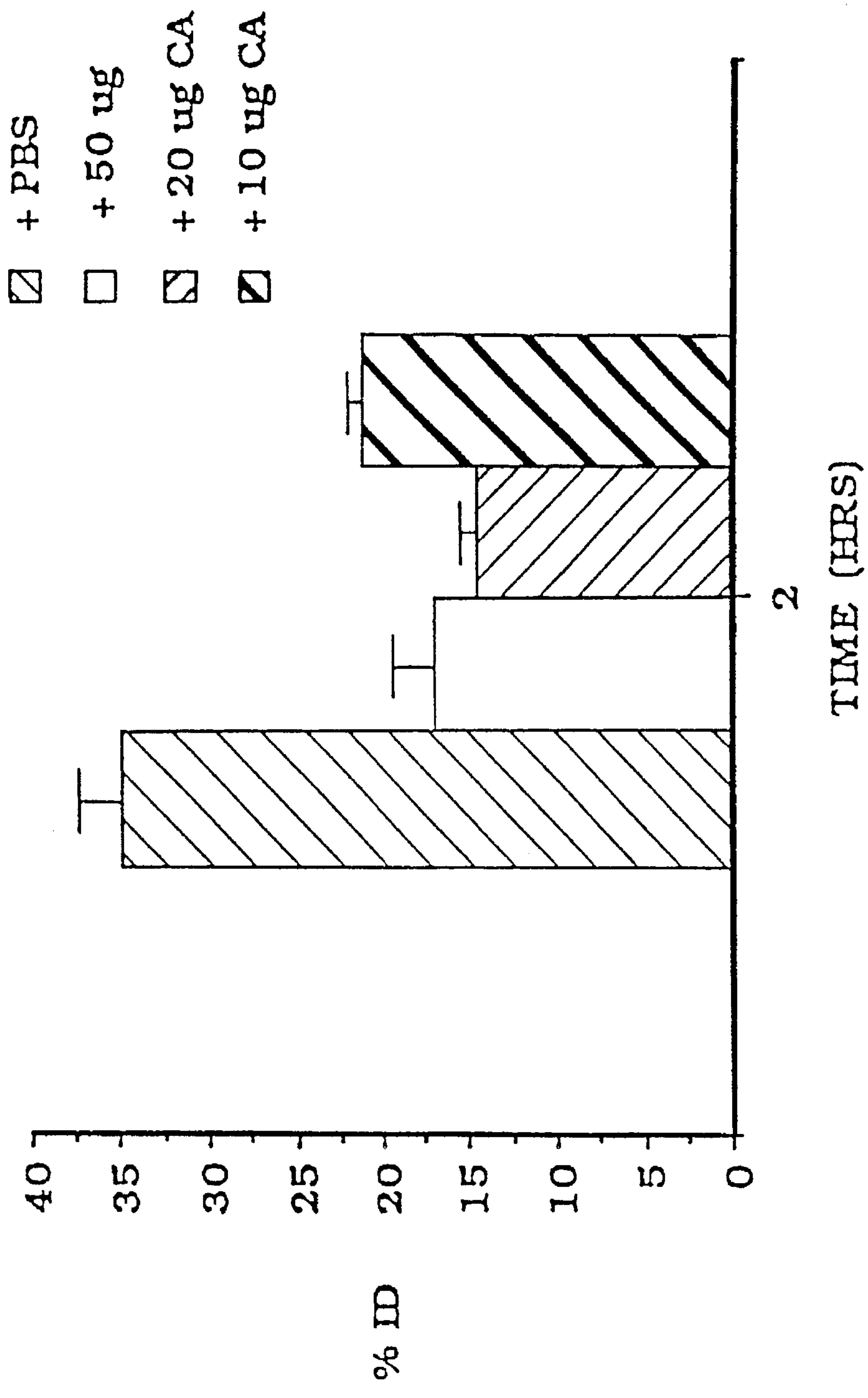
FIG. 11A depicts the blood clearance of LU-10-StrAv conjugate upon administration of a control (PBS) and three doses (50, 20 and 10 μg) of clearing agent at two hours post-clearing agent administration.
Figure 11B:
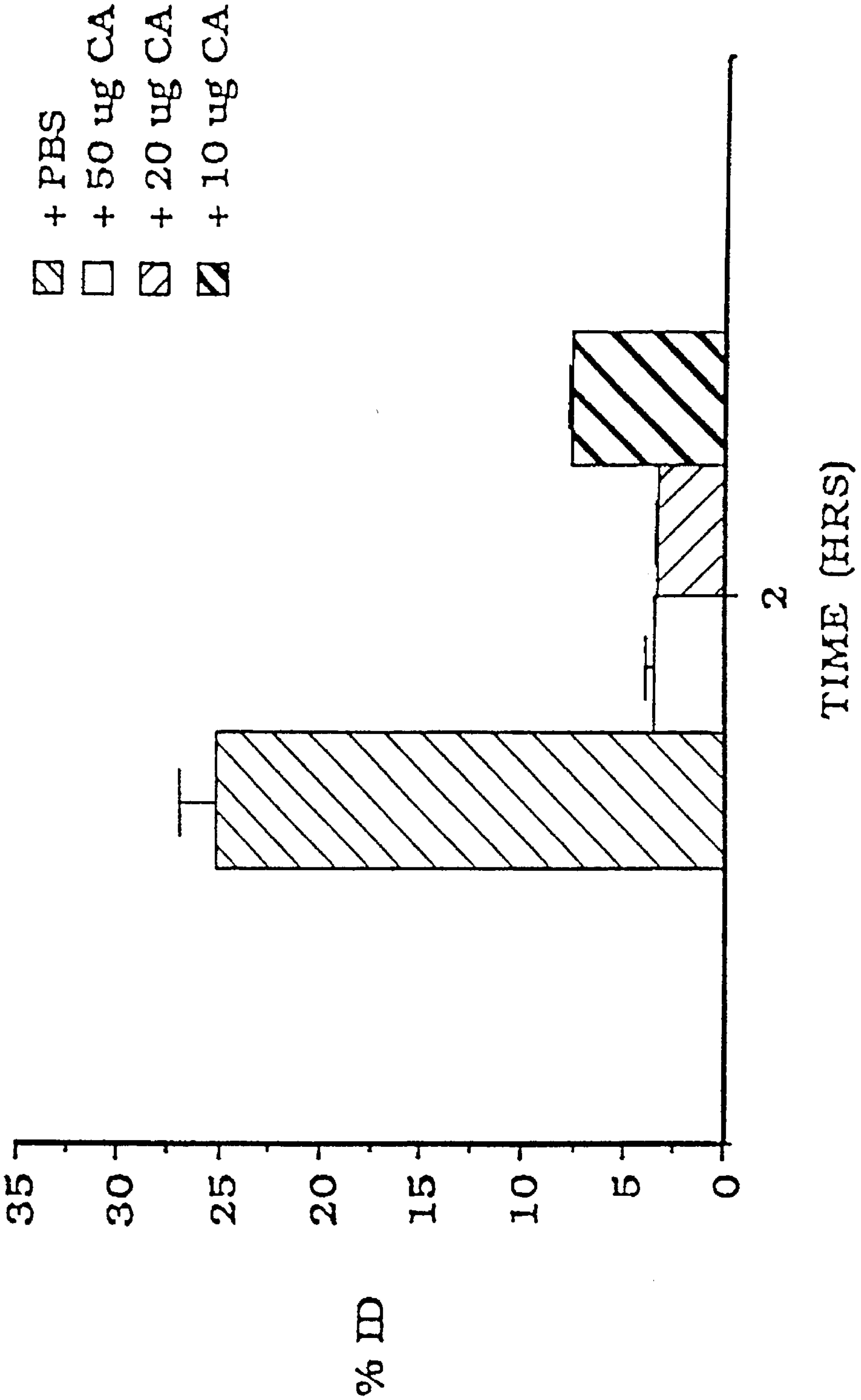
FIG. 11B depicts LU-10-StrAv conjugate serum biotin binding capability upon administration of a control (PBS) and three doses (50, 20 and 10 μg) of clearing agent at two hours post-clearing agent administration.

A subsequent experiment was executed to evaluate lower doses of asialoorosomucoid-biotin. In the same animal model, doses of 50, 20 and 10 μg asialoorosomucoid-biotin were injected at 24 hours following administration of the LU-10-StrAv conjugate. Data from animals serially bled are shown in FIG. 10, and data from animals sacrificed two hours after clearing agent administration are shown in FIGS. 11A (blood clearance) and 11B (serum biotin-binding), respectively. Doses of 50 and 20 μg asialoorosomucoid-biotin effectively reduced circulating LU-10-StrAv conjugate levels by about 65% (FIG. 11A) and, after correction for binding to immobilized biotin, left only 3% of the injected dose in circulation that possessed biotin-binding capacity, compared with about 25% of the injected dose in control animals (FIG. 11B). Even at low doses (approaching 1:1 stoichiometry with circulating LU-10-StrAv conjugate), asialoorosomucoid-biotin was highly effective at reducing blood levels of circulating streptavidin-containing conjugate by an in vivo complexation that was dependent upon biotin-avidin interaction.

EXAMPLE XIV

Streptavidin Anti-Ligand in Tumors

A set of female nude mice, implanted subcutaneously with LS-180 human colon carcinoma xenografts as described above, were randomized into groups of 4 animals/timepoint. The mice were intravenously injected with 200 μg of 1:1 mol/mol NR-LU-10 monoclonal antibody covalently coupled to streptavidin (MAB-STRPT), with the conjugate formed as described in Example XI above. The streptavidin portion of the conjugate was radiolabeled with paraiodophenyl (PIP) I-125, as described in Example IV above. Groups of mice were sacrificed at 26, 30, 48, 96 and 144 hours post-conjugate injection. Tissues were isolated, weighed and counted with respect to iodine radionuclide content using conventional procedures therefor.

A second set of female nude mice bearing LS-180 xenografts were also randomized into groups of 4 animals/timepoint. These mice were intravenously injected with 50 μg of NR-LU-10 monoclonal antibody radiolabeled with paraiodophenyl (PIP) I-131 (MAB), as described in Example IV above. Mice were sacrificed at 4, 24, 48, 128 and 168 hours post-radiolabeled monoclonal antibody injection. Tissues were isolated, weighed and counted with respect to iodine radionuclide content using conventional procedures therefor.

Figure 12:
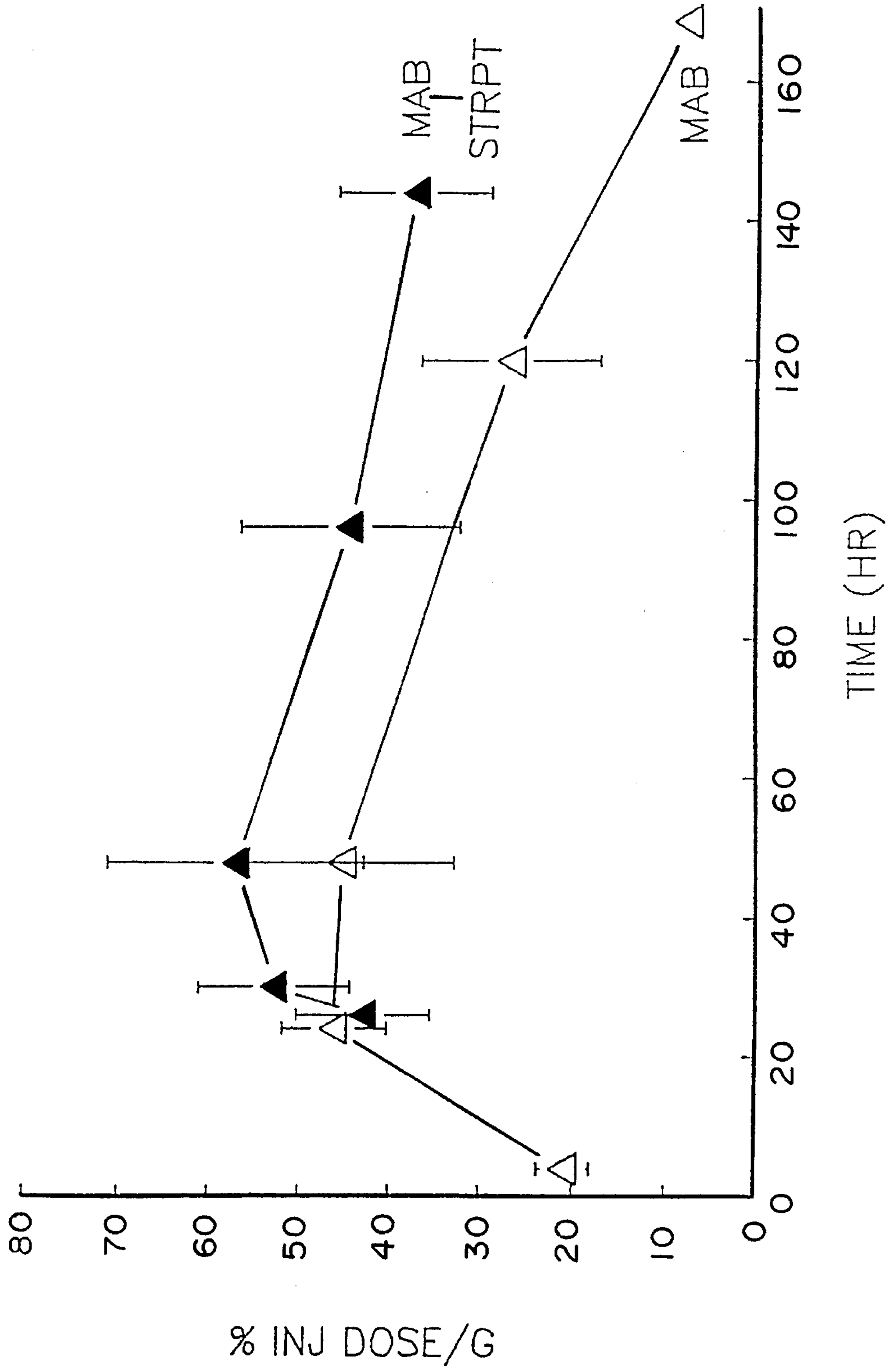
FIG. 12 depicts the prolonged tumor retention of NR-LU-10-streptavidin conjugate (▲) relative to NR-LU-10whole antibody (Δ) over time.

For each data set, a radioactivity standard of the injected dose was also counted, and data were reduced to a percent of the total injected dose per gram of tissue. FIG. 12 shows the percent injected dose/gram of NR-LU-10-streptavidin-PIP-I-125 and NR-LU-10-PIP-I-131 in LS-180 tumors over time. The NR-LU-10-streptavidin conjugate exhibits higher tumor uptake and a longer retention time as compared to NR-LU-10 alone.

EXAMPLE XV

Streptavidin Anti-Ligand in Liver

Female nude mice xenografted with LS-180 tumor cells, as discussed above, were randomized into groups of 4 animals/timepoint. Mice were intravenously injected with 50 μg of biotinylated NR-LU-10 monoclonal antibody that was non-covalently coupled (to form a complex) through biotin-streptavidin binding to 30 μg of streptavidin. Prior to complexation in vivo, the antibody portion of the complex was radiolabeled with I-125 using chloramine-T, and the streptavidin portion was labeled with paraiodophenyl (PIP) I-131, both of the labeling procedures having been described above. Mice were sacrificed at 4, 24, 48, 96 and 144 hours post-conjugate injection. Tissues were isolated, weighed and counted with respect to the content of each iodine radionuclide using conventional procedures therefor.

Figure 13:
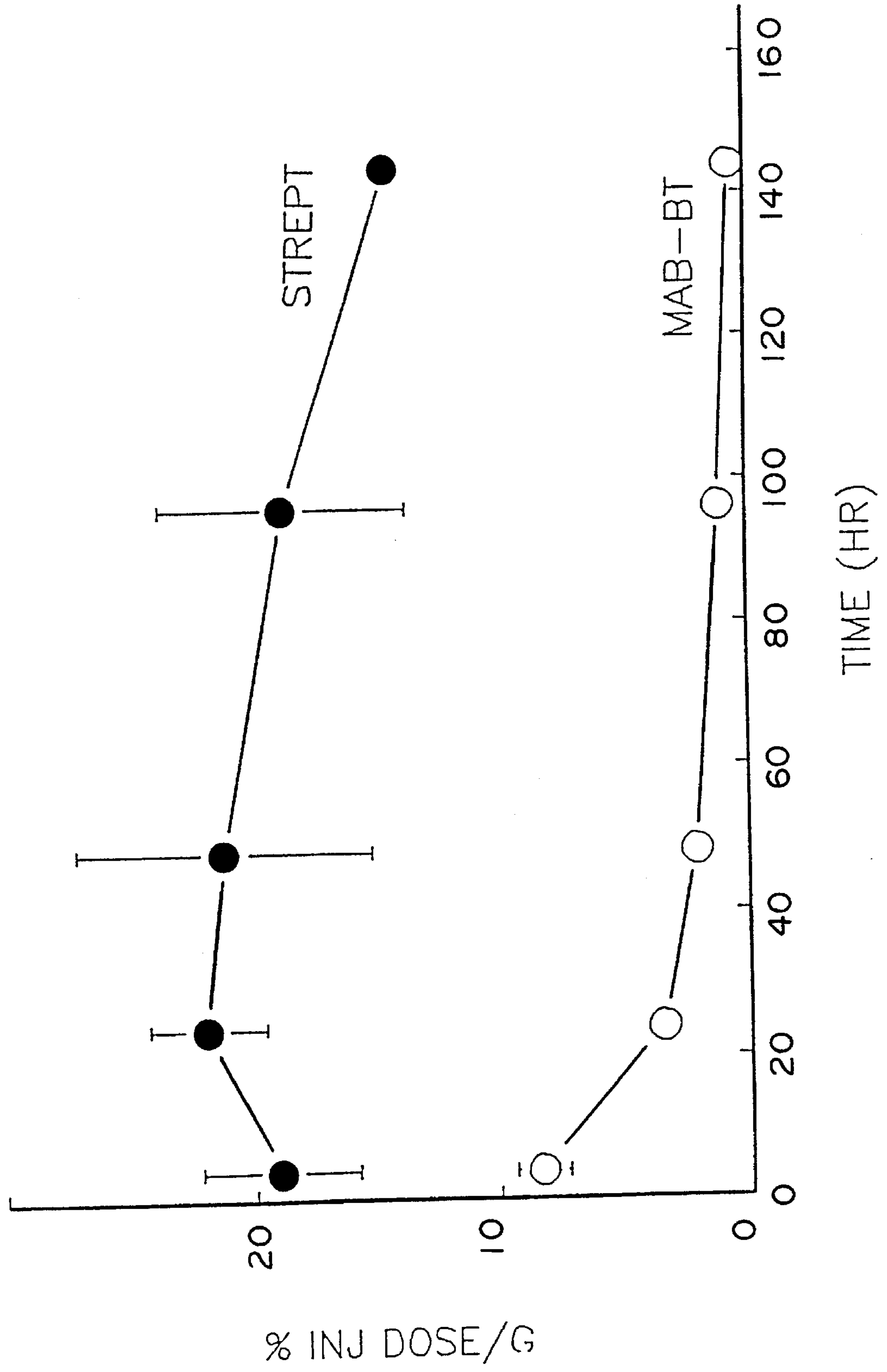
FIG. 13 depicts the prolonged liver retention of a pre-formed complex of NR-LU-10-biotin (○; chloramine T labeled with I-125) complexed with streptavidin (●; PIP-I-131 labeled).

A radioactivity standard of the injected doses of each complex component was also counted, and data were reduced to a percent of the total injected dose per gram of tissue. FIG. 13 shows the percent injected dose per gram of streptavidin-PIP-I-131 (STREPT) and NR-LU-10-biotin-Chloramine-T-I-125 (MAB-BT) in liver over time. The complex localized at the liver as a single molecule; however, the processing of the individual components thereof differed in the liver. The I-131-streptavidin label showed prolonged residence in the liver, while the monoclonal antibody label (I-125) was rapidly lost.

In another liver study, female nude mice xenografted with xenografted with LS-180 tumor cells, as discussed above, and were intravenously injected with 200 μg of 1:1 mol/mol NR-LU-10 monoclonal antibody covalently coupled to streptavidin, prepared as described in Example XI above. The antibody portion of the conjugate was radiolabeled with paraiodophenyl (PIP-I-125). Twenty four hours later, the mice received an injection of 0.5 μg of paraiodophenyl (PIP I-131) biocytin. Mice were sacrificed at 28, 48, 120 and 168 hours post-conjugate injection. Tissues were isolated, weighed and counted with respect to the content of each iodine radionuclide using conventional procedures therefor.

Figure 14:
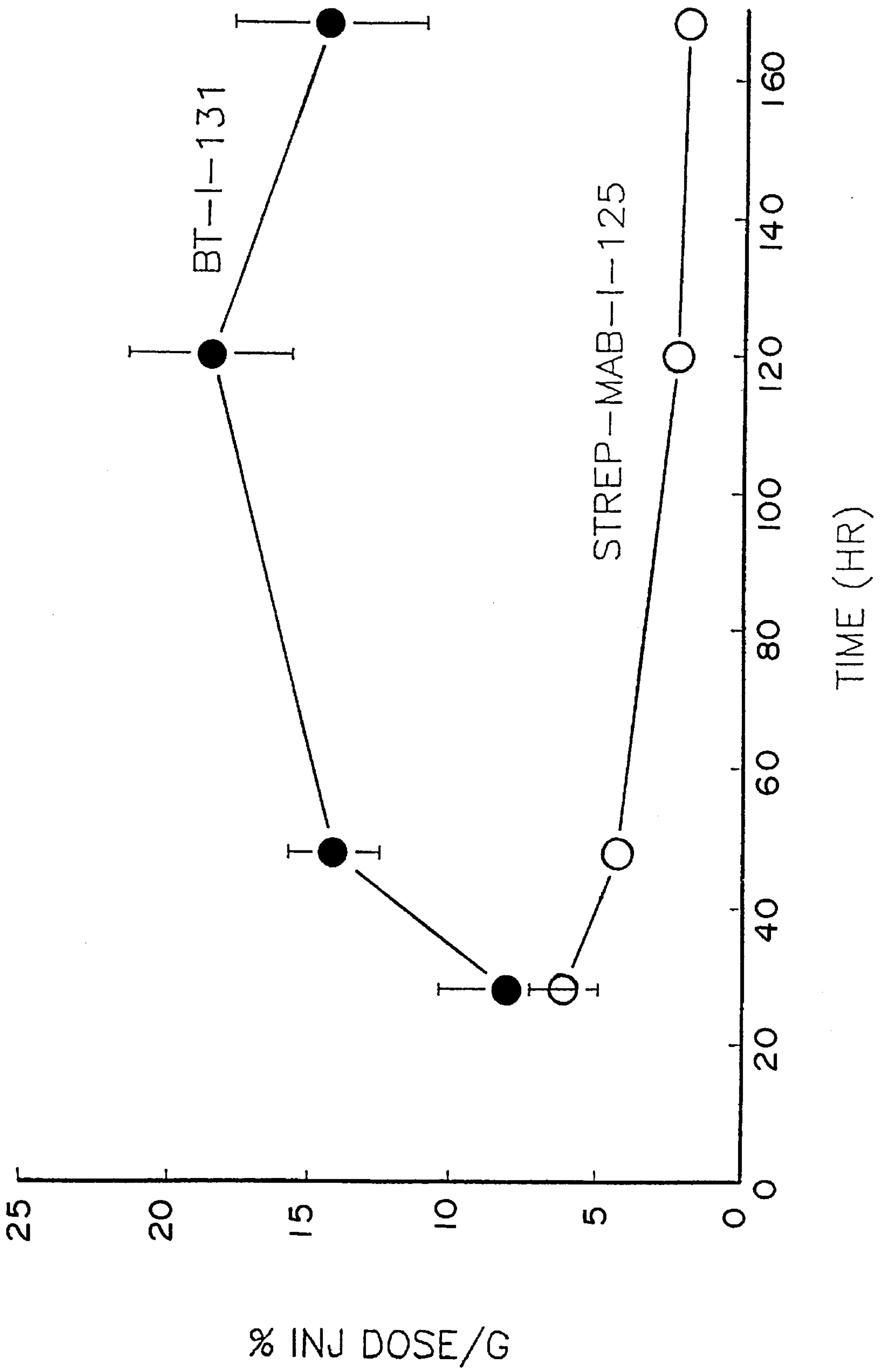
FIG. 14 depicts the prolonged liver retention of Biotin-PIP-I-131 label relative to the streptavidin-NR-LU-10-(PIP-I-125) label.

A radioactivity standard of the injected doses of each complex component was also counted, and data were reduced to a percent of the total injected dose per gram of tissue (%ID/G). FIG. 14 shows the percent injected dose per gram of streptavidin-monoclonal antibody-PIP-I-125 (STREP-MAB-I-125) and biocytin-PIP-I-131 (BT-I-131) in liver over time. When biocytin-PIP-I-131 was subsequently administered, the retention of streptavidin-bound biotin radiolabel (I-131) was prolonged relative to the retention of the antibody-bound label (I-125) on the same moiety in the liver.

EXAMPLE XVI

Tumor Uptake of PIP-Biocytin

Figure 15A:
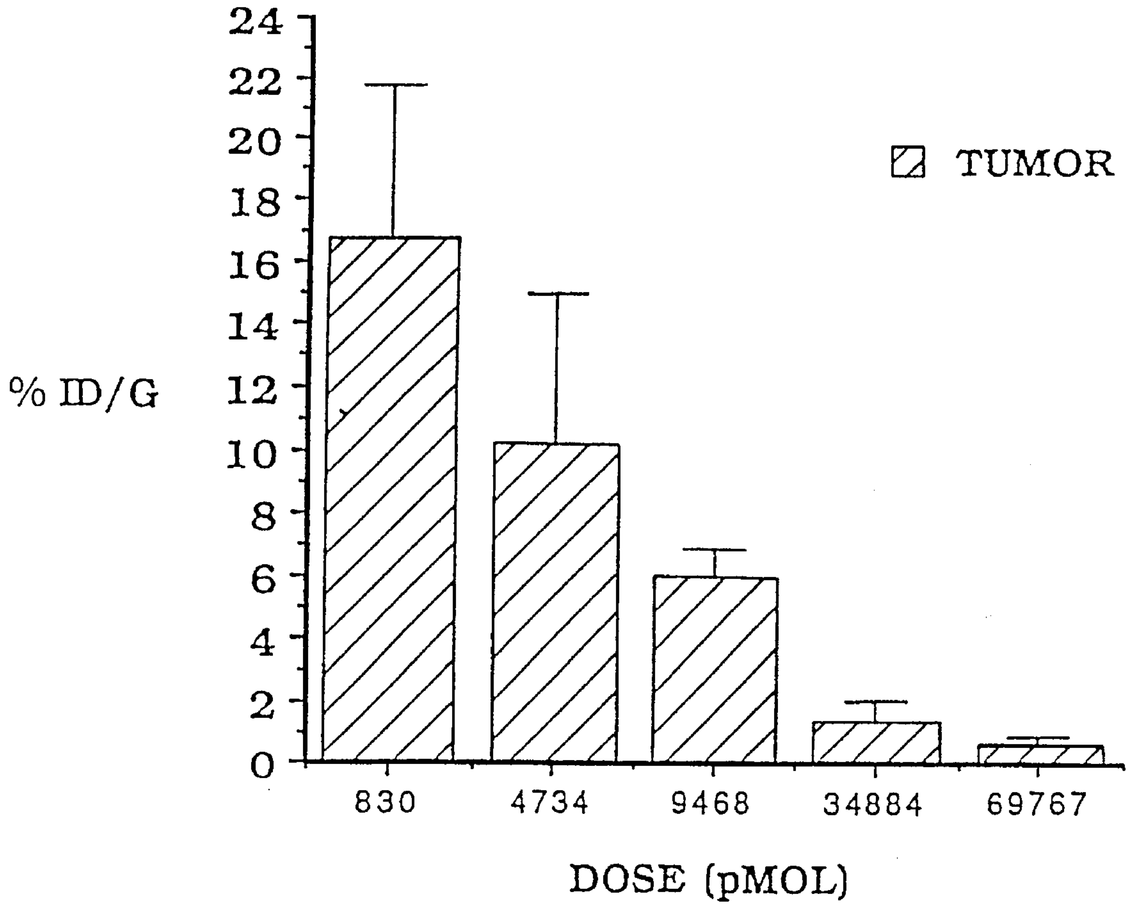
FIG. 15A depicts tumor uptake for increasing doses of PIP-Biocytin in terms of %ID/G.

PIP-Biocytin, as prepared and described in Example VII above, was tested to determine the fate thereof in vivo. The following data are based on experimentation with tumored nude mice (100 mg LS-180 tumor xenografts implanted subcutaneously 7 days prior to study) that received, at time 0, 200 μg of I-125 labeled NR-LU-10-Streptavidin conjugate (950 pmol), as discussed in Example XI above. At 24 hours, the mice received an i.v. injection of PIP-I-131-biocytin (40 μCi) and an amount of cold carrier PIP-I-127 biocytin corresponding to doses of 42 μg (69,767 pmol), 21 μg (34,884 pmol), 5.7 μg (9468 pmol), 2.85 μg (4734 pmol) or 0.5 μg (830 pmol). Tumors were excised and counted for radioactivity 4 hours after PIP-biocytin injection, and the tumor uptake data are shown in FIGS. 15A (%ID/G v. Dose) and 15B (pMOL/G v. Dose).

Figure 15B:
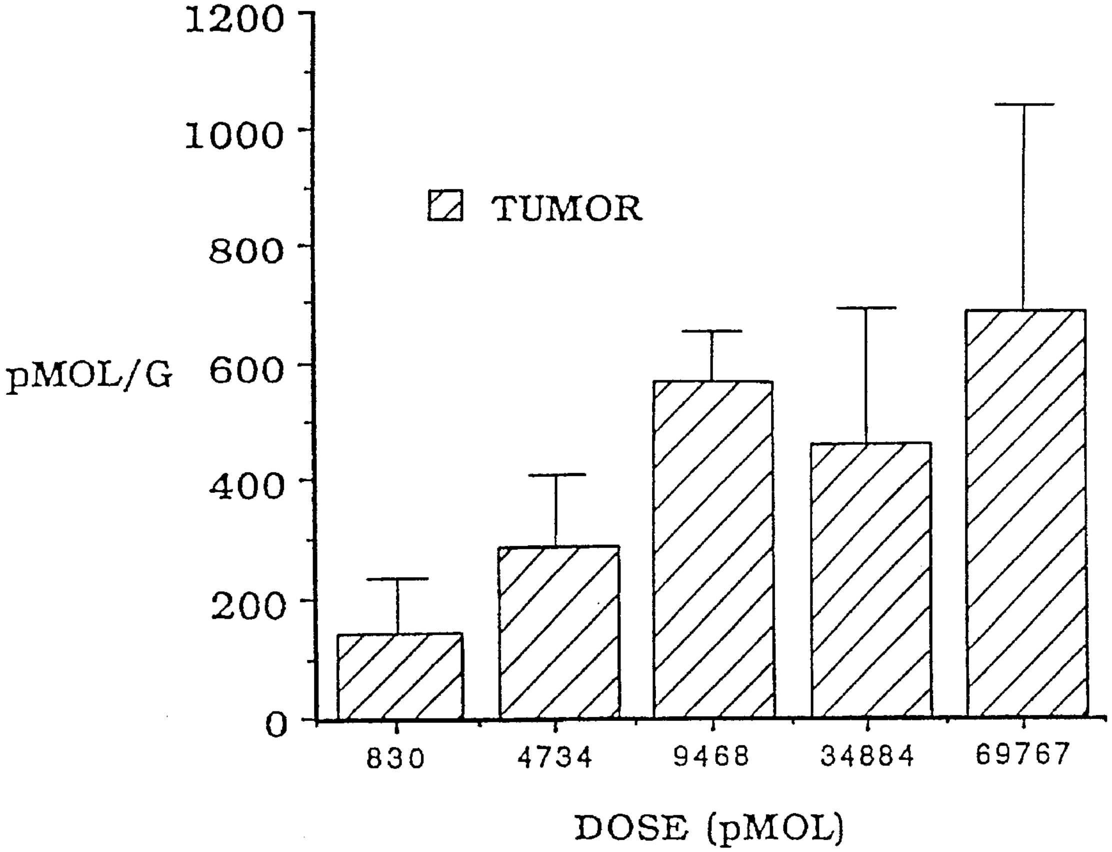
FIG. 15B depicts tumor uptake for increasing doses of PIP-Biocytin over time in terms of pMOL/G.

The three highest doses produced PIP-biocytin tumor localizations of about 600 pmol/g. Histology conducted on tissues receiving the two highest doses indicated that saturation of tumor-bound streptavidin was achieved. Equivalent tumor localization observed at the 5.7 μg dose (FIG. 15B) is indicative of streptavidin saturation as well. In contrast, the two lowest doses produced lower absolute tumor localization of PIP-biocytin, despite equivalent localization of NR-LU-10-Streptavidin conjugate (tumors in all groups averaged about 40% ID/G for the conjugate).

Figure 16A:
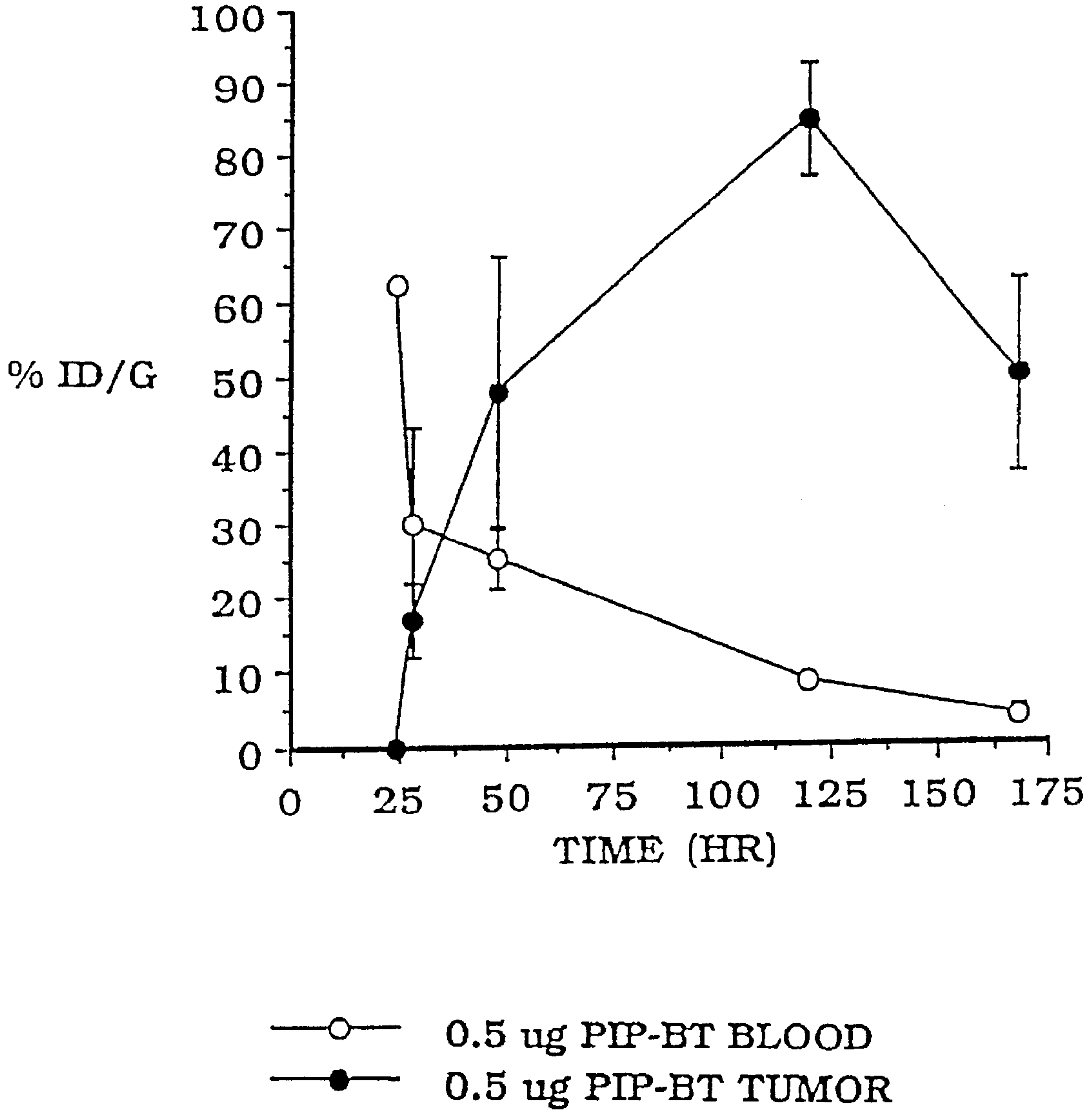
FIG. 16A depicts tumor versus blood localization of a 0.5 μg dose of PIP-Biocytin over time in terms of %ID/G.
Figure 16B:
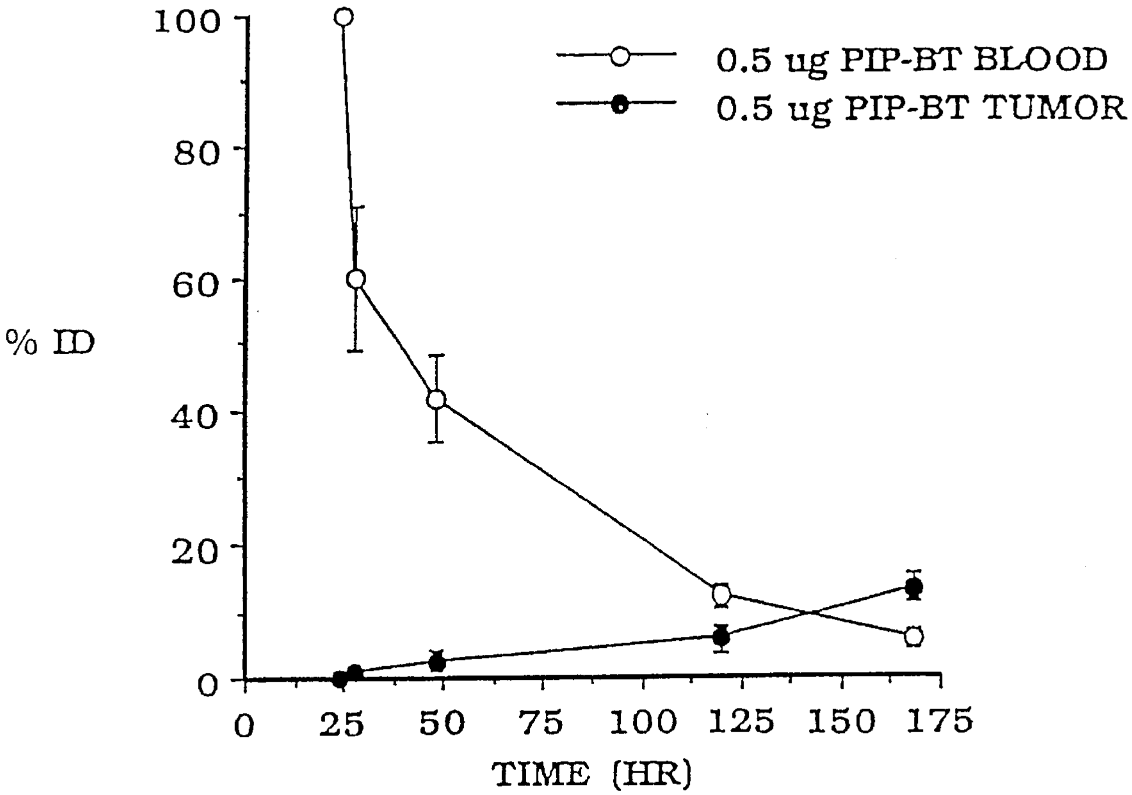
FIG. 16B depicts tumor versus blood localization of a 0.5 μg dose of PIP-Biocytin in terms of %ID.

The lowest dose group (0.5 μg) exhibited high efficiency tumor delivery of PIP-I-131-biocytin, which efficiency increased over time, as shown in FIG. 16A. A peak uptake of 85.0% ID/G was observed at the 120 hour time point (96 hours after administration of PIP-biocytin). Also, the absolute amount of PIP-biocytin, in terms of % ID, showed a continual increase in the tumor over all of the sampled time points (FIG. 16B). The decrease in uptake on a % ID/G basis (FIG. 16A) at the 168 hour time point resulted from significant growth of the tumors between the 120 and 168 hour time points.

Figure 17A:
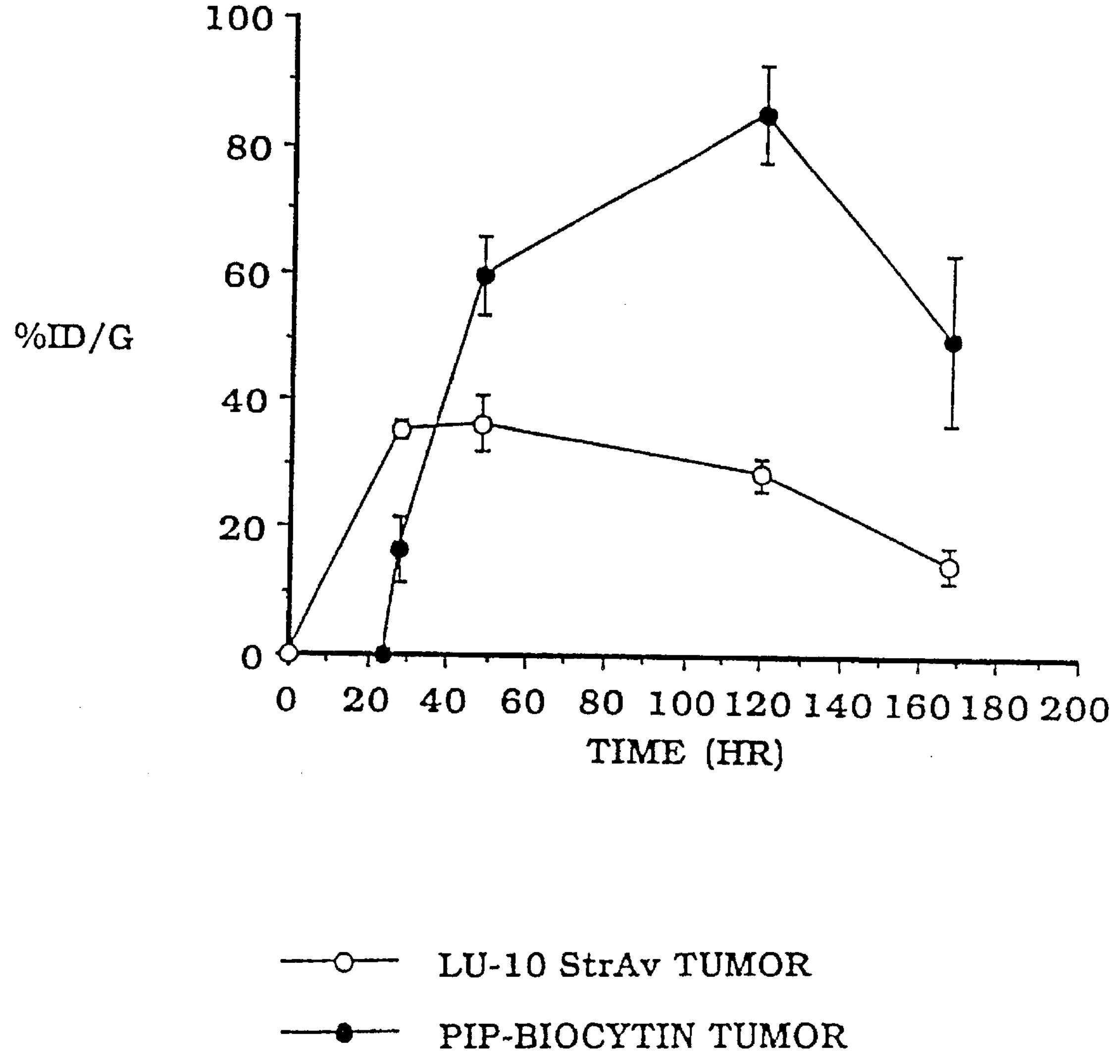
FIG. 17A depicts tumor uptake of LU-10-StrAv and PIP-Biocytin over time in terms of %ID/G.

In addition, FIG. 17A shows the co-localization of NR-LU-10-Streptavidin conjugate (LU-10-StrAv) and the subsequently administered PIP-Biocytin at the same tumors over time. The localization of radioactivity at tumors by PIP-biocytin exhibited a pattern of uptake and retention that differed from that of the antibody-streptavidin conjugate (LU-10-StrAv). LU-10-StrAv exhibited a characteristic tumor uptake pattern that is equivalent to historical studies of native NR-LU-10 antibody, reaching a peak value of 40%

Figure 17B:
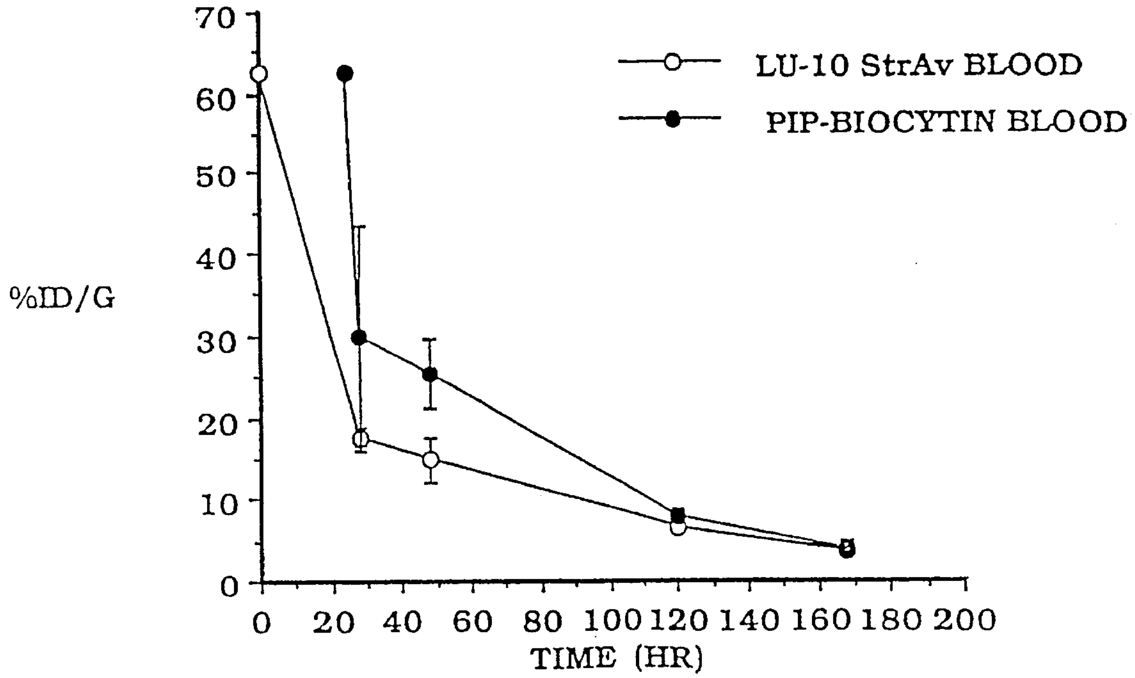
FIG. 17B depicts blood clearance of LU-10-StrAv and PIP-Biocytin over time in terms of %ID/G.

ID/G between 24 and 48 hours after administration. In contrast, the PIP-Biocytin exhibited an initial rapid accretion in the tumor, reaching levels greater than those of LU-10-StrAv by 24 hours after PIP-Biocytin administration. Moreover, the localization of PIP-Biocytin continued to increase out to 96 hours, when the concentration of radioactivity associated with the conjugate has begun to decrease. The slightly greater amounts of circulating PIP-Biocytin compared to LU-10-StrAv at these time points (shown in FIG. 17B) appeared insufficient to account for this phenomenon.

Figure 18:
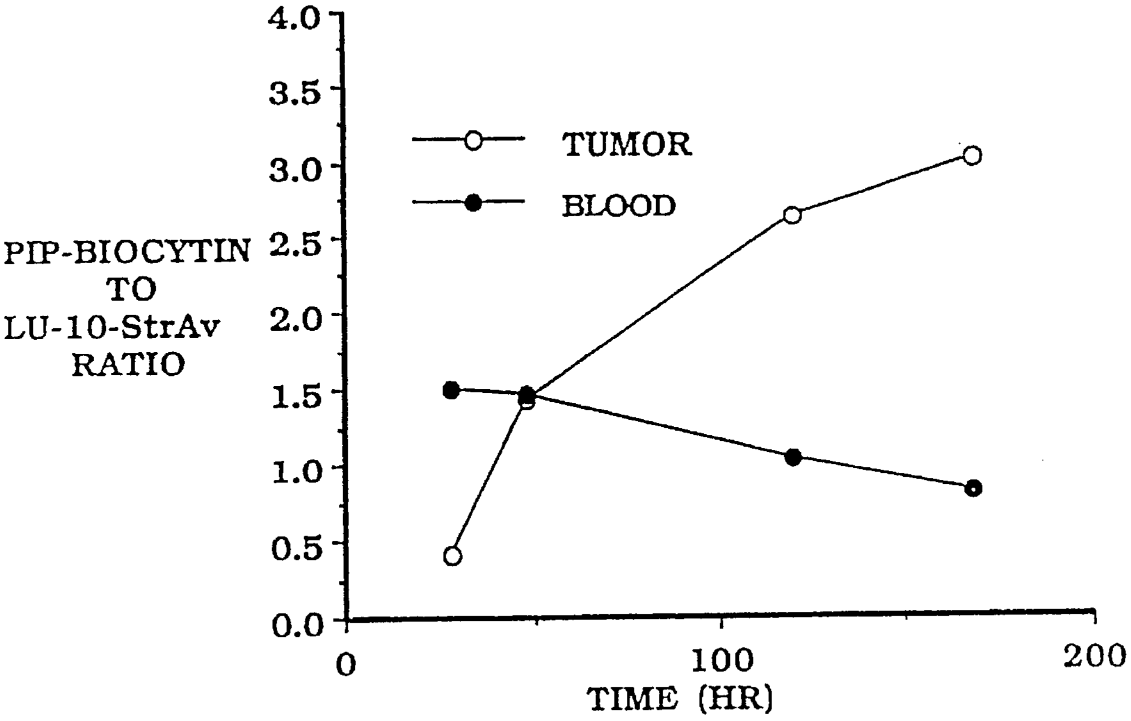
FIG. 18 depicts PIP-Biocytin:LU-10-StrAv ratio in tumor and blood over time.

As FIG. 18 clearly shows, the ratio of PIP-Biocytin to LU-10-StrAv in the tumor increased continually during the experiment, while the ratio in the blood decreased continually. This observation is consistent with a process involving continual binding of targeting moiety-containing conjugate (with PIP-Biocytin bound to it) from the blood to the tumor, with subsequent differential processing of the PIP-Biocytin and the conjugate. Since radiolabel associated with the streptavidin conjugate component (compared to radiolabel associated with the targeting moiety) has shown increased retention in organs of metabolic processing (Examples XIV and XV above), PIP-Biocytin associated with the streptavidin appears to be selectively retained by the tumor cells. Because radiolabel is retained at target cell sites, a greater accumulation of radioactivity at those sites results.

The $AUC_{tumor}/AUC_{blood}$ for PIP-Biocytin is over twice that of the conjugate (4.27 compared to 1.95, where AUC means "area under the curve"). Further, the absolute $AUC_{tumor}$ for PIP-Biocytin is nearly twice that of the conjugate (9220 compared to 4629). Consequently, an increase in radiation dose to tumor was achieved.

EXAMPLE XVII

Polymer-Ligand Conjugation

Polylysine (approximately 10,000 Dal. molecular weight, available from Sigma Chemical Co., St. Louis, Mo.) and dextran (lysine fixable, available from Sigma Chemical Co.) were derivitized with SPDP and purified from unreacted SPDP using size exclusion chromatography (using a PD-10 column available from Pharmacia, Piscataway, N.J.). The resultant SPDP-derivitized adducts were reduced with DTT in pH 4.7 0.2M NaOAc buffer to generate free reactive thiols. Reduced Tc-99m, generated from stannous gluconate as described, for example, by Carlsson et al., *Biochem. J.*, 173: 723–737, 1978, was added. A 90% incorporation of Tc-99m was obtained for the polylysine adduct within 15 min, as measured by ITLC. 96% of the radioactivity coeluted with the dextran using size exclusion (PD-10) chromatography. These results are indicative of chelation.

EXAMPLE XVIII

Preparation of Trichothecene-Linker Molecules

A. Preparation of 3-(2-Pyridinyldithio)propanoic acid. 5.00 g (52.2 mmol) of 3-mercaptopropanoic acid (Aldrich Chemical Co., Milwaukee, Wis.) in 75 ml of dry methylene chloride was added to a solution of 5.96 g (52.2 mmol) of methoxycarbonylsulfenyl chloride (Fluka Chemika, Long Island, N.Y.) in 150 ml of dry methylene chloride. The mixture was stirred at 15°–25° C. for 90 minutes and then concentrated. The residue was redissolved in 150 ml of dry methylene chloride and dropwise treated with 5.80 g (52.2 mmol) of 2-mercaptopyridine (Aldrich Chemical Co.) in 75 ml of dry methylene chloride. The mixture was stirred at 15°–25° C. for 18 hours and concentrated to afford 11.2 g of the product as a pale yellow oil (99%).

B. Preparation of 3- (2-pyridinyldithio)propanoic acid hydrazide. Dry triethylamine (3.76 g, 37.2 mmol) was added to a solution of 8.00 g (37.2 mmol) of 3-(2-pyridinyldithio-)propanoic acid in 100 ml of dry tetrahydrofuran (THF). The mixture was cooled in an ice bath followed by the addition of 5.08 g (37.2 mmol) of isobutyl chloroformate. The mixture was stirred for 5–10 minutes, and 4.92 g (37.2 mmol) of tert-butyl carbazate was added. The resultant mixture was stirred at 15°–25° C. for 1 hour and then Concentrated. The residue was diluted with 200 ml of methylene chloride and washed with water (2×100 ml). The organic phase was dried over magnesium sulfate, filtered and concentrated. The residue was dissolved in ice-cold trifluoroacetic acid (160 ml) and stirred for 10 minutes after dissolution was complete. The mixture was concentrated, and the residue was chromatographed on silica gel, eluting with 85:14:1 chloroform?methanol/ammonium hydroxide, to afford 4.25 g of the product as a pale yellow solid (50%): TLC-$R_f$ 0.55 (85:15:1 chloroform/methanol/ammonium hydroxide).

C. Preparation of Hydrazone Derivative of 3-Dehydroanguidine and 3-(2-Pyridinylithio)propanoic Acid Hydrazide. 100 microliters (0.708 mmol) of trifluoroacetic anhydride at –70° C. was added to a solution of 100 microliters of dry dimethylsulfoxide (1.41 mmol) in 3 ml of dry methylene chloride. The mixture was stirred at –70° C. for 10 minutes and then 70 mg (0.198 mmol) of anguidine (Sigma Chemical Co.) in 2 ml of dry methylene chloride was added over a period of 2–3 minutes. The resultant mixture was stirred at –70° C. for 15 minutes and then 20 microliters of dry triethylamine was added. The mixture was stirred at –70° C. for 15 minutes and at –70° C. to 15° C. for 60 minutes. The resultant mixture was diluted with 50 ml of methylene chloride and washed with 1N aqueous HCl (50 ml). The organic phase was dried over magnesium sulfate, filtered and concentrated to afford crude 3-dehydroanguidine. The crude material was dissolved in 3 ml of dry methanol and treated with 100 mg (0.436 mmol) of 3-(2-pyridinyldithio-)propanoic acid hydrazide followed by 0.021 mmol of trifluoroacetic acid in 100 microliters of methanol. The mixture was stirred at 15°–25° C. for 5 hours and then concentrated. The residue was chromatographed on silica gel, eluting with 75% ethyl acetate/hexane, to afford 67 mg of the product, a foamy white solid, as a mixture of syn and anti isomers (60%): TLC-$R_f$ 0.43 and 0.60 (75% ethyl acetate/hexane).

D. Preparation of a Hydrazone Derivative of 2'-dehydro-Roridin A.

1. Preparation of 13'-O-tert-butyldimethylsilyl-Roridin A. 100 mg (1.47 mmol) of imidazole was added to a solution of 232 mg (0.436 mmol) of Roridin A in 3 ml of dry dimethylformamide. The mixture was cooled to –5° C. and then 72 mg (0.478 mmol) of tert-butyldimethylsilyl chloride (Aldrich Chemical Co.) was added. The resultant mixture was stirred at –5° C. to 5° C. for 4 hours and then concentrated. The residue was chromatographed on silica gel, eluting first with 30% ethyl acetate/hexane, next with 50% ethyl acetate/hexane and finally with 70% ethyl. acetate/hexane, to afford 137 mg of the product as a foamy white solid (49%): TLC-$R_f$ 0.32 (30% ethyl acetate/hexane).

2. Preparation of 2'-dehydro-13'-O-tert-butyldimethylsilyl-Roridin A. At –70° C., 150 microliters (1.06 mmol) of trifluoroacetic anhydride was added to a solution of 100 microliters (1.41 mmol) of dry dimethylsulfoxide in 3 ml of dry methylene chloride. The mixture was stirred at −70° C. for 15 minutes and then 100 mg (0.155 mmol) of 13'-O-tert-butyldimethylsilyl-Roridin A in 2 ml of dry methylene chloride was added. The resultant mixture was stirred at −70° C. for 15 minutes and then 300 microliters (2.15 mmol) of dry triethylamine was added. This mixture was stirred at −70° C. for 30 minutes and at −70° C. to 15° C. for 30 minutes. The resultant mixture was then concentrated and the residue was chromatographed on silica gel, eluting with 30% ethyl acetate/hexane, to afford 82 mg of the product as a foamy white solid (82%): TLC-$R_f$ 0.51 (30% ethyl acetate/hexane).

3. Preparation of 2'-dehydro-Roridin A. 5 ml of 3:1:1 acetic acid:THF:water was added to a 10 ml round bottom flask, charged with 62 mg (0.096 mmol) of 2'-dehydro-13"-O-tert-butyldimethylsilyl-Roridin A. The mixture was stirred at 45°–50° C. for 4.5 hours, cooled and concentrated. The residue was chromatographed on silica gel, eluting with 5% methanol/methylene chloride, to afford 36 mg of the product as a foamy white solid (70%): TLC-$R_f$ 0.48 (5% methanol/methylene chloride).

4. Preparation of a hydrazone derivative of 2'-dehydro-Roridin A and 3-(2-pyridinyldithio)propanoic acid hydrazide. To a solution of 25 mg (0.471 mmol) of 2'-dehydro-Roridin A in 2 ml of dry methanol was added 30 mg (0.131 mmol) of 3-(2-pyridinyldithio)propanoic acid hydrazide followed by 0.013 mmol trifluoroacetic acid. The mixture was stirred at 15°–25° C. for 4 hours and then concentrated. The residue was chromatographed on silica gel, eluting with 75% ethyl acetate/hexane, to afford 25 mg of the product as a mixture of syn and anti isomers (71%): TLC-$R_f$ 0.29 and 0.53 (75% ethyl acetate/hexane).

E. Preparation of a Hydrazone Derivative of 2'-O-Acetyl-13'-Dehydro-Roridin A.

1. Preparation of 2'-O-acetyl-13'-O-tert-butyl dimethylsilyl-Roridin A. To a solution of 159 mg (0.246 mmol) of 13'-O-tert-butyldimethylsilyl Roridin A in 4 ml of dry methylene chloride was added 200 microliters (1.43 mmol) of triethylamine, 2 mg (0.019 mmol) of dimethylaminopyridine and 120 microliters (1.27 mmol) acetic anhydride. The mixture was stirred at 15°–25° C. for 16 hours and then concentrated. The residue was chromatographed on silica gel, eluting first with 30% ethyl acetate/hexane and then with 50% ethyl acetate/hexane, to afford 156 mg of the product as a foamy white solid (92%): TLC-$R_f$ 0.50 (30% ethyl acetate/hexane).

2. Preparation of 2'-O-acetyl-Roridin A. To a solution of 156 mg (0.226 mmol) of 2'-O-acetyl-13'-tert-butyldimethylsilyl-Roridin A in 3 ml of dry THF was added 1.5 ml of 1M tetrabutyl ammonium fluoride. The mixture was stirred at 15°–25° C. for 4 hours and then concentrated. The residue was chromatographed on silica gel, eluting with 50% ethyl acetate/hexane, to afford 125 mg of the product as a foamy white solid (96%): TLC-$R_f$ 0.17 (50% ethyl acetate/hexane).

3. Preparation of 2'-O-acetyl-13'-dehydro-Roridin A. To a solution of 62 microliters (0.87 mmol) of dry dimethylsulfoxide in 2 ml of dry methylene chloride at −70° C. was added 62 microliters (0.439 mmol) trifluoroacetic anhydride. The mixture was stirred at −70° C. for 10 minutes followed by the addition of 25 mg (0.044 mmol) of 2'-O-acetyl-Roridin A in 1.5 ml of dry methylene chloride over a 2–3 minute period. This mixture was stirred at −70° C. for 20 minutes and then 180 microliters (1.29 mmol) of dry triethylamine was added. The resultant mixture was stirred at −70° C. for 15 minutes and at −70° C. to 15° C. for 20 minutes and then concentrated. The residue was chromatographed on silica gel, eluting with 5% methanol/methylene chloride, to afford 21 mg of the product as a foamy white solid.

4. Preparation of a hydrazone derivative of 2'O-acetyl-13'-dehydro-Roridin A and 3-(2-pyridinyldithio) propanoic acid hydrazide. To a solution of 21 mg (0.037 mmol) of 2'-O-acetyl-13'-dehydro-Roridin A in 3 ml of dry methanol was added 25 mg (0.11 mmol) of 3-(2-pyridinyldithio)propanoic acid hydrazide followed by 0.011 mmol of trifluoroacetic acid in 100 microliters of dry methanol. The mixture was stirred at 15°–25° C. for 3 hours and then concentrated. The residue was chromatographed on silica gel, eluting first with 75% ethyl acetate/hexane and then with ethyl acetate, to afford 18 mg of the product as a colorless oil (62%): TLC-$R_f$ 0.30 (75% ethyl acetate/hexane).

F. Preparation of 2'-Desoxy-2'-alpha-(N-hydroxysuccinimidyl-3-dithiopropanoic acid)-Roridin A.

1. Preparation of 2'-desoxy-2'-beta-iodo-13'-O-tert-butyldimethylsilyl-Roridin A. To a solution of 99 mg (0.153 mmol) of 13'-O-tert-butyldimethylsilyl-Roridin A in 5 ml of dry methylene chloride, at 0° C., was added 80 microliters (0.459 mmol) of dry diisopropylethylamine followed by 51 microliters (0.303 mmol) of trifluoromethanesulfonic anhydride. The mixture was stirred at 0° C. for 30 minutes and then diluted with 30 ml of methylene chloride and washed with 20 ml of 1N aqueous HCl. The organic phase was dried over magnesium sulfate, filtered and concentrated. The residue was diluted with 5 ml of acetone and then 235 mg (1.72 mmol) of sodium iodide. The mixture was stirred at reflux for 20 minutes and then diluted with 50 ml of methylene chloride and washed with 25 ml of water. The organic phase was dried over magnesium sulfate, filtered and concentrated. The residue was chromatographed on silica gel, eluting with 30% ethyl acetate/hexane to afford 95 mg of the product as a foamy white solid (87%): TLC-$R_f$ 0.55 (35% ethyl acetate/hexane).

2. Preparation of 2'-desoxy-2'-beta-iodo-Roridin A. To 95 mg (0.126 mmol) of 2'-desoxy-2'-beta-iodo-13'-O-tert-butyldimethylsilyl-Roridin A was added 5 ml of 3:1:1 acetic acid:THF:water. The mixture was stirred at 60°–65° C. for 4 hours and then concentrated. The residue was chromatographed on silica gel, eluting with 60% ethyl acetate/hexane, to afford 67 mg of the product as a foamy white solid (83%).

3. Preparation of 2'-desoxy-2'-alpha-thioacetyl-Roridin A. To a solution of 67 mg (0.104 mmol) of 2'-desoxy-2'-beta-iodo-Roridin A in 5 ml of absolute ethanol was added 240 mg (2.10 mmol) of potassium thioacetate. The mixture was stirred at 65°–70° C. for 5 hours, cooled, diluted with 50 ml of methylene chloride and washed with 50 ml of water. The organic phase was dried over magnesium sulfate, filtered and concentrated. The residue was chromatographed on silica gel, eluting with 60% ethyl acetate/hexane, to afford 58 mg of the product as a foamy white solid (94%): TLC-$R_f$ 0.53 (60%ethyl acetate/hexane).

4. Preparation of 2'-desoxy-2'-alpha-mercaptyl-Roridin A. To a solution of 57 mg (0.097 mmol) of 2'-desoxy-2'-alpha-thioacetyl-Roridin A in 4 ml of ethanol was added 2 ml of 28% aqueous ammonium hydroxide. The mixture was stirred at 65°–70° C. for 6 hours. The mixture was concentrated and the residue was chromatographed on silica gel, eluting with 10% ethyl acetate/hexane, to afford 25 mg of an intermediate disulfide. The disulfide was diluted into 3 ml of methylene chloride and 0.5 ml of methanol and 25 microliters (0.10 mmol) of tributylphosphine was added. The mixture was stirred at 15°–25° C. for 15 minutes and then concentrated. The residue was chromatographed on silica gel, eluting with 60% ethyl acetate/hexane, to afford 23 mg of the product as a colorless oil (43%): TLC-$R_f$ 0.39 (60% ethyl acetate/hexane).

5. Preparation of 2'-desoxy-2'-alpha-(3-dithiopropanoic acid)-Roridin A. To a solution of 21 mg (0.038 mmol) of 2'-desoxy-2'-alpha-mercaptyl-Roridin A in 3 ml of ethanol was added 20 mg (0.093 mmol) of 3-(2-pyridinyldithio)propanoic acid followed by 25 microliters (0.179 mmol) of triethylamine. The mixture was stirred at 15°–25° C. for 30 minutes and then diluted with 50 ml of ethyl acetate and washed with 10 ml of 1N aqueous HCl. The organic phase was dried over magnesium sulfate, filtered and concentrated. The residue was chromatographed on silica gel, eluting first with 0.1% acetic acid/ethyl acetate and then with 0.1:5:95 acetic acid:methanol:ethyl acetate, to afford 22 mg of the product as a near colorless oil (88%): TLC-$R_f$ 0.37 (0.1:5:95 acetic acid:methanol:ethyl acetate).

6. Preparation of 2'-desoxy-2'-alpha-(N-hydroxy succinimidyl-3-dithiopropanoic acid)-Roridin A. To a solution of 22 mg (0.0337 mmol) of 2'-desoxy-2'-alpha-(3-dithiopropanoic acid)-Roridin A in 2 ml of dry THF was added 12 mg (0.104 mmol) of N-hydroxysuccinimide followed by 18 mg (0.087 mmol) of dicyclohexyl carbodiimide. The mixture was stirred at 15°–25° C. for 4 hours and then 20 microliters of acetic acid was added. The mixture was stirred an additional 30 minutes and then filtered through a plug of glass wool. The solids were washed with 3 ml of THF. The filtrates were combined and concentrated. The residue was chromatographed on silica gel, eluting first with 0.1:50:50 acetic acid:ethyl acetate:hexane and then with 0.1% acetic acid/ethyl acetate, to afford 18 mg of the product as a white solid (71%): TLC-$R_f$ 0.69 (ethyl acetate).

EXAMPLE XIX

Preparation of Trichothecene-Containing Conjugates

Conjugation of trichothecenes as described in the specification may be conducted through either of two exemplary synthesis schemes: (1) reaction of the amino groups of a targeting moiety with N-hydroxyl succinimidate (NHS)-derivatized trichothecenes or (2) the reaction of reduced disulfides or free sulfhydryls of a targeting moiety with 2-pyridinyl dithio-derivatized trichothecenes.

Antibody Conjugation of NHS-Derivatized Trichothecenes. This conjugation was generally performed in 6.2 mM sodium borate buffer (0.5M, pH 8), containing the antibody stabilizer molecusol at 1% wt/vol. The NHS-derivatized trichothecene dissolved in 100% DMSO was added dropwise to a stirred solution of antibody at a final antibody concentration of 1.0 mg/ml reaction solution. To achieve a trichothecene loading of 6–9/antibody, NHS-derivatized trichothecene was offered at a 30:1 trichothecene:antibody molar ratio at a final concentration of 25% DMSO vol/vol. The reaction mixture was incubated with continuous stirring at room temperature for 1 hour prior to purification by size exclusion chromatography, extensive dialysis, concentration via membrane centrifugation and sterile filtration. Conjugates thus prepared were stored refrigerated (e.g., at 5°–10° C.) or quick frozen in liquid nitrogen and then stored at –70° C. until use).

Specifically for succinimidyl-2'-Roridin A 3-dithiopropionate conjugation to antibody, 0.40 ml of 6.2 mM sodium borate buffer (0.5M, pH 8.0) and 0.20 ml of 100 mg molecusol/ml $H_2O$ were added to 1.0 ml of 2.0 mg NR-LU-10 /ml in PBS (i.e., 6.2 mM sodium phosphate, 150 mM NaCl, pH 7.2). 0.50 ml of DMSO having 290 micrograms of succinimidyl-2'-Roridin A 3-dithiopropionate dissolved therein (for a 30:1 trichothecene:antibody molar offering ratio) was added dropwise and with stirring over a 10 second time period. To purify the resultant product, 1 ml aliquots of reaction solution were applied to PD-10 Sephadex columns (Pharmacia, Uppsala, Sweden) equilibrated in PBS containing 1% molecusol wt/vol. The eluted conjugate was collected in the 2.4–4.8 ml fraction. The PD-10 purified aliquots were then pooled, exhaustively dialyzed against PBS containing 1% molecusol (wt/vol) using Spectra/POR molecular porous membrane tubing (Spectrum Medical Industries, Inc., Los Angeles, Calif.), concentrated on a Centricon PM-30 Microconcentrator (Amicon Div., W. R. Grace & Co., Beverly, Mass.), and sterile filtered using a 2.2 micron Acrodisc (Gelman Sciences, Ann Arbor, Mich.). Conjugates thus prepared were stored refrigerated (e.g., at 5°–10° C.) or quick frozen in liquid nitrogen and then stored at –70° C. until use).

B. Antibody Conjugation of 2-Pyridinyl-Dithio-Derivatized Trichothecenes. In conjugation of 2-pyridinyl-dithio-derivatized trichothecenes, NR-LU-10 disulfides were first reduced by incubating NR-LU-10 at 5–10 mg in 1 ml of PBS containing 10–15 mM dithiothreitol for 15 minutes at room temperature. The reduced product was purified over a PD-10 column that had been equilibrated in degassed 0.1M sodium phosphate, pH 7.5, containing 0.1M NaCl, 1% molecusol wt/vol and 0.2 mM EDTA (Na salt). Immediately after reduced-disulfide NR-LU-10 purification, dropwise addition of 2-pyridinyl-dithio-derivatized trichothecene dissolved in DMSO (0.40 ml of DMSO, containing 432 micrograms of 3-(2-pyridinyldithio) propionate hydrazide 2'-Roridin A hydrazone or containing 337 micrograms of 3-(2-pyridinyldithio) propionate hydrazide 3-anguidine hydrazone or containing 459 micrograms of 3-(2-pyridinyldithio) propionate hydrazide 2'-acetyl-13'-Roridin A hydrazone) to 2 mg of the reduced disulfide NR-LU-10 solution (a 44:1 trichothecene:antibody molar offering ratio) was conducted with stirring. Generally in conducting the conjugation, the reaction concentration of antibody was 0.8–1.2 mg/ml, DMSO was 16–25% vol/vol, and trichothecene to antibody molar offering ranged from 40:1 to 50:1 (in order to achieve a loading of approximately 6 trichothecenes per antibody). After 1 hour of incubation at room temperature, purification proceeded analogously to the purification scheme described in Example XVII(A) above. Conjugates thus prepared were stored refrigerated (e.g., at 5°–10° C.) or quick frozen in liquid nitrogen and then stored at –70° C. until use).

C. Trichothecene-Polymer-Ligand Conjugation. Experimentation involving the use of a biotin-dextran-trichothecene conjugate in a pretargeting approach included:

- trace labeling using an I-125 PIP NHS ester of an available lysine of a 70,000 dalton dextran molecule that had been biotinylated in accordance with techniques discussed herein in Example XVII, yielding radiotagged dextran biotin (represented as dextran*-biotin);
- trichothecene drug conjugation to the remaining lysines using an NHS activated trichothecene;
- demonstration of binding of the drug-dextran*-biotin molecule to immobilized avidin; and
- assessment of serum clearance in mice.

Biotinylated dextran having a molecular weight of 70,000 daltons, with 18 moles of biotin covalently bound thereto and 18 additional lysine epsilon amino groups, was purchased from Sigma Chemical Co. (St. Louis, Mo.). To radiolabel the material, 4 mC of I-125 PIP NHS ester of specific activity of 2200 mCi/mmole (New England Nuclear, Boston, Mass.) in acetonitrile in a 2 ml glass vial was blown down to dryness in a nitrogen stream. 10 mg of biotinylated, lysine-derivatized dextran lyophilizate, reconstituted with 0.650 ml of 1.0M sodium borate, pH 9.0, was added to the iodinating compound and incubated at room temperature for 10 minutes. Following reaction, the radioiodinated dextran moiety was purified by size exclusion chromatography using a PD-10 column (Pharmacia, Uppsala, Sweden) equilibrated in phosphate buffered saline (i.e., 6.2M sodium phosphate, 150 mM NaCl, pH.7.2) containing 1% molecusol (Pharmatec, Alachua, Fl.). The biotin-dextran* eluted from the column in the 2.4–4.8 ml fractions at a specific activity of 0.2 mCi/mg and a concentration of 3.5 mg/ml.

To derivatize the biotin-dextran, with trichothecene, 0.9 ml of biotin-dextran, was diluted with 1.3 ml of sodium borate buffer, 0.3M, Ph 8.5, containing 1% molecusol followed by addition, with stirring of 1.2 ml of DMSO containing 1.2 mg of 2'-Desoxy-2'-alpha-(N-hydroxysuccinimidyl-3-dithiopropanoic acid)-Roridin A (i.e., 2:1 drug to available lysine molar ratio). After incubation for 1.5 hours at room temperature, each 1 ml aliquot of reaction mixture was purified as noted above with a PD-10 column equilibrated in PBS. Yields exceeded 85%.

To establish that the biotin-dextran*-trichothecene molecule was able to bind to avidin or streptavidin, 1 microgram of biotin-dextran* and 1 microgram of biotin-dextran*-trichothecene were incubated for 15 minutes at room temperature with 1 unit of avidin insolubilized on agarose beads (Sigma Chemical Co., St. Louis, Mo.) in 0.2 ml of 0.2M Pi buffer, pH 6.3 containing 150 mM NaCl. Following this incubation, the percent radioactivity bound to the agarose beads was assessed after dilution with 1.4 ml buffer, centrifugation of the agarose suspension and three washings of the pellets with 1.4 ml buffer. 100% binding was observed for both biotin-dextran, and biotin-dextran*-trichothecene.

Serum clearance studies of biotin-dextran, and biotin-dextran*-trichothecene were also performed in Balb C mice. Serial blood samplings revealed that he two molecules exhibited substantially similar serum clearance upon injection of 2 μCi thereof.

EXAMPLE XXI

Synthesis of DOTA-Biotin Conjugates

A. Synthesis of Nitro-Benzyl-DOTA.

The synthesis of aminobenzyl-DOTA was conducted substantially in accordance with the procedure of McMurry et al., *Bioconjugate Chem.*, 3: 108–117, 1992. The critical step in the prior art synthesis is the intermolecular cyclization between disuccinimidyl N-(tert-butoxycarbonyl)iminodiacetate and N-(2-aminoethyl)-4-nitrophenyl alaninamide to prepare 1-(tert-butoxycarbonyl)-5-(4-nitrobenzyl)-3,6,11-trioxo-1,4,7,10-tetraazacyclododecane. In other words, the critical step is the intermolecular cyclization between the bis-NHS ester and the diamine to give the cyclized dodecane. McMurry et al. conducted the cyclization step on a 30 mmol scale, dissolving each of the reagents in 100 ml DMF and adding via a syringe pump over 48 hours to a reaction pot containing 4 liters dioxane.

A 5× scale-up of the McMurry et al. procedure was not practical in terms of reaction volume, addition rate and reaction time. Process chemistry studies revealed that the reaction addition rate could be substantially increased and that the solvent volume could be greatly reduced, while still obtaining a similar yield of the desired cyclization product. Consequently on a 30 mmol scale, each of the reagents was dissolved in 500 ml DMF and added via addition funnel over 27 hours to a reaction pot containing 3 liters dioxane. The addition rate of the method employed involved a 5.18 mmol/hour addition rate and a 0.047M reaction concentration.

B. Synthesis of a D-alanine-linked conjugate with a preserved biotin carboxy moiety. A reaction scheme to form a compound of the following formula is discussed below.

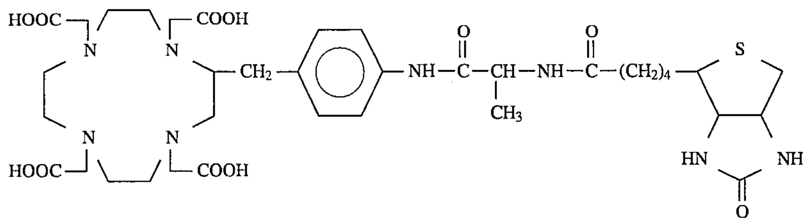

The D-alanine-linked conjugate was prepared by first coupling D-alanine (Sigma Chemical Co.) to biotin-NHS ester. The resultant biotinyl-D-alanine was then activated with 1-(3-dimethylaminopropyl)-3-ethyl-carbodiimide hydrochloride (EDCI) and N-hydroxysuccinimide (NHS). This NHS ester was reacted in situ with DOTA-aniline to give the desired product which was purified by preparative HPLC.

More specifically, a mixture of D-alanine (78 mg, 0.88 mmol, 1.2 equivalents), biotin-NHS ester (250 mg, 0.73 mmol, 1.0 equivalent), triethylamine (0.30 ml, 2.19 mmol, 3.0 equivalents) in DMF (4 ml) was heated at 110° C. for 30 minutes. The solution was cooled to 23° C. and evaporated. The product solid was acidified with glacial acetic acid and evaporated again. The product biotinyl-D-alanine, a white solid, was suspended in 40 ml of water to remove excess unreacted D-alanine, and collected by filtration. Biotinyl-D-alanine was obtained as a white solid (130 mg, 0.41 mmol) in 47% yield.

NHS (10 mg, 0.08 mmol) and EDCI (15 mg, 0.07 mmol) were added to a solution of biotinyl-D-alanine (27 mg, 0.08 mmol) in DMF (1 ml). The solution was stirred at 23° C. for 60 hours, at which time TLC analysis indicated conversion of the carboxyl group to the N-hydroxy succinimidyl ester. Pyridine (0.8 ml) was added followed by DOTA-aniline (20 mg, 0.04 mmol). The mixture was heated momentarily at approximately 100° C., then cooled to 23° C. and evaporated. The product, DOTA-aniline-D-alanyl-biotinamide was purified by preparative HPLC.

C. Synthesis of N-hydroxyethyl-linked conjugate.

Iminodiacetic acid dimethyl ester is condensed with biotin-NHS-ester to give biotinyl dimethyl iminodiacetate.

Hydrolysis with one equivalent of sodium hydroxide provides the monomethyl ester after purification from under and over hydrolysis products. Reduction of the carboxyl group with borane provides the hydroxyethyl amide. The hydroxyl group is protected with t-butyl-dimethyl-silylchloride. The methyl ester is hydrolysed, activated with EDCI and condensed with DOTA-aniline to form the final product conjugate.

D. Synthesis of N-Me-LC-DOTA-biotin. A reaction scheme is shown below.

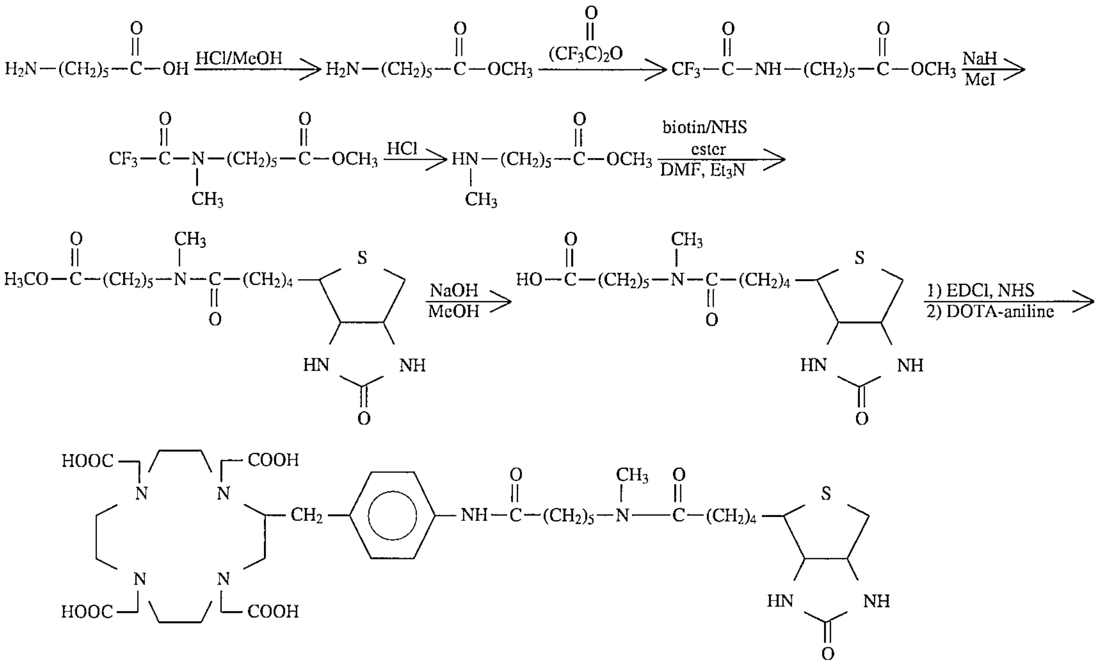

Esterification of 6-Aminocaproic acid (Sigma Chemical Co.) was carried out with methanolic HCl. Trifluoroacetylation of the amino group using trifluoroacetic anhydride gave N-6-(methylcapropyl)-trifluoroacetamide. The amide nitrogen was methylated using sodium hydride and iodomethane in tetrahydrofuran. The trifluoroacetyl protecting group was cleaved in acidic methanol to give methyl 6-methylamino-caproate hydrochloride. The amine was condensed with biotin-NHS ester to give methyl N-methylcaproylamido-biotin. Saponification afforded the corresponding acid which was activated with EDCI and NHS and, in situ, condensed with DOTA-aniline to give DOTA-benzylamido-N-methyl-caproylamido-biotin.

1. Preparation of methyl 6-aminocaproate hydrochloride. Hydrogen chloride (gas) was added to a solution of 20.0 g (152 mmol) of 6-minocaproic acid in 250 ml of methanol via rapid bubbling for 2–3 minutes. The mixture was stirred at 15°–25° C. for 3 hours and then concentrated to afford 27.5 g of the product as a white solid (99%):

H-NMR (DMSO) 9.35 (1H, broad t), 3.57 (3H, s), 3.14 (2H, quartet), 2.28 (2H, t), 1.48 (4H, multiplet), and 1.23 ppm (2H, multiplet).

2. Preparation of N-6-(methylcaproyl)trifluoroacetamide. To a solution of 20.0 g (110 mmol) of methyl 6-aminocaproate hydrochloride in 250 ml of dichloromethane was added 31.0 ml (22.2 mmol) of triethylamine. The mixture was cooled in an ice bath and trifluoroacetic anhydride (18.0 ml, 127 mmol) was added over a period of 15–20 minutes. The mixture was stirred at 0°–10° C. for 1 hour and concentrated. The residue was diluted with 300 ml of ethyl acetate and saturated aqueous sodium bicarbonate (3×100 ml). The organic phase was dried over anhydrous magnesium sulfate, filtered and concentrated to afford 26.5 g of the product as a pale yellow oil (100%):

H-NMR (DMSO) 3.57 (3H, s), 3.37 (2H, t), 3.08 (1.9H, quartet, N—CH$_3$), 2.93 (1.1H, s, N—CH$_3$), 2.30 (2H, t), 1.52 (4H, multiplet), and 1.23 ppm (2H, multiplet).

3. Preparation of methyl 6-N-methylamino-caproate hydrochloride. To a solution of 7.01 g (29.2 mmol) of N-6-(methylcaproyl)-trifluoroacetamide in 125 ml of anhydrous tetrahydrofuran was slowly added 1.75 g of 60% sodium hydride (43.8 mmol) in mineral oil. The mixture was stirred at 15°–25° C. for 30 minutes and then 6.2 g (43.7 mmol) of iodomethane was added. The mixture was stirred at 15°–25° C. for 17 hours and then filtered through celite. The solids were rinsed with 50 ml of tetrahydrofuran. The filtrates were combined and concentrated. The residue was diluted with 150 ml of ethyl acetate and washed first with 5% aqueous sodium sulfite (2×100 ml) and then with 100 ml of 1N aqueous hydrochloric acid. The organic phase was dried over anhydrous magnesium sulfate, filtered and concentrated to afford a yellow oily residue. The residue was diluted with 250 ml of methanol and then hydrogen chloride (gas) was rapidly bubbled into the mixture for 2–3 minutes. The resultant mixture was refluxed for 18 hours, cooled and concentrated. The residue was diluted with 150 ml of methanol and washed with hexane (3×150 ml) to remove mineral oil previously introduced with NaH. The methanol phase was concentrated to afford 4.91 g of the product as a yellow oil (86%):

H-NMR (DMSO) 8.80 (2H, broad s), 3.58 (3H, s), 2.81 (2H, multiplet), 2.48 (3H, s), 2.30 (2H, t), 1.52 (4H, multiplet), and 1.29 ppm (2H, multiplet).

4. Preparation of methyl 6-(N-methylcaproylamidobiotin. N-hydroxysuccinimidyl biotin (398 mg, 1.16 mmol) was added to a solution of methyl 6-(N-methyl) aminocaproate hydrochloride (250 mg, 1.28 mmol) in DMF (4.0 ml) and triethylamine (0.18 ml, 1.28 mmol). The mixture was heated in an oil bath at 100° C. for 10 minutes. The solution was evaporated, acidified with glacial acetic acid and evaporated again. The residue was chromatographed on a 25 mm flash chromatography column manufactured by Ace Glass packed with 50 g silica (EM Science, Gibbstown, N.J., particle size 0.40–0.63 mm) eluting with 15% MeOH/EtOAc. The product was obtained as a yellow oil (390 mg) in 79% yield.

5. Preparation of 6-(N-methyl-N-biotinyl) amino caproic acid. To a solution of methyl 6-(N-methyl-caproylamido-biotin (391 mg, 1.10 mmol) in methanol (2.5 ml) was added a 0.95N NaOH solution (1.5 ml). This solution was stirred at 23° C. for 3 hours. The solution was neutralized by the addition of 1.0M HCl (1.6 ml) and evaporated. The residue was dissolved in water, further acidified with 1.0M HCl (0.4 ml) and evaporated. The gummy solid residue was suspended in water and agitated with a spatula until it changed into a white powder. The powder was collected by filtration with a yield of 340 mg.

6. Preparation of DOTA-benzylamido-N-methyl-caproylamido-biotin. A suspension of 6-(N-methyl-N-biotinyl)amino caproic acid (29 mg, 0.08 mmol) and N-hydroxysuccinimide (10 mg, 0.09 mmol) in DMF (0.8 ml) was heated over a heat gun for the short time necessary for the solids to dissolve. To this heated solution was added EDCI (15 mg, 0.08 mmol). The resultant solution was stirred at 23° C. for 20 hours. To this stirred solution were added aminobenzyl-DOTA (20 mg, 0.04 mmol) and pyridine (0.8 ml). The mixture was heated over a heat gun for 1 minute. The produce was isoianed by preparative HPLC, yielding 3 mg.

E. Synthesis of a bis-DOTA conjugate with a preserved biotin carboxy group. A reaction scheme is shown below.

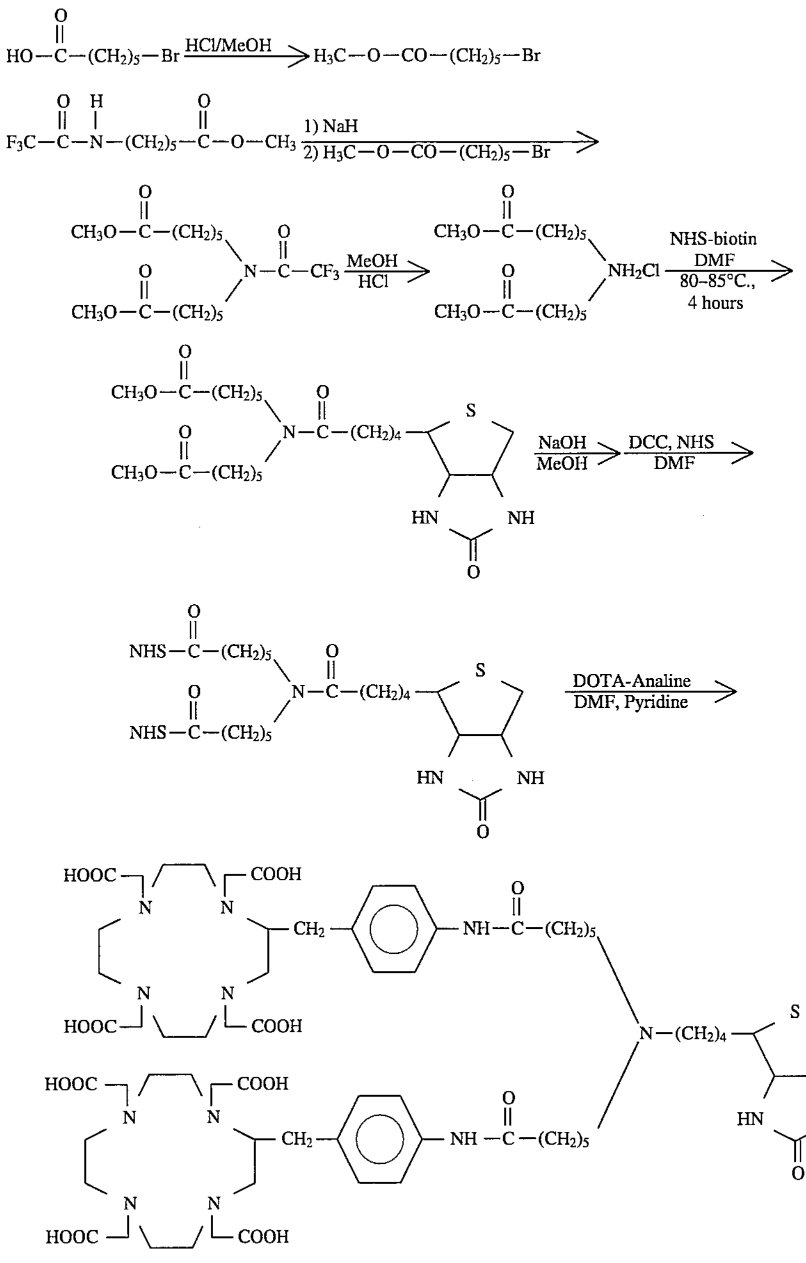

1. Preparation of methyl 6-bromocaproate (methyl 6-bromohexanoate). Hydrogen chloride (gas) was added to a solution of 5.01 g (25.7 mmol) of 6-bromocaproic acid in 250 ml of methanol via vigorous bubbling for 2–3 minutes. The mixture was stirred at 15°–25° C. for 3 hours and then concentrated to afford 4.84 g of the product as a yellow oil (90%):

H-NMR (DMSO) 3.58 (3H, s), 3.51 (2H, t), 2.29 (2H, t), 1.78 (2H, pentet), and 1.62–1.27 ppm (4H, m).

2. Preparation of N,N-bis-(methyl 6-hexanoyl)-amine hydrochloride. To a solution of 4.01 g (16.7 mmol) of N-(methyl 6-hexanoyl)-trifluoroacetamide (prepared in accordance with section D.2. herein) in 125 ml of anhydrous tetrahydrofuran was added 1.0 g (25 mmol) of 60% sodium hydride in mineral oil. The mixture was stirred at 15°–25° C. for 1 hour and then 3.50 g (16.7 mmol) of methyl 6-bromocaproate was added and the mixture heated to reflux. The mixture was stirred at reflux for 22 hours. NMR assay of an aliquot indicated the reaction to be incomplete. Consequently, an additional 1.00 g (4.8 mmol) of methyl 6-bromocaproate was added and the mixture stirred at reflux for 26 hours. MNR assay of an aliquot indicated the reaction to be incomplete. An additional 1.0 g of methyl 6-bromocaproate was added and the mixture stirred at reflux for 24 hours. NMR assay of an aliquot indicated the reaction to be near complete. The mixture was cooled and then directly filtered through celite. The solids were rinsed with 100 ml of tetrahydrofuran. The filtrates were combined and concentrated. The residue was diluted with 100 ml of methanol and washed with hexane (3×100 ml) to remove the mineral oil introduced with the sodium hydride. The methanol phase was treated with 6 ml of 10N aqueous sodium hydroxide and stirred at 15°–25° C. for 3 hours. The mixture was concentrated. The residue was diluted with 100 ml of deionized water and acidified to pH 2 with concentrated HCl. The mixture was washed with ether (3×100 ml). The aqueous phase was concentrated, diluted with 200 ml of dry methanol and then hydrogen chloride gas was bubbled through the mixture for 2–3 minutes. The mixture was stirred at 15°–25° C. for 3 hours and then concentrated. The residue was diluted with 50 ml of dry methanol and filtered to remove inorganic salts. The filtrate was concentrated to afford 1.98 g of the product as a white solid (38%):

H-NMR (DMSO) 8.62 (2H, m) 3.58 (6H, s), 2.82 (4H, m) 2.30 (4H, t), 1.67–1.45 (8H, m) and 1.38–1.22 ppm (4H, m).

3. Preparation of N,N=bis-(methyl 6-hexanoyl)biotinamide. To a solution of 500 mg (1.46 mmol) of N-hydroxysuccinimidyl biotin in 15 ml of dry dimethylformamide was added 600 mg (1.94 mmol) of N,N-bis(methyl 6-hexanoyl)amine hydrochloride followed by 1.0 ml of triethylamine. The mixture was stirred at 80°–85° C. for 3 hours and then cooled and concentrated. The residue was chromatographed on silica gel, eluting with 20% methanol/ethyl acetate, to afford 620 mg of the product as a near colorless oil (85%):

H-NMR ($CDCl_3$) 5.71 (1H, s), 5.22 (1H, s), 4.52 (1H, m), 4.33 (1H, m), 3.60 (3H, s), 3.58 (3H, s), 3.34–3.13 (5H, m), 2.92 (1H, dd), 2.75 (1H, d), 2.33 (6H, m) and 1.82–1.22 ppm (18H, m); TLC-$R_f$ 0.39 (20:80 methanol/ethyl acetate).

4. Preparation of N,N-bis-(6-hexanoyl)biotinamide. To a solution of 610 mg (0.819 mmol) of N,N-bis-(methyl 6-hexanoyl)-biotinamide in 35 ml of methanol was added 5.0 ml of 1N aqueous sodium hydroxide. The mixture was stirred at 15°–25° C. for 4.5 hours and then concentrated. The residue was diluted with 50 ml of deionized water acidified to pH 2 with 1N aqueous hydrochloric acid at 4° C. The product, which precipitated out as a white solid, was isolated by vacuum filtration and dried under vacuum to afford mg(84%):

H-NMR (DMSO) 6.42 (1H, s), 6.33 (1H, s), 4.29 (1H, m), 4.12 (1H, m), 3.29–3.04 (5H, m), 2.82 (1H, dd), 2.57 (1H, d), 2.21 (6H, m) and 1.70–1.10 ppm (18H, m).

5. Preparation of N',N'-bis-(N-hydroxysuccinimidyl 6-hexanoyl)-biotinamide. To a solution of 220 mg (0.467 mmol) of N,N-bis-(6-hexanoyl)biotinamide in 3 ml of dry dimethylformamide was added 160 mg (1.39 mmol) of N-hydroxysuccinimide followed by 210 mg (1.02 mmol) of dicyclohexyl-carbodiimide. The mixture was stirred at 15°–25° C. for 17 hours and then concentrated. The residue was chromatographed on silica gel, eluting with 0.1:20:80 acetic acid/methanol/ethyl acetate, to afford 148 mg of the product as a foamy off-white solid (48%):

H-NMR (DMSO) 6.39 (1H, s), 6.32 (1H, s), 4.29 (1H, m), 4,12 (1H, m), 3.30–3.03 (5H, m), 2.81 (9H, dd and s), 2.67 (4H, m), 2.57 (1H, d), 2.25 (2H, t), 1.75–1.20 (18H, m); TLC-$R_f$ 0.37 (0.1:20:80 acetic acid/methanol/ethyl acetate).

6. Preparation of N,N-bis-(6-hexanoylamidobenzyl-DOTA)-biotinamide. To a mixture of 15 mg of DOTA-benzylamine and 6.0 mg of N',N'-bis-(N-hydroxysuccinimidyl 6-hexanoyl)-biotinamide in 1.0 ml of dry dimethylformamide was added 0.5 ml of dry pyridine. The mixture was stirred at 45°–50° C. for 4.5 hours and at 15°–25° C. for 12 hours. The mixture was concentrated and the residue chromatographed on a 2.1×2.5 cm octadecylsilyl (ODS) reverse-phase preparative HPLC column eluting with a –20 minute gradient profile of 0.1:95:5 to 0.1:40:60 trifluoroacetic acid:water:acetonitrile at 13 ml/minute to afford the desired product. The retention time was 15.97 minutes using the aforementioned gradient at a flow rate of 1.0 ml/minute on a 4.6 mm×25 cm ODS analytical HPLC column.

F. Synthesis of an N-methyl-glycine linked conjugate. A reaction scheme for this synthesis is shown below.

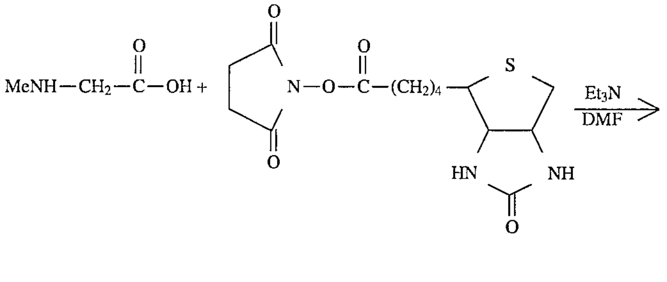

-continued

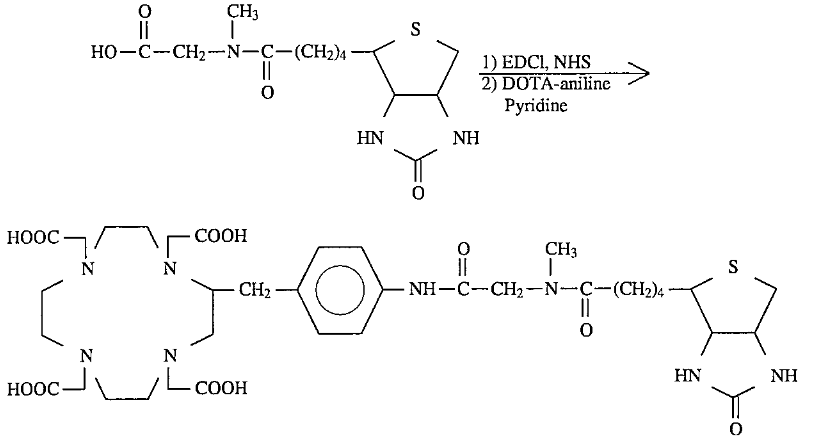

The N-methyl glycine-linked DOTA-biotin conjugate was prepared by an analogous method to that used to prepare D-alanine-linked DOTA-biotin conjugates. N-methyl-glycine (trivial name sarcosine, available from Sigma Chemical Co.) was condensed with biotin-NHS ester in DMF and triethylamine to obtain N-methyl glycyl-biotin. N-methyl-glycyl biotin was then activated with EDCI and NHS. The resultant NHS ester was not isolated and was condensed in situ with DOTA-aniline and excess pyridine. The reaction solution was heated at 60° C. for 10 minutes and then evaporated. The residue was purified by preparative HPLC to give [(N-methyl-N-biotinyl)-N-glycyl]-aminobenzyl-DOTA.

1. Preparation of (N-methyl)glycyl biotin. DMF (8.0 ml) and triethylamine (0.61 ml, 4.35 mmol) were added to solids N-methyl glycine (182 mg, 2.05 mmol) and N-hydroxy-succinimidyl biotin (500 mg, 1.46 mmol). The mixture was heated for 1 hour in an oil bath at 85° C. during which time the solids dissolved producing a clear and colorless solution. The solvents were then evaporated. The yellow oil residue was acidified with glacial acetic acid, evaporated and chromatographed on a 27 mm column packed with 50 g silica, eluting with 30% MeOH/EtOAc 1% HOAc to give the product as a white solid (383 mg) in 66% yield.

H-NMR (DMSO): 1.18–1.25 (m, 6H, $(CH_2)_3$), 2.15, 2.35 (2 t's, 2H, $CH_2CO$), 2.75 (m, 2H, $SCH_2$), 2.80, 3.00 (2 s's, 3H, $NCH_3$), 3.05–3.15 (m, 1H, SCH), 3.95, 4.05 (2 s's, 2H, $CH_2N$), 4.15, 4.32 (2 m's, 2H, 2CHN's), 6.35 (s, NH), 6.45 (s, NH).

2. Preparation of [(N-methyl-N-biotinyl)glycyl]aminobenzyl-DOTA. N-hydroxysuccinimide (10 mg, 0.08 mmol) and EDCI (15 mg, 6.08 mmol) were added to a solution of (N-methylglycyl biotin (24 mg, 0.08 mmol) in DMF (1.0 ml). The solution was stirred at 23° C. for 64 hours. Pyridine (0.8 ml) and aminobenzyl-DOTA (20 mg, 0.04 mmol) were added. The mixture was heated in an oil bath at 63° C. for 10 minutes, then stirred at 23° C. for 4 hours. The solution was evaporated. The residue was purified by preparative HPLC to give the product as an off white solid (8 mg, 0.01 mmol) in 27% yield.

H-NMR ($D_2O$): 1.30–1.80 (m, 6H), 2.40, 2.55 (2 t's, 2H, $CH_2CO$), 2.70–4.2 (complex multiplet), 4.35 (m, CHN), 4.55 (m, CHN), 7.30 (m, 2H, benzene hydrogens), 7.40 (m, 2H, benzene hydrogens).

G. Synthesis of a short chain amine-linked conjugate with a reduced biotin carboxy group. A two-part reaction scheme is shown below.

1.

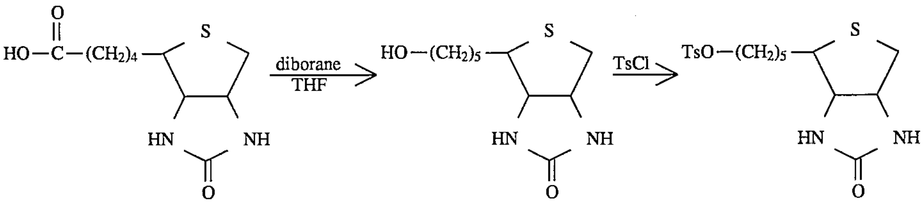

(biotin-OTs)

2.

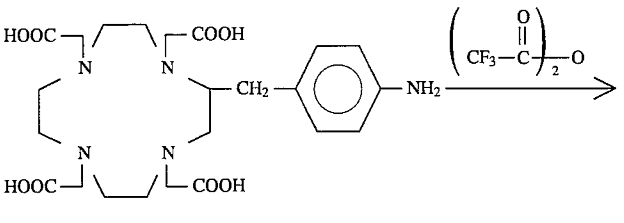

-continued

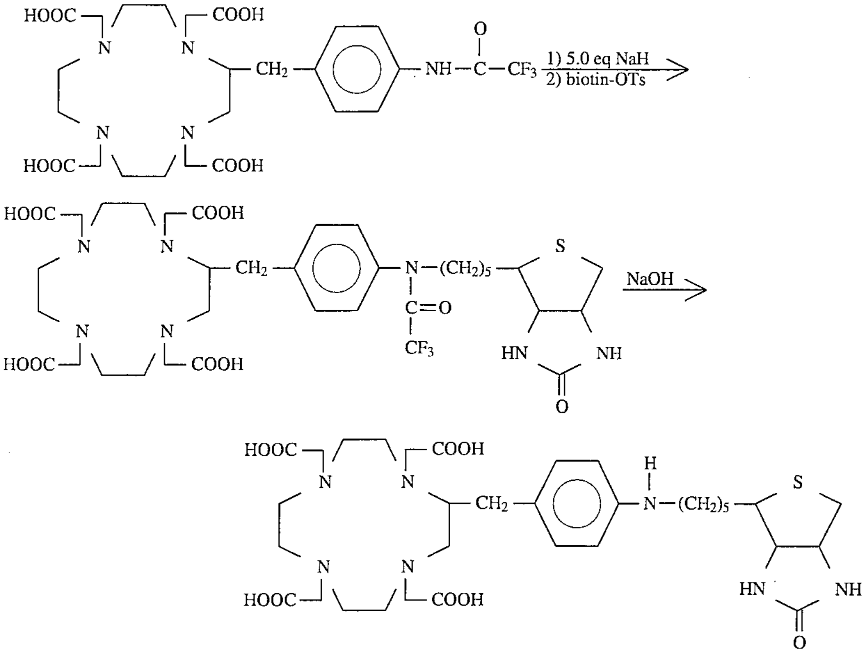

The bionin carboxyl group is reduced with diborane in THF to give a primary alcohol. Tosylation of the alcohol with tosyl chloride in pyridine affords the primary tosylate. Aminobenzyl DOTA is acylated with trifluoroacetic anhydride in pyridine to give (N-trifluoroacetyl)aminobenzyl-DOTA. Deprotonation with 5.0 equivalents of sodium hydride followed by displacement of the biotin tosylate provides the (N-trifluoracetamido-N-descarboxylbiotinyl)aminobenzyl-DOTA. Acidic cleavage of the N-trifluoroacetamide group with HCl(g) in methanol provides the amine-linked DOTA-biotin conjugate.

EXAMPLE XXII

Clearing Agent Evaluation Experimentation

The following experiments conducted on non-tumor-bearing mice were conducted using female BALB/c mice (20–25 g). For tumor-bearing mice experimentation, female nude mice were injected subcutaneously with LS-180 tumor cells, and, after 7 d, the mice displayed 50–100 mg tumor xenografts. The monoclonal antibody used in these experiments was NR-LU-10. When radiolabeled, the NR-LU-10-streptavidin conjugate was radiolabeled with I-125 using procedures described herein. When radiolabeled, PIP-biocytin was labeled with I-131 or I-125 using procedures described herein.

A. Utility of Asialoorosomucoid-Biotin (AO-Bt) in Reducing Circulating Radioactivity from a Subsequently Administered Radiolabeled Biotin Ligand. Mice bearing LS-180 colon tumor xenografts were injected with 200 micrograms NR-LU-10 antibody-streptavidin (MAb-StrAv) conjugate at time 0, which was allowed to prelocalize to tumor for 22 hours. At that time, 20 micrograms of AO-Bt was administered to one group of animals. Two hours later, 90 micrograms of a radioisotope-bearing, ligand-containing small molecule (PIP-biotin-dextran prepared as discussed in part B hereof) was administered to this group of mice and also to a group which had not received AO-Bt. The results of this experiment with respect to radiolabel uptake in tumor and clearance from the blood indicated that tumor-targeting of the radiolabeled biotin-containing conjugate was retained while blood clearance was enhanced, leading to an overall improvement in amount delivered to target/amount located in serum. The AUC tumor/AUC blood with clearing agent was 6.87, while AUC tumor/AUC blood without clearing agent was 4.45. Blood clearance of the circulating MAb-StrAv conjugate was enhanced with the use of clearing agent. The clearing agent was radiolabeled in a separate group of animals and found to bind directly to tumor at very low levels (1.7 pmol/g at a dose of 488 total pmoles (0.35%ID/g), indicating that it does not significantly compromise the ability of tumor-bound MAb-StrAv to bind subsequently administered radiolabeled ligand.

B. Preparation Protocol for PIP-Biotin-Dextran. A solution of 3.0 mg biotin-dextran, lysine fixable (BDLF, available from Sigma Chemical Co., St. Louis, Mo., 70,000 dalton molecular weight with approximately 18 biotins/molecule) in 0.3 ml PBS and 0.15 ml 1M sodium carbonate, pH 9.25, was added to a dried residue (1.87 mCi) of N-succinimidyl p-I-125-iodobenzoate prepared in accordance with Wilbur, et al., *J. Nucl. Med.*, 30: 216–226, 1989.

C. Dosing Optimization of AO-Bt. Tumored mice receiving StrAv-MAb as above, were injected with increasing doses of AO-Bt (0 micrograms, 20 micrograms, 50 micrograms, 100 micrograms and 200 micrograms). Tumor uptake of I-131-PIP-biocytin (5.7 micrograms, administered 2 hours after AO-Bt administration) was examined. Increasing doses of AO-Bt had no effect on tumor localization of MAb-StrAv. Data obtained 44 hours after AO-Bt administration showed the same lack of effect. This data indicates that AO-Bt dose not cross-link and internalize MAb-StrAv on the tumor surface, as had been noted for avidin administered following biotinylated antibody.

PIP-biocytin tumor localization was inhibited at higher doses of AO-Bt. This effect is most likely due to reprocessing and distribution to tumor of biotin used to derivatize AO-Bt. Optimal tumor to blood ratios (% injected dose of radiolabeled ligand/gram weight of tumor divided by % injected dose of radioligand/gram weight of blood were achieved at the 50 microgram dose of AO-Bt. Biodistributions conducted following completion of the protocols employing a 50 microgram AO-Bt dose revealed low retention of radiolabel in all non-target tissues (1.2 pmol/g in blood; 3.5 pmol/gram in tail; 1.0 pmol/g in lung; 2.2 pmol/g in liver; 1.0 pmol/g is spleen; 7.0 pmol/g in stomach; 2.7 pmol/g in kidney; and 7.7 pmol/g in intestine). With 99.3 pmol/g in tumor, these results indicate effective decoupling of the PIP-biocytin biodistribution from that of the MAb-StrAy at all sites except tumor. This decoupling occurred at all clearing agent doses in excess of 50 micrograms as well. Decreases in tumor localization of PIP-biocytin was the significant result of administering clearing agent doses in excess of 50 micrograms. In addition, the amount of PIP-biocytin in non-target tissues 44 hours after administration was identical to localization resulting from administration of PIP-biocytin alone (except for tumor, where negligible accretion was seen when PIP-biocytin was administered alone), indicating effective decoupling.

D. Further Investigation of Optimal Clearing Agent Dose. Tumored mice injected with MAb-StrAv at time 0 as above; 50 micrograms of AO-Bt at time 22 hours; and 545 microcuries of I-131-PIP-biocytin at time 25 hours. Whole body radiation was measured and compared to that of animals that had not received clearing agent. 50 micrograms of AO-Bt was efficient in allowing the injected radioactivity to clear from the animals unimpeded by binding to circulating MAb-StrAv conjugate. Tumor uptake of I-131-PIP-biocytin was preserved at the 50 microgram clearing agent dose, with AUC tumor/AUC blood of 30:1 which is approximately 15-fold better than the AUC tumor/AUC blood achieved in conventional antibody-radioisotope therapy using this model.

E. Galactose-and Biotin-Derivatization of Human Serum Albumin (HSA). HSA was evaluated because it exhibits the advantages of being both inexpensive and non-immunogenic. HSA was derivatized with varying levels of biotin (1-about 9 biotins/molecule) via analogous chemistry to that previously described with respect to AO. More specifically, to a solution of HSA available from Sigma Chemical Co. (5–10 mg/ml in PBS) was added 10% v/v 0.5M sodium borate buffer, pH 8.5, followed by dropwise addition of a DMSO solution of NHS-LC-biotin (Sigma Chemical Co.) to the stirred solution at the desired molar offering (relative molar equivalents of reactants). The final percent DMSO in the reaction mixture should not exceed 5%. After stirring for 1 hour at room temperature, the reaction was complete. A 90% incorporation efficiency for biotin on HSA was generally observed. As a result, if 3 molar equivalences of the NHS ester of LC-biotin was introduced, about 2.7 biotins per HSA molecule were obtained. Unreacted biotin reagent was removed from the biotin-derivatized HSA using G-25 size exclusion chromatography. Alternatively, the crude material may be directly galactosylated. The same chemistry is applicable for biotinylating non-previously biotinylated dextran.

HSA-biotin was then derivatized with from 12 to 15 galactoses/molecule. Galactose derivatization of the biotinylated HSA was performed according to the procedure of Lee, et al., *Biochemistry,* 15: 3956, 1976. More specifically, a 0.1M methanolic solution of cyanomethyl-2,3,4,6-tetra-O-acetyl-1-thio-D-galactopyranoside was prepared and reacted with a 10% v/v 0.1M NaOMe in methanol for 12 hours to generate the reactive galactosyl thioimidate. The galactosylation of biotinylated HSA began by initial evaporation of the anhydrous methanol from a 300 fold molar excess of reactive thioimidate. Biotinylated HSA in PBS, buffered with 10% v/v 0.5M sodium borate, was added to the oily residue. After stirring at room temperature for 2 hours, the mixture was stored at 4° C. for 12 hours. The galactosylated HSA-biotin was then purified by G-25 size exclusion chromatography or by buffer exchange to yield the desired product. The same chemistry is exploitable to galactosylating dextran. The incorporation efficiency of galactose on HSA is approximately 10%.

70 micrograms of Galactose-HSA-Biotin (G-HSA-B), with 12–15 galactose residues and 9 biotins, was administered to mice which had been administered 200 micrograms of StrAv-MAb or 200 microliters of PBS 24 hours earlier. Results indicated that G-HSA-B is effective in removing StrAv-MAb from circulation. Also, the pharmacokinetics of G-HSA-B is unperturbed and rapid in the presence or absence of circulating MAb-StrAv.

F. Non-Protein Clearing Agent. A commercially available form of dextran, molecular weight of 70,000 daltons, prederivatized with approximately 18 biotins/molecule and having an equivalent number of free primary amines was studied. The primary amine moieties were derivatized with a galactosylating reagent, substantially in accordance with the procedure therefor described above in the discussion of HSA-based clearing agents, at a level of about 9 galactoses/molecule. The molar equivalence offering ratio of galactose to HSA was about 300:1, with about one-third of the galactose being converted to active form. 40 Micrograms of galactose-dextran-biotin (GAL-DEX-BT) was then injected i.v. into one group of mice which had received 200 micrograms MAb-StrAv conjugate intravenously 24 hours earlier, while 80 micrograms of GAL-DEX-BT was injected into other such mice. GAL-DEX-BT was rapid and efficient at clearing StrAv-MAb conjugate, removing over 66% of circulating conjugate in less than 4 hours after clearing agent administration. An equivalent effect was seen at both clearing agent doses, which correspond to 1.6 (40 micrograms) and 3.2 (80 micrograms) times the stoichiometric amount of circulating StrAv conjugate present.

G. Dose Ranging for G-HSA-B Clearing Agent. Dose ranging studies followed the following basic format:

200 micrograms MAb-StrAv conjugate administered;

24 hours later, clearing agent administered; and 2 hours later, 5.7 micrograms PIP-biocytin administered.

Dose ranging studies were performed with the G-HSA-B clearing agent, starting with a loading of 9 biotins per molecule and 12–15 galactose residues per molecule. Doses of 20, 40, 70 and 120 micrograms were administered 24 hours after a 200 microgram dose of MAb-StrAv conjugate. The clearing agent administrations were followed 2 hours later by administration of 5.7 micrograms of I-131-PIP-biocytin. Tumor uptake and blood retention of PIP-biocityn was examined 44 hours after administration thereof (46 hours after clearing agent administration). The results showed that a nadir in blood retention of PIP-biocytin was achieved by all doses greater than or equal to 40 micrograms of G-HSA-B. A clear, dose-dependent decrease in tumor binding of PIP-biocytin at each increasing dose of G-HSA-B was present, however. Since no dose-dependent effect on the localization of MAb-StrAv conjugate at the tumor was observed, this data was interpreted as being indicative of relatively higher blocking of tumor-associated MAb-StrAv conjugate by the release of biotin from catabolized clearing agent. Similar results to those described earlier for the asialoorosomucoid clearing agent regarding plots of tumor/blood ratio were found with respect to G-HSA-B, in that an optimal balance between blood clearance and tumor retention occurred around the 40 microgram dose.

Because of the relatively large molar amounts of biotin that could be released by this clearing agent at higher doses, studies were undertaken to evaluate the effect of lower levels of biotinylation on the effectiveness of the clearing agent. G-HSA-B, derivatized with either 9, 5 or 2 biotins/molecule, was able to clear MAb-StrAv conjugate from blood at equal protein doses of clearing agent. All levels of biotinylation yielded effective, rapid clearance of MAb-StrAv from blood.

Comparison of these 9-, 5-, and 2-biotin-derivatized clearing agents with a single biotin G-HSA-B clearing agent was carried out in tumored mice, employing a 60 microgram dose of each clearing agent. This experiment showed each clearing agent to be substantially equally effective in blood clearance and tumor retention of MAb-StrAv conjugate 2 hours after clearing agent administration. The G-HSA-B with a single biotin was examined for the ability to reduce binding of a subsequently administered biotinylated small molecule (PIP-biocytin) in blood, while preserving tumor binding of PIP-biocytin to prelocalized MAb-StrAv conjugate. Measured at 44 hours following PIP-biocytin administration, tumor localization of both the MAb-StrAv conjugate and PIP-biocityn was well preserved over a broad dose range of G-HSA-B with one biotin/molecule (90 to 180 micrograms). A progressive decrease in blood retention of PIP-biocytin was achieved by increasing doses of the single biotin G-HSA-B clearing agent, while tumor localization remained essentially constant, indicating that this clearing agent, with a lower level of biotinylation, is preferred. This preference arises because the single biotin G-HSA-B clearing agent is both effective at clearing MAb-StrAv over a broader range of doses (potentially eliminating the need for patient-to-patient titration of optimal dose) and appears to release less competing biotin into the systemic circulation than the same agent having a higher biotin loading level.

Another way in which to decrease the effect of clearing agent-released biotin on active agent-biotin conjugate binding to prelocalized targeting moiety-streptavidin conjugate is to attach the protein or polymer or other primary clearing agent component to biotin using a retention linker. A retention linker has a chemical structure that is resistant to agents that cleave peptide bonds and, optionally, becomes protonated when localized to a catabolizing space, such as a lysosome, preferred retention linkers of the present invention are short strings of D-amino acids or small molecules having both of the characteristics set forth above. An exemplary retention linker of the present invention is cyanuric chloride, which may be interposed between an epsilon amino group of a lysine of a proteinaceous primary clearing agent component and an amine moiety of a reduced and chemically altered biotin carboxy moiety (which has been discussed above) to form a compound of the structure set forth below.

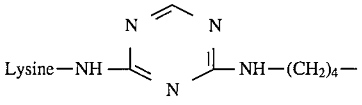

When the compound shown above is catabolized in a catabolizing space, the heterocyclic ring becomes protonated. The ring protonation prevents the catabolite from exiting the lysosome. In this manner, biotin catabolites containing the heterocyclic ring are restricted to the site(s) of catabolism and, therefore, do not compete with active-agent-biotin conjugate for prelocalized targeting moiety-streptavidin target sites.

Comparisons of tumor/blood localization of radiolabeled PIP-biocytin observed in the G-HSA-B dose ranging studies showed that optimal tumor to background targeting was achieved over a broad dose range (90 to 180 micrograms), with the results providing the expectation that even larger clearing agent doses would also be effective. Another key result of the dose ranging experimentation is that G-HSA-B with an average of only 1 biotin per molecule is presumably only clearing the MAb-StrAv conjugate via the Ashwell receptor mechanism only, because too few biotins are present to cause cross-linking and aggregation of MAb-StrAv conjugates and clearing agents with such aggregates being cleared by the reticuloendothelial system.

H. Tumor Targeting Evaluation Using G-HSA-B. The protocol for this experiment was as follows:

Time 0: administer 400 micrograms MAb-StrAv conjugate;

Time 24 hours: administer 240 micrograms of G-HSA-B with one biotin and 12–15 galactoses and Time 26 hours: administer 6 micrograms of

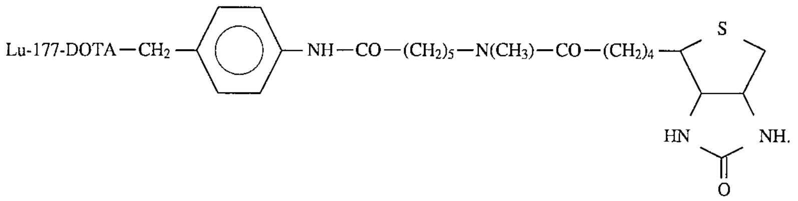

Lu-177 is complexed with the DOTA chelate using known techniques therefor.

Efficient delivery of the Lu-177-DOTA-biotin small molecule was observed, 20–25% injected dose/gram of tumor. These values are equivalent with the efficiency of the delivery of the MAb-StrAv conjugate. The AUC tumor/AUC blood obtained for this non-optimized clearing agent dose was 300% greater than that achievable by comparable direct MAb-radiolabel administration. In addition, the HSA-based clearing agent is expected to exhibit a low degree of immunogenicity in humans.

Kits containing one or more of the components described above are also contemplated. For instance, radiohalogenated biotin may be provided in a sterile container for use in pretargeting procedures. A chelate-biotin conjugate provided in a sterile container is suitable for radiometallation by the consumer; such kits would be particularly amenable for use in pretargeting protocols. Alternatively, radiohalogenated biotin and a chelate-biotin conjugate may be vialed in a non-sterile condition for use as a research reagent.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A biotin-DOTA conjugate on the following formula:

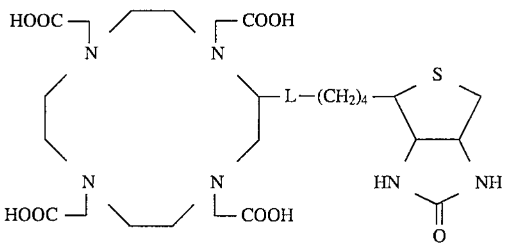

wherein a linker L is selected from the group consisting of:

1) a D-amino acid-containing linker of the formula

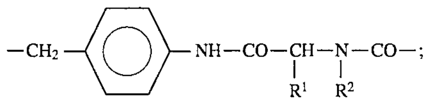

2) a linker of the formula

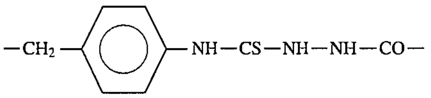

3) a linker of the formula

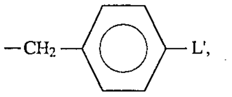

wherein L' is selected from the group consisting of:

a) —NH—CO—$(CH_2)_n$—O—;

b) —NH—;

c) 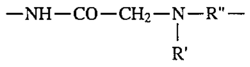

d) —NH—CS—NH—; and e) —NH—CO—$(CH_2)_n$—NH—, wherein $R^I$ is hydrogen; $C_1$–$C_5$ lower alkyl; lower alkyl substituted with one or more hydrophilic groups; glucuronide-substituted amino acids; or other glucuronide derivatives;

$R^2$ is hydrogen; lower alkyl; substituted lower alkyl having one or more substituents selected from the group consisting of hydroxy, sulfate, and phosphonate; or a hydrophilic moiety;

$R^3$ is hydrogen; an amine; a lower alkyl; a hydroxy-, sulfate- or phosphonate-substituted lower alkyl; a glucuronide; or a glucuronide-derivatized amino acid;

$R^4$ is hydrogen, lower alkyl or

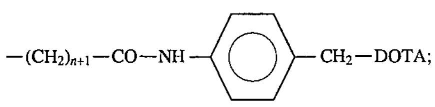

R' is hydrogen; —$(CH_2)_2$—OH or a sulfate or

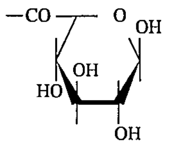

phosphonate derivative thereof; or

R" is a bond or —$(CH_2)_n$—CO—NH—; and n ranges from 0–5 and wherein both $R^3$ and $R^4$ cannot both be hydrogen.

2. A biotin-DOTA conjugate of claim 1 wherein L is a D-amino acid-incorporating a linker of the formula

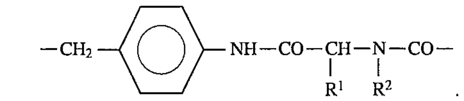

3. A biotin-DOTA conjugate of claim 2 wherein $R^1$ is $CH_3$ and $R^2$ is H.

4. A biotin-DOTA conjugate of claim 1 wherein L is a linker of the formula

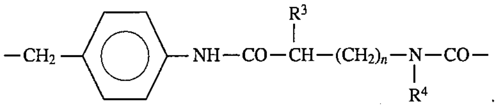

5. A biotin-DOTA conjugate of claim 4 wherein $R^3$ is hydrogen; $R^4$ is $CH_3$; and n is 4.

6. A biotin-DOTA conjugate of claim 4 wherein $R^3$ is hydrogen; $R^4$ is $CH_3$; and n is 0.

7. A biotin-DOTA conjugate of claim 4 wherein $R^3$ is hydrogen; $R^4$ is

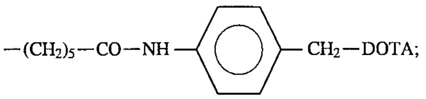

and n is 4.

8. A biotin-DOTA conjugate of claim 1 wherein L is a linker of the formula

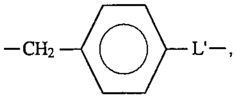

wherein L' is selected from the group consisting of:

a) —NH—CO—$(CH_2)_n$—O—;

b) —NH—;

c) 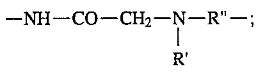

d) —NH—CS—NH—; and e) —NH—CO—$(CH_2)_n$—NH— or the bis-DOTA derivative thereof.

9. The biotin-DOTA conjugate of claim 1 wherein said hydrophilic groups are selected from the group consisting of: $(CH_2)_m$—OH, $(CH_2)_m$—$OSO_3$, $(CH_2)_m$—$SO_3$, and

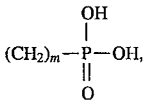

where m is 1 or 2.

* * * * *